United States Patent
Molina et al.

(10) Patent No.: US 11,986,819 B2
(45) Date of Patent: May 21, 2024

(54) METHOD FOR THE PREPARATION OF BIOSYNTHETIC DEVICE AND THEIR USES IN DIAGNOSTICS

(71) Applicants: SKILLCELL, Jarry (FR); CENTRE NATIONAL DE LA RECHERCHE SCIENTIFIQUE (CNRS), Paris (FR); CHU MONTPELLIER, Montpellier (FR)

(72) Inventors: Franck Molina, Les Matelles (FR); Alexis Courbet, Issy les Moulineaux (FR); Francisco Santos Schneider, Montpellier (FR)

(73) Assignees: SKILLCELL, Jarry (FR); CENTRE NATIONAL DE LA RECHERCHE SCIENTIFIQUE, Paris (FR); CHU MONTPELLIER, Montpellier (FR)

( * ) Notice: Subject to any disclaimer, the term of this patent is extended or adjusted under 35 U.S.C. 154(b) by 638 days.

(21) Appl. No.: 16/090,291

(22) PCT Filed: Apr. 13, 2017

(86) PCT No.: PCT/IB2017/000683
§ 371 (c)(1),
(2) Date: Oct. 1, 2018

(87) PCT Pub. No.: WO2017/178896
PCT Pub. Date: Oct. 19, 2017

(65) Prior Publication Data
US 2019/0111422 A1     Apr. 18, 2019

(30) Foreign Application Priority Data
Apr. 13, 2016  (EP) .................................. 16165189

(51) Int. Cl.
*B01L 3/00*   (2006.01)
*B82Y 5/00*   (2011.01)
(Continued)

(52) U.S. Cl.
CPC ............. *B01L 3/5027* (2013.01); *B82Y 10/00* (2013.01); *G01N 33/5432* (2013.01);
(Continued)

(58) Field of Classification Search
CPC ....... B01L 3/5027; G06N 3/002; B82Y 10/00; B82Y 15/00; B82Y 5/00; G01N 33/5432; G01N 33/573; G16C 99/00
See application file for complete search history.

(56) References Cited

U.S. PATENT DOCUMENTS

2012/0077184 A1   3/2012  Hu
2013/0065257 A1*  3/2013  Wang .................... C12Q 1/006
                                              435/14
(Continued)

FOREIGN PATENT DOCUMENTS

CN        103951803          7/2014
WO   WO-2011102885 A1 *  8/2011   ......... G01N 27/4146

OTHER PUBLICATIONS

Wang J. et al. (2010) "Digital biosensors with built-in logic for biomedical applications-biosensors based on a biocomputing concept", Analytical and Bioanalytical Chemistry, vol. 398, No. 4, pp. 1591-1603, (Year: 2010).*
(Continued)

*Primary Examiner* — Yoshihisa Ishizuka
(74) *Attorney, Agent, or Firm* — Arrigo, Lee, Guttman & Mouta-Bellum, LLP; Carla Mouta-Bellum

(57) ABSTRACT

The present invention is directed to a method for the preparation of a non-living micro/nanoscale biosynthetic device capable of giving an information of a state of a
(Continued)

Figure 1A:
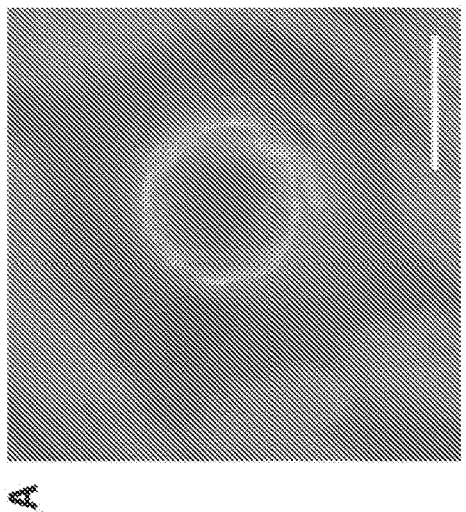

system to analyse. Preferably, said device is used as an assay diagnostic, or to predict the risk, of a disease, or for the classification of mammal, preferably human pathologies. The invention also relates to a method for the identification and/or the quantification of a compound in a sample. Finally the present invention includes a kit comprising the biosynthetic device obtained by the method of the present invention.

7 Claims, 71 Drawing Sheets

(51) Int. Cl.
| | |
|---|---|
| B82Y 10/00 | (2011.01) |
| B82Y 15/00 | (2011.01) |
| G01N 33/543 | (2006.01) |
| G01N 33/573 | (2006.01) |
| G06N 3/00 | (2023.01) |
| G16C 99/00 | (2019.01) |

(52) U.S. Cl.
CPC ........... *G01N 33/573* (2013.01); *G06N 3/002* (2013.01); *G16C 99/00* (2019.02); *B82Y 5/00* (2013.01); *B82Y 15/00* (2013.01)

(56) References Cited

U.S. PATENT DOCUMENTS

| | | | | |
|---|---|---|---|---|
| 2016/0120890 | A1* | 5/2016 | Singh | A61K 31/095 514/35 |
| 2016/0357935 | A1* | 12/2016 | Pottala | G16H 50/30 |
| 2018/0104307 | A1* | 4/2018 | Ghosh | C07K 14/4705 |

OTHER PUBLICATIONS

Li Zhao., Boronic Acid as Glucose-Sensitive Agent Regulates Drug Delivery for Diabetes Treatment., Materials 2017, 10, 170; doi:10.3390/ma10020170 .,Published: Feb. 13, 2017 (Year: 2017).*
Honglei Guo., Glucose-sensitive polyelectrolyte nanocapsules based on layer-by-layer technique for protein drug delivery Springer Science+Business Media New York 2013 (Year: 2013).*
Ramesh N. Patel "Biocatalytic Synthesis of Some Chiral Drug Intermediates by Oxidoreductases"., JAOCS, vol. 74, No. 11 (1997) (Year: 1997).*
Wei Qi., Fabrication of glucose-sensitive protein microcapsules and their applications (Year: 2011).*
Written Opinion of International Search Authority of PCT/IB2017/000683 dated Jun. 8, 2018.
Wang J. et al., "Digital biosensors with built-in logic for biomedical applications-biosensors based on a biocomputing concept", Analytical and Bioanalytical Chemistry, Springer, Berlin, DE, vol. 398, No. 4, May 13, 2010 (May 13, 2010), p. 1591-1603.
Wang J. et al., "Digital Biosensors with Built-in Logic for Biomedical Applications", Israel Journal of Chemistry, vol. 51, No. 1, Jan. 26, 2011 (Jan. 26, 2011), p. 141-150.
Privman M. et al., "Responsive Interface Switchable by Logically Processed Physiological Signals: Toward "Smart" Actuators for Signal Amplification and Drug Delivery", ACS Applied Materials and Interfaces, vol. 3, No. 5, May 25, 2011 (May 25, 2011), p. 1620-1623.
Douglas S. M. et al., "A Logic-Gated Nanorobot for Targeted Transport of Molecular Payloads", Science, vol. 335, No. 6070, Feb. 17, 2012 (Feb. 17, 2012), p. 831-834.
Rai M. et al., "Biomedical applications of nanobiosensors: the state-of-the-art", Journal of the Brazilian Chemical Society, vol. 23, No. 1, Jan. 1, 2012 (Jan. 1, 2012), p. 14-24.
Jain K. K., "Applications of Nanobiotechnology in Clinical Diagnostics", Clinical Chemistry, vol. 53, No. 11, Sep. 21, 2007 (Sep. 21, 2007), p. 2002-2009.
Astier Y. et al., "Protein components for nanodevices", Dec. 1, 2005 (Dec. 1, 2005), vol. 9, No. 6, p. 576-584.
Miller D. M. et al., "Engineering Protocells: Prospects for Self-Assembly and Nanoscale Production-Lines", Life, vol. 5, No. 2, Mar. 25, 2015 (Mar. 25, 2015), p. 1019-1053.
Courbet A. et al., "Detection of pathological biomarkers in human clinical samples via amplifying genetic switches and logic gates", Science Translational Medicine, vol. 7, No. 289, May 27, 2015 (May 27, 2015), p. 289ra83.
Patolsky F. et al., "Nanowire-based nanoelectronic devices in the life sciences", MRS Bull, Pittsburgh, US, vol. 32, No. 2, Feb. 1, 2007 (Feb. 1, 2007), p. 142-149.
Hajba L. et al., "The use of magnetic nanoparticles in cancer theranostics: Toward handheld diagnostic devices", Biotechnology Advances, Elsevier Publishing, Barking, GB, vol. 34, No. 4, Feb. 4, 2016 (Feb. 4, 2016), p. 354-361.
Ghafar-Zadeh E., "Wireless Integrated Biosensors for Point-of-Care Diagnostic Applications", Sensors, vol. 15, No. 2, Feb. 2, 2014 (Feb. 2, 2014), p. 3236-3261.
Von Maltzahn G. et al., "Nanoparticle Self-Assembly Gated by Logical Proteolytic Triggers", Journal of the American Chemical Society, vol. 129, No. 19, May 1, 2007 (May 1, 2007), p. 6064-6065.
Aykawaya et al. "RTRACS: A Modularized RNA-Dependant RNA Transcription System with High Programability", Accounts of Chemical Research vol. 44 No. 11, (2011) , 1369-1379.
Courbet et al. "Computing with synthetic protocells", Acta Biother (2015) 63:(309-323).
International Search Report of PCT/IB2017/000683, dated May 8, 2018.

\* cited by examiner

Figure 3A:
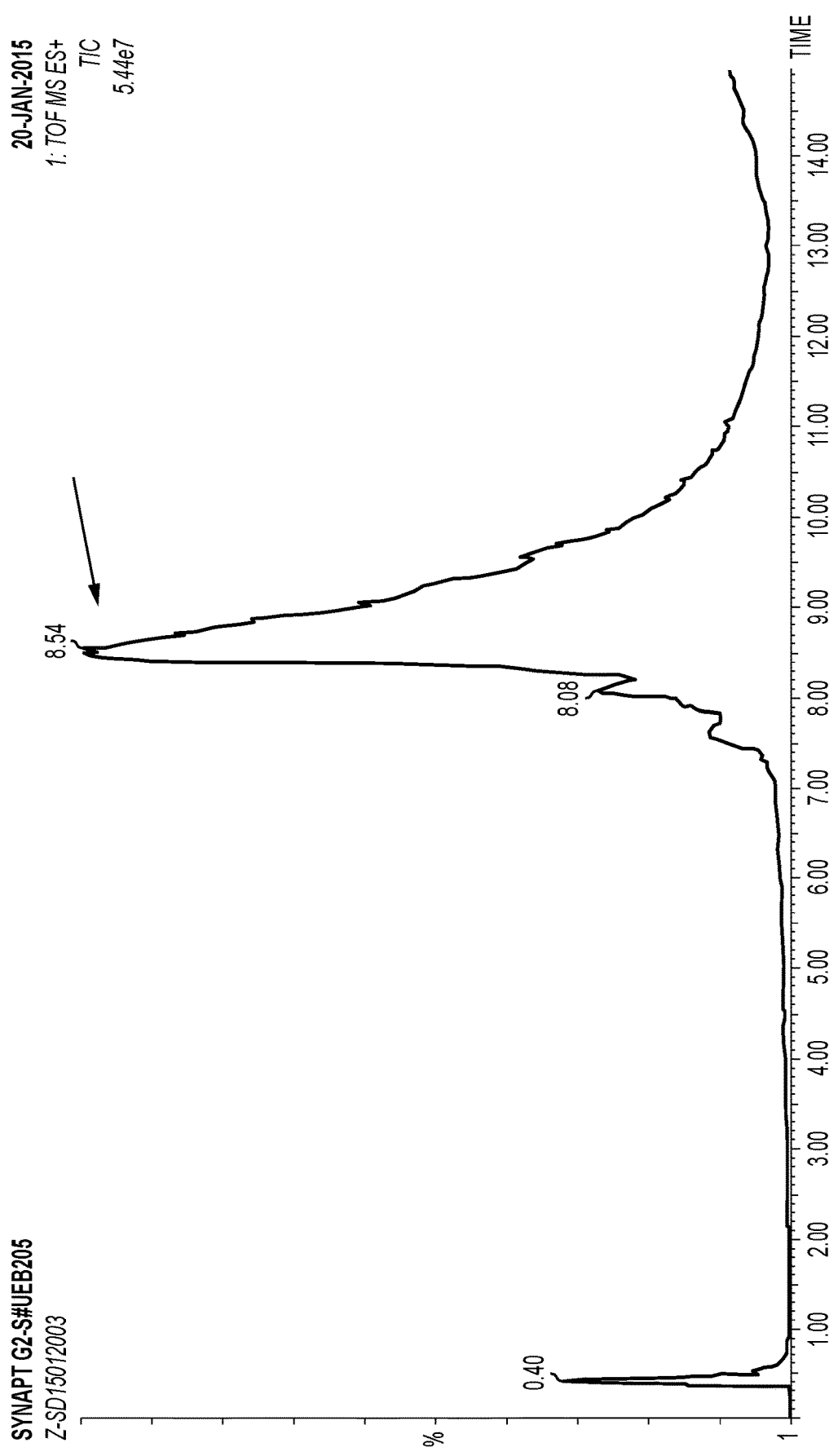
Figure 3A:
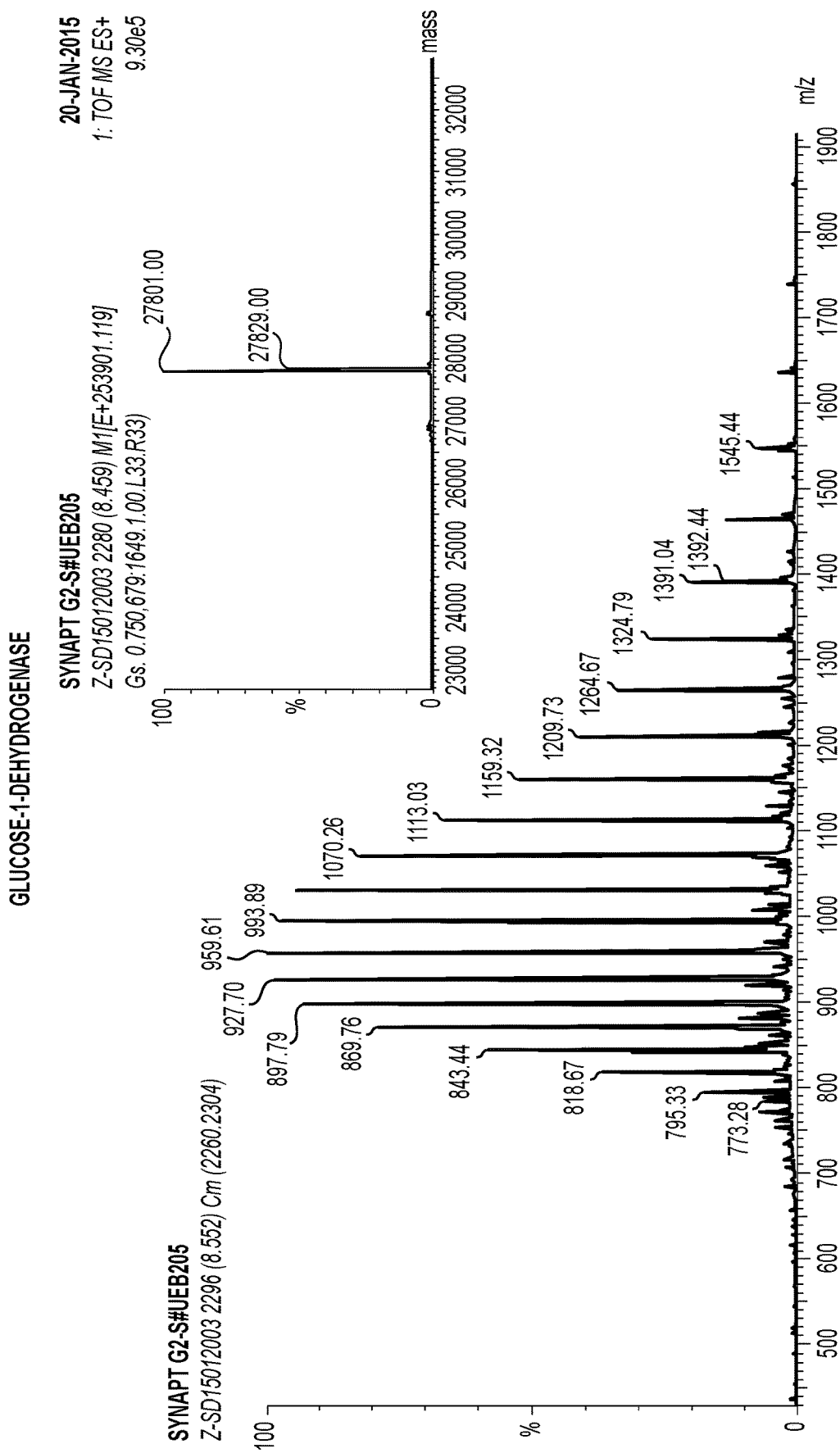
Figure 3B:
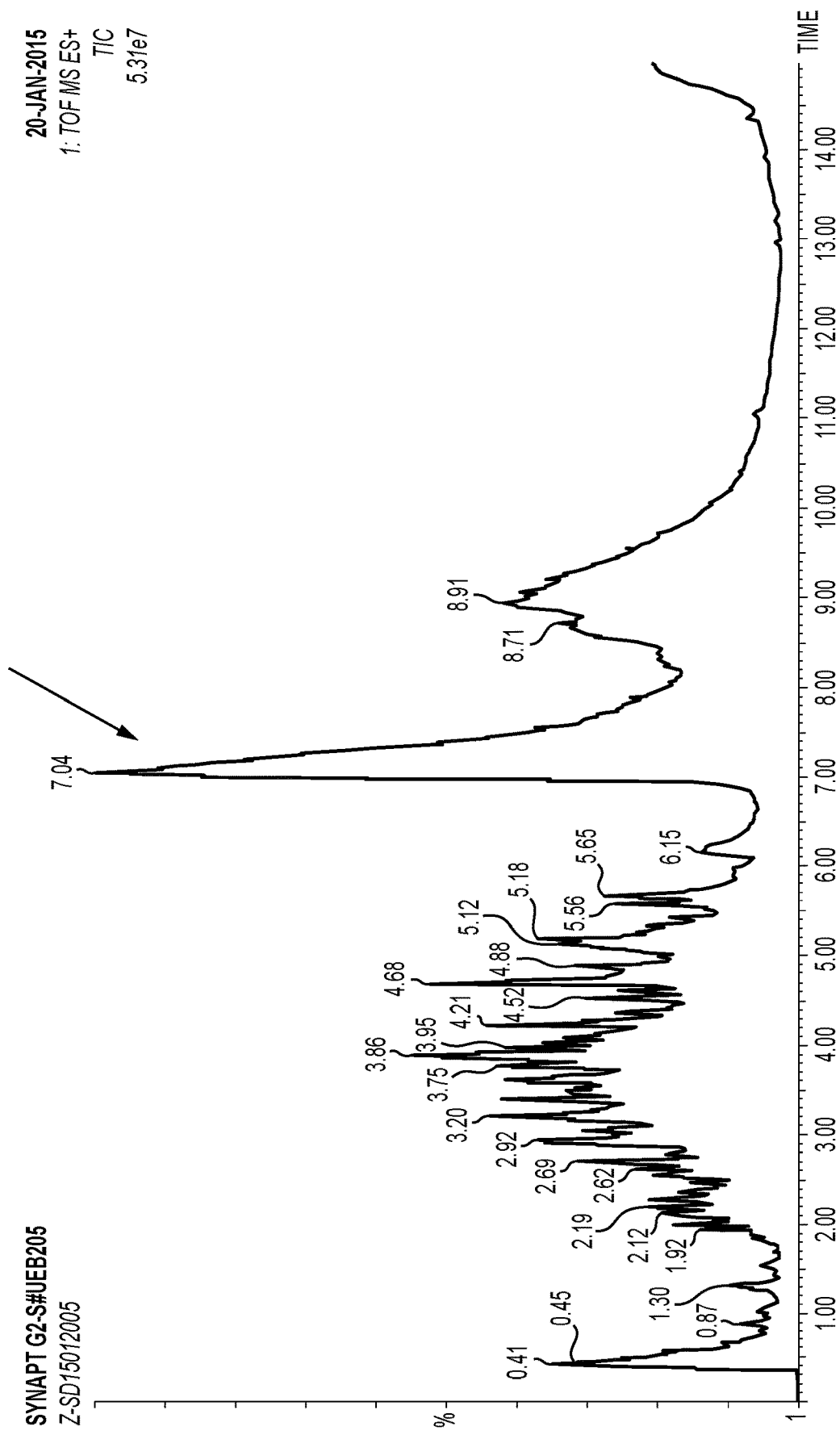
Figure 3B:
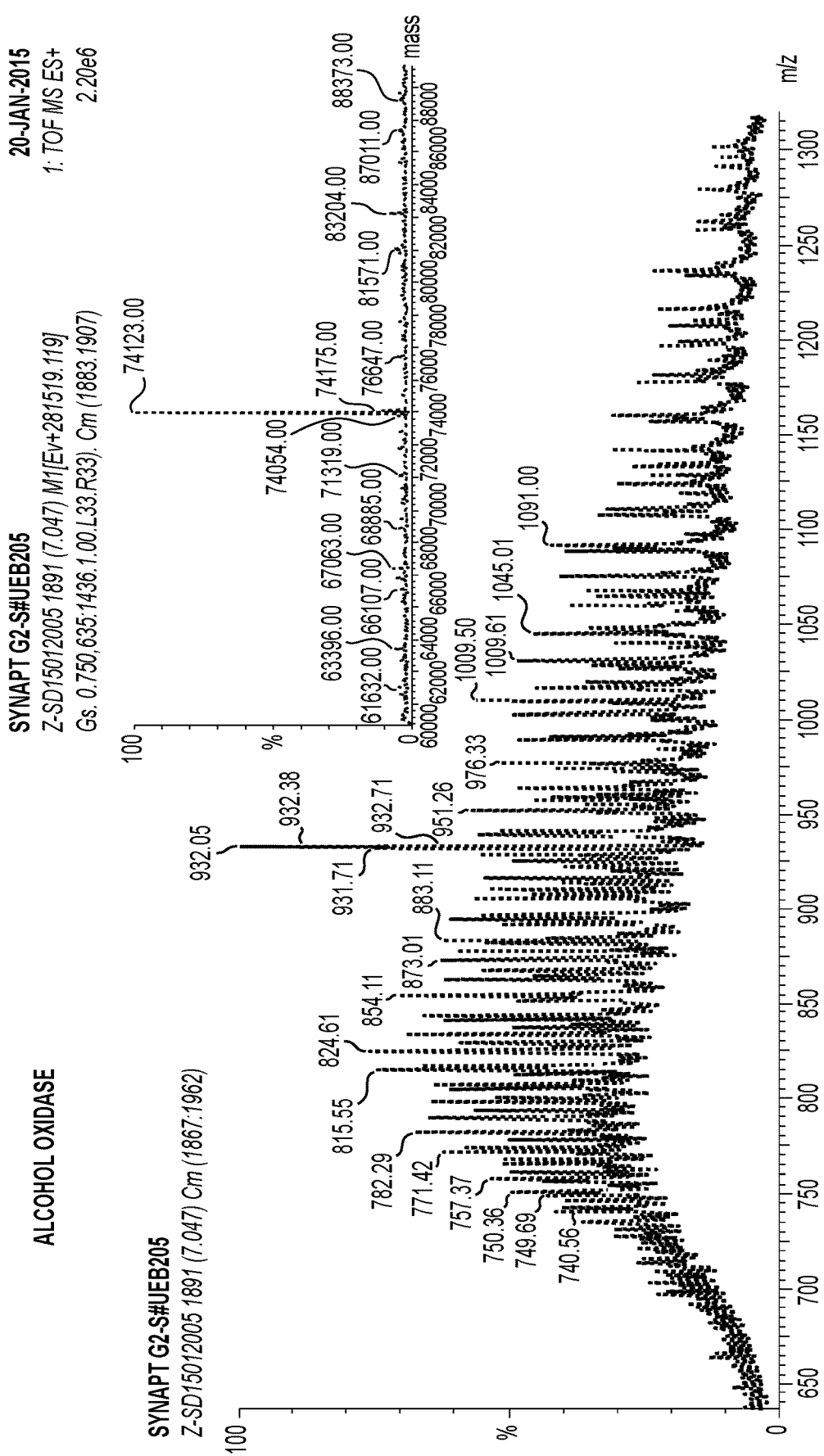
Figure 3C:
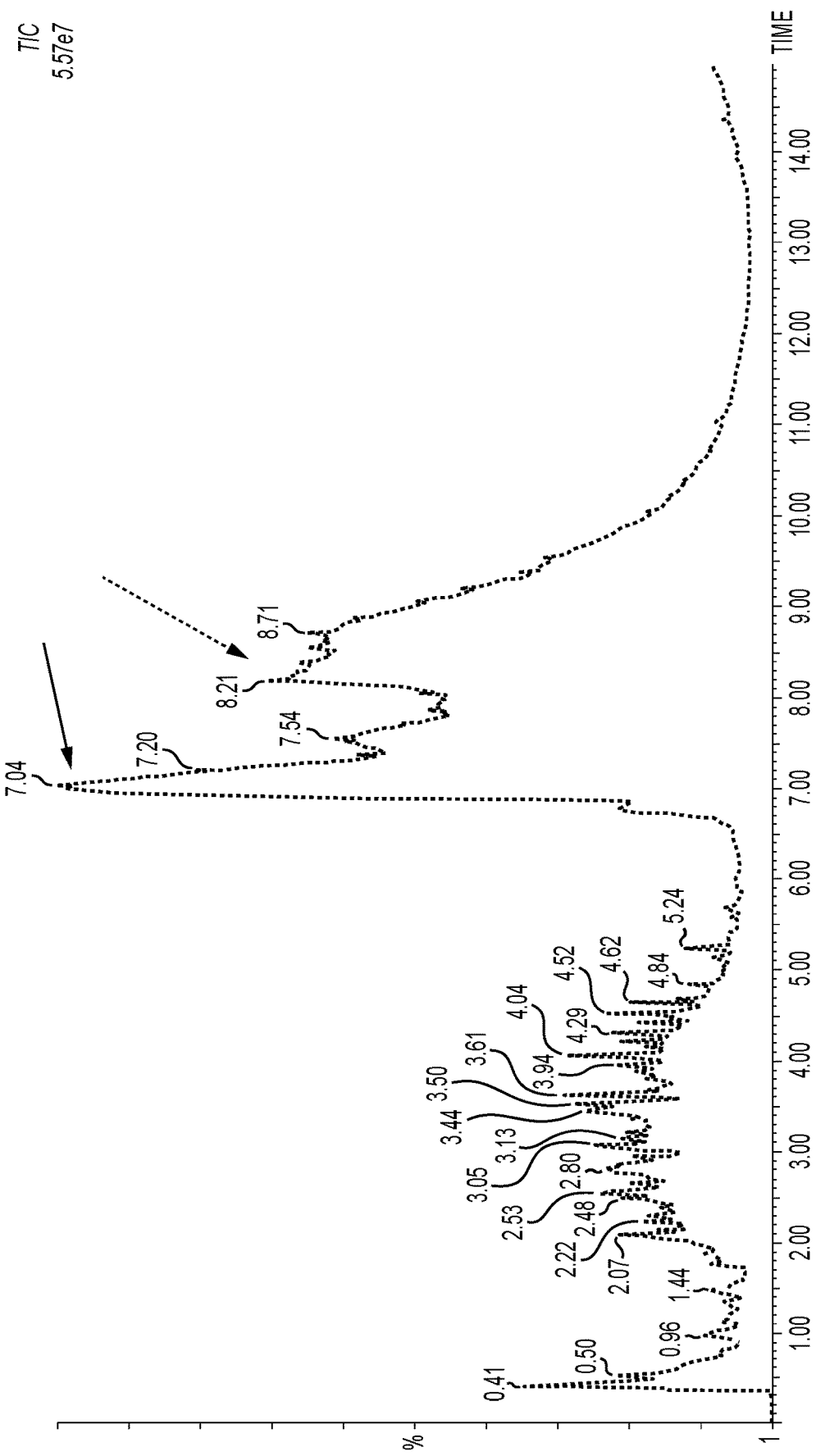
Figure 3C:
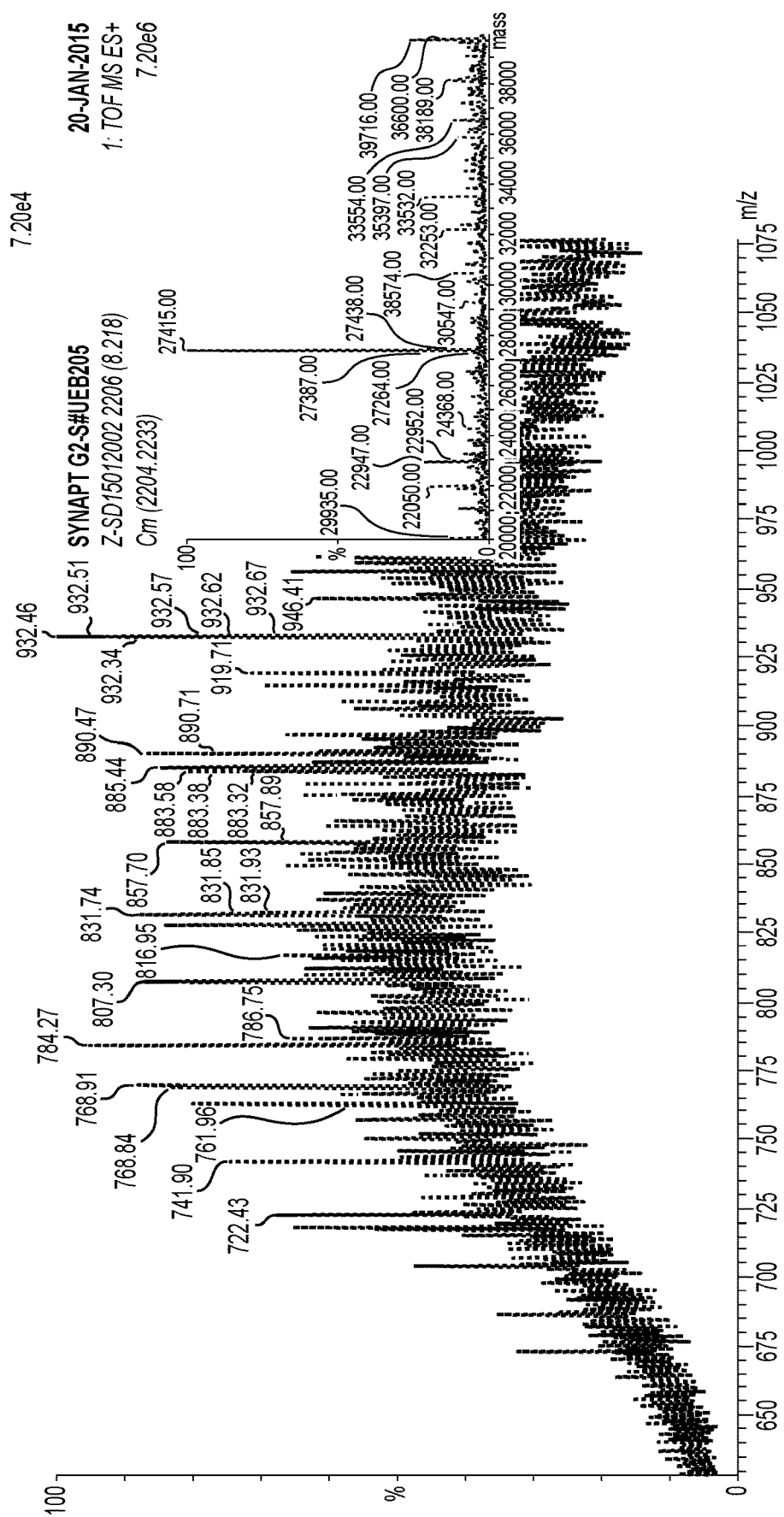

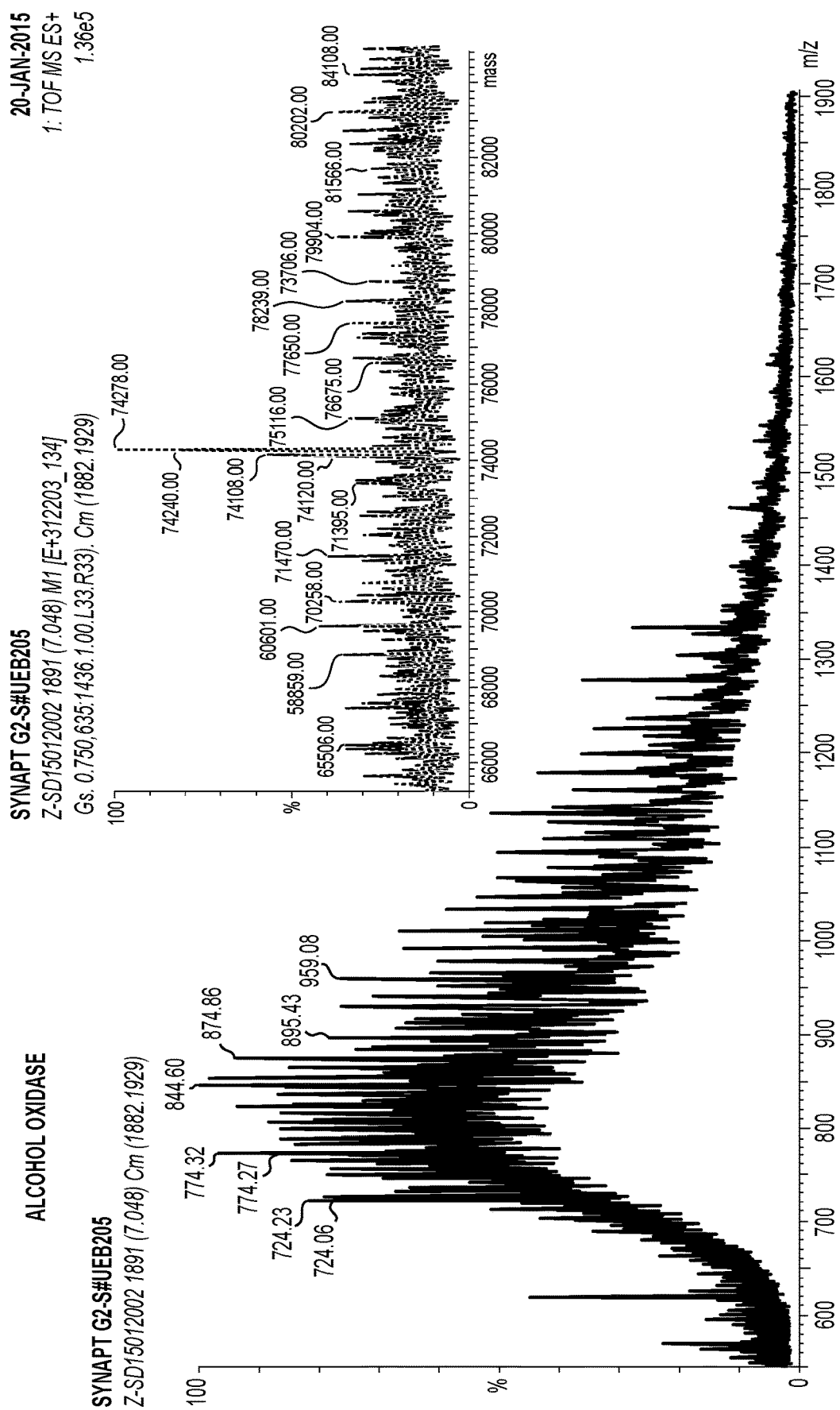
FIG. 3C (CONT.1)

Figure 9:
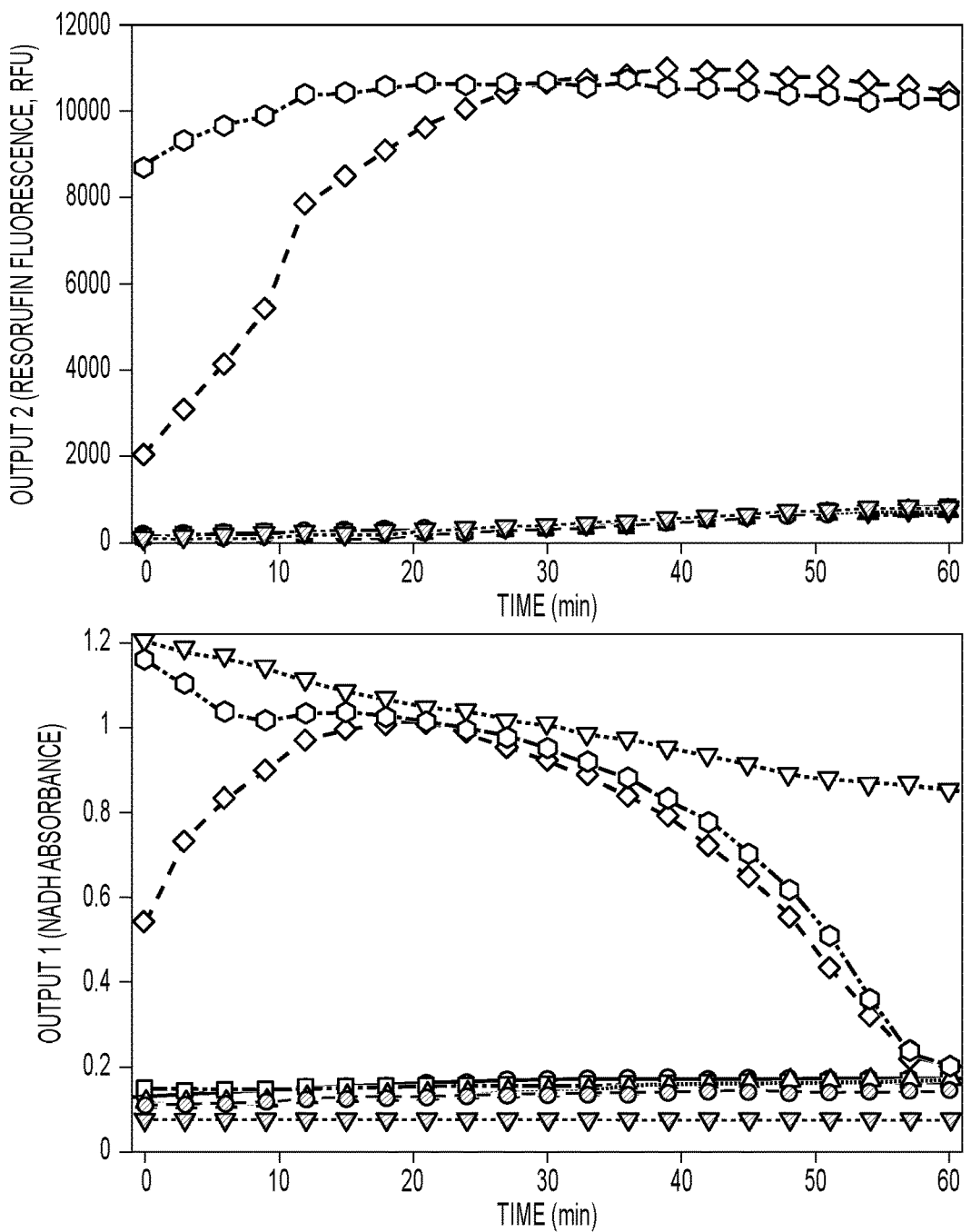

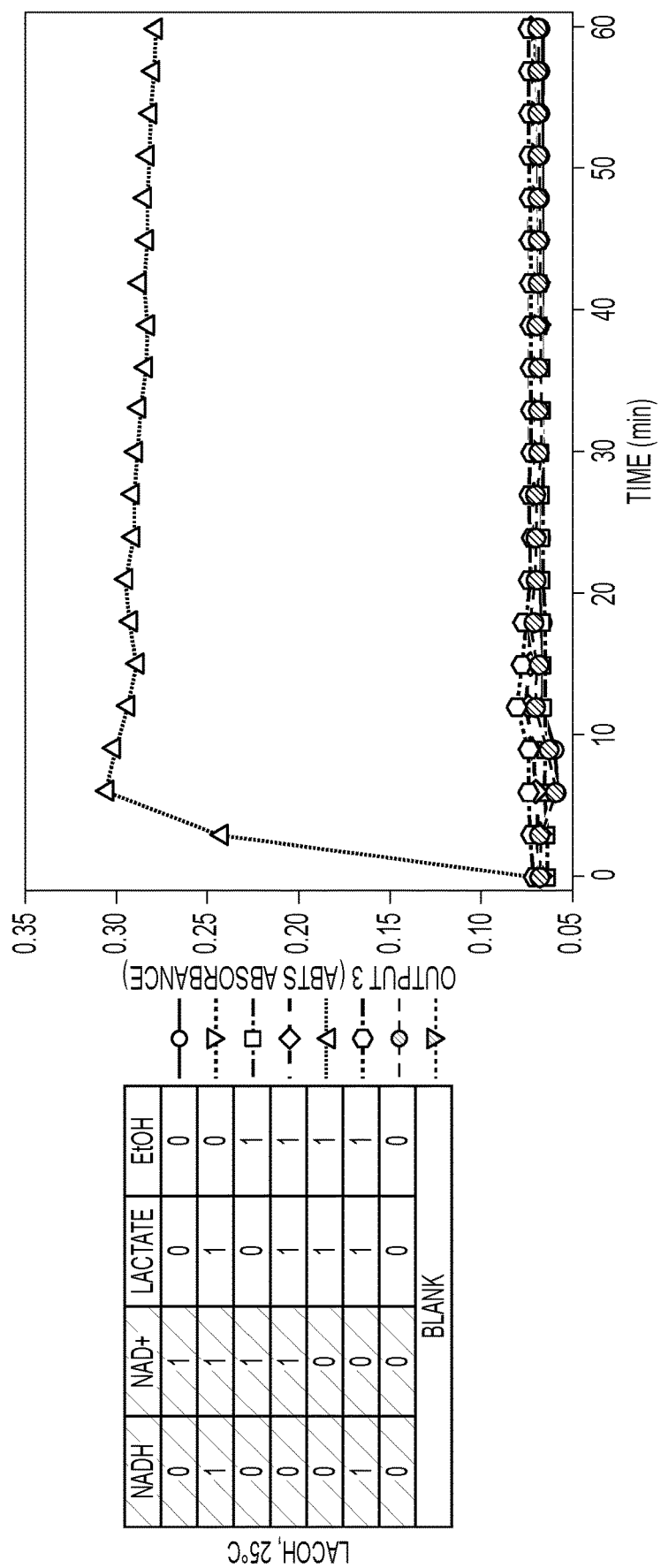
FIG. 9 *(CONT.)*

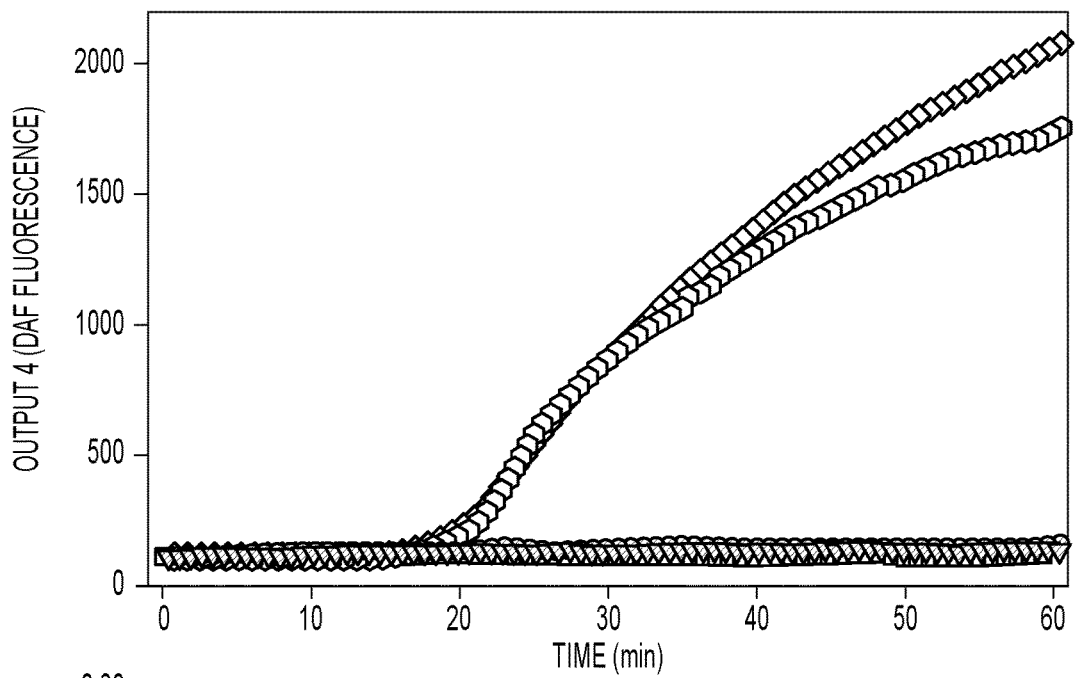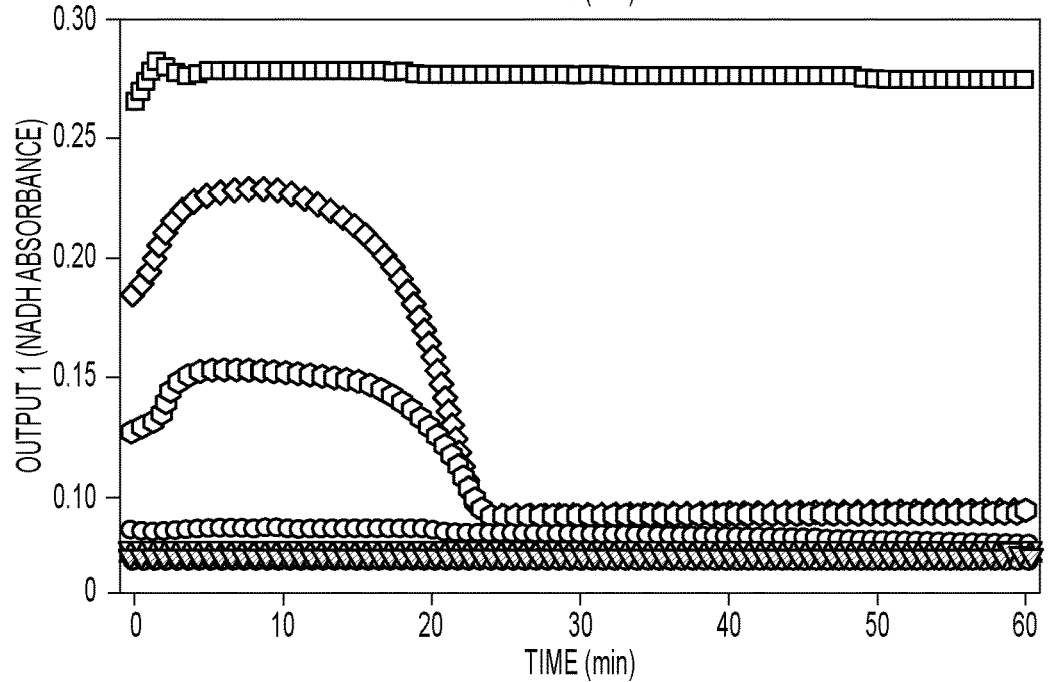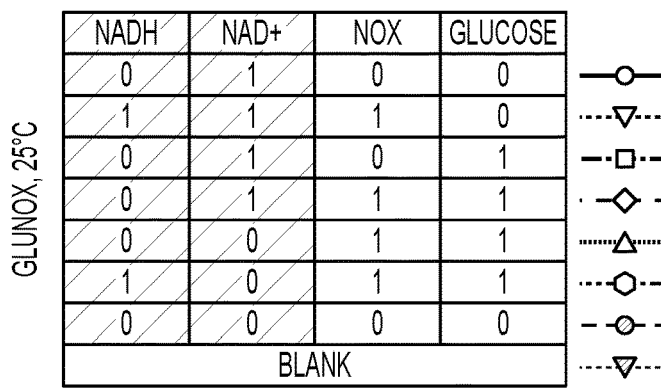
FIG. 9 (CONT.1)

Figure 10:
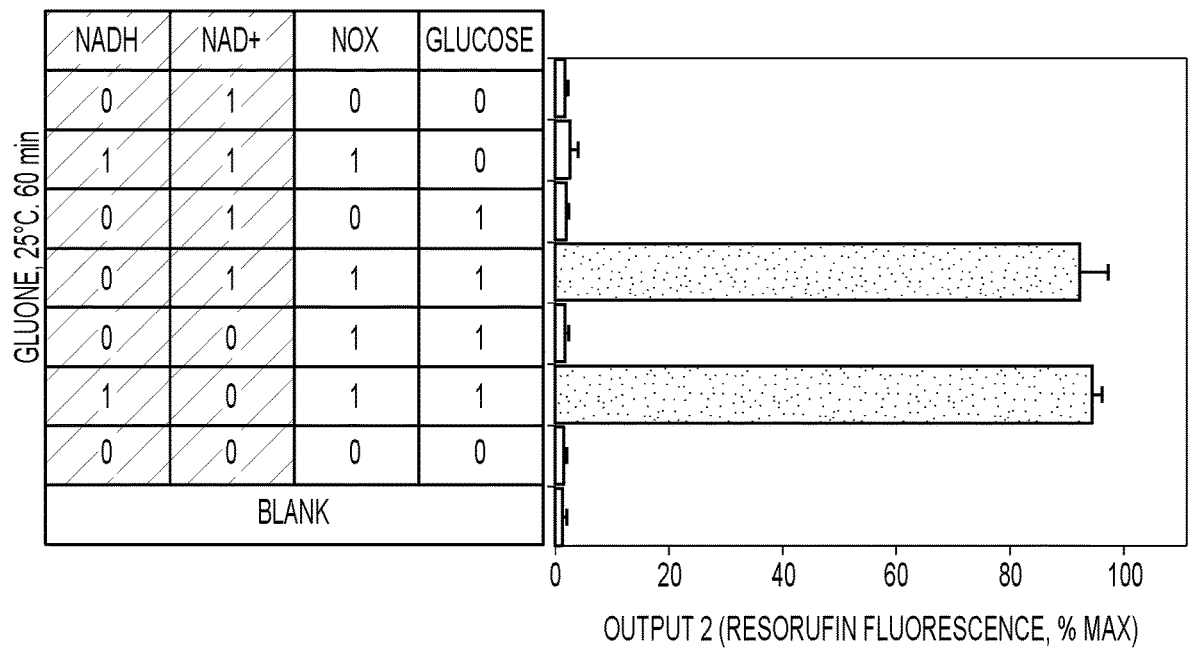
Figure 10:
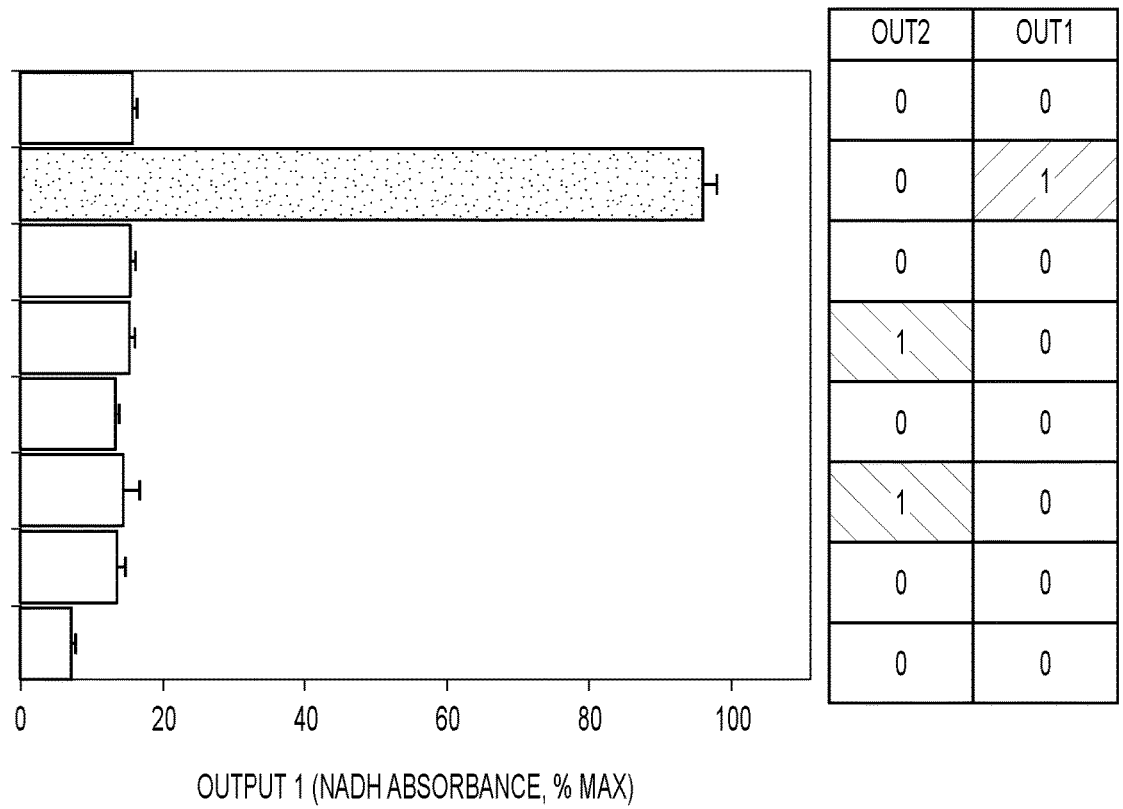
Figure 10:
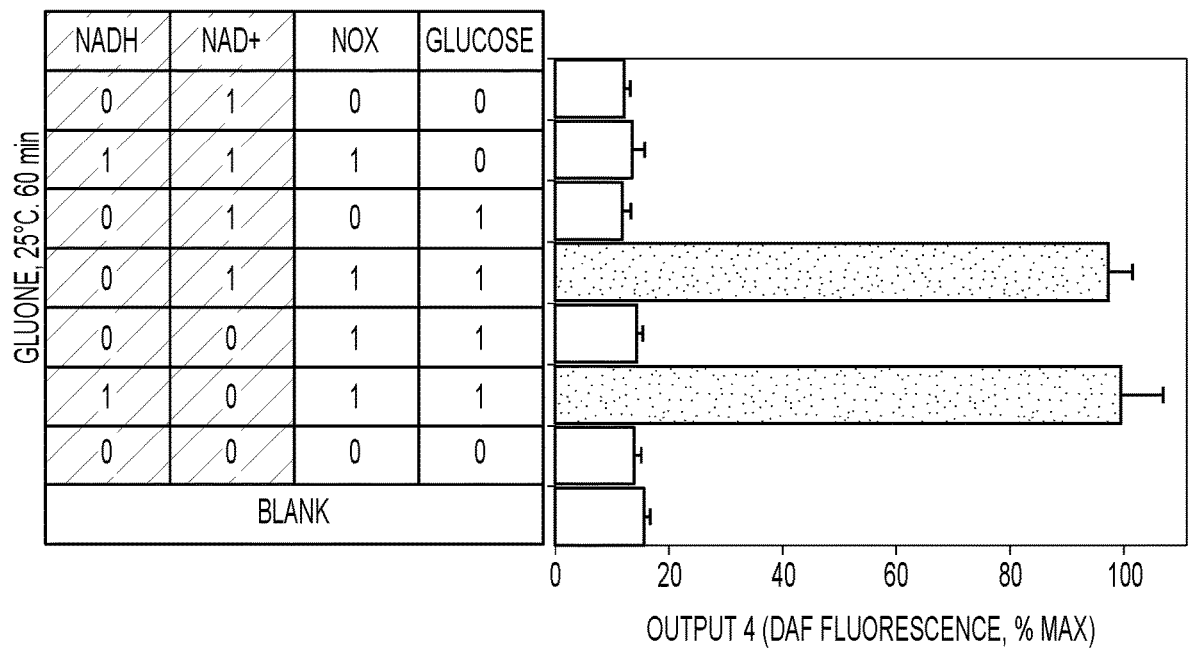
Figure 10:
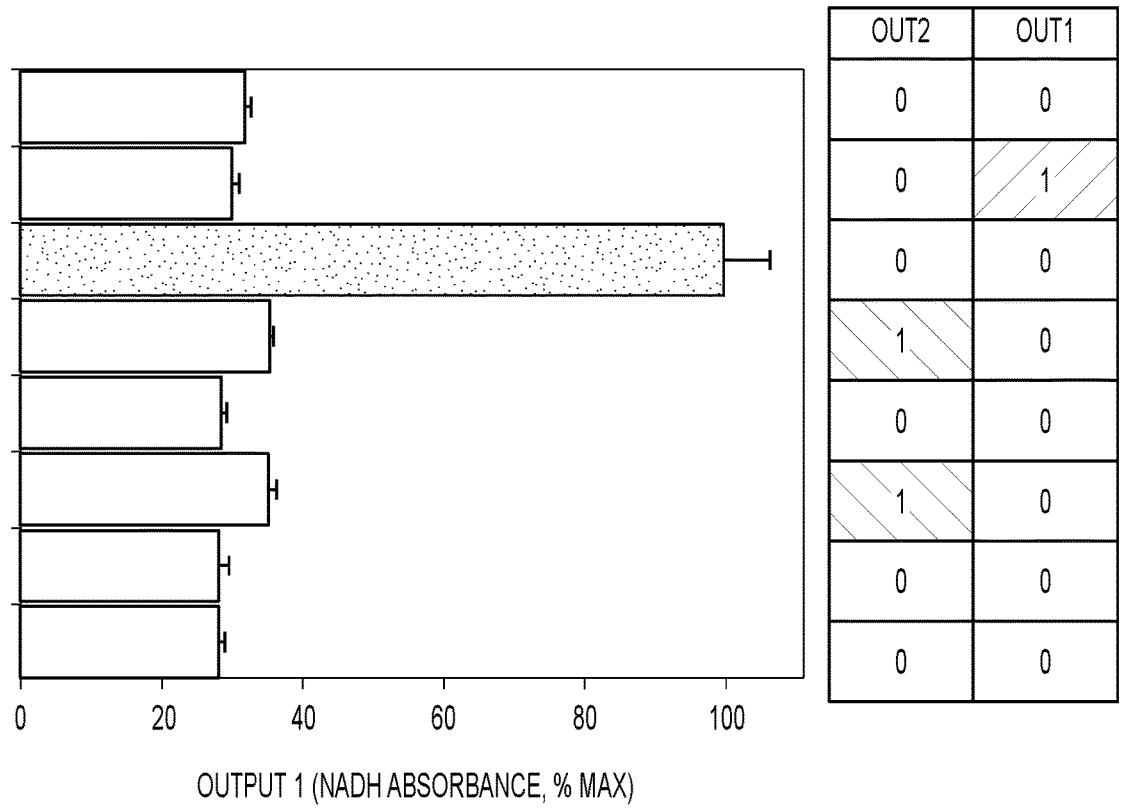

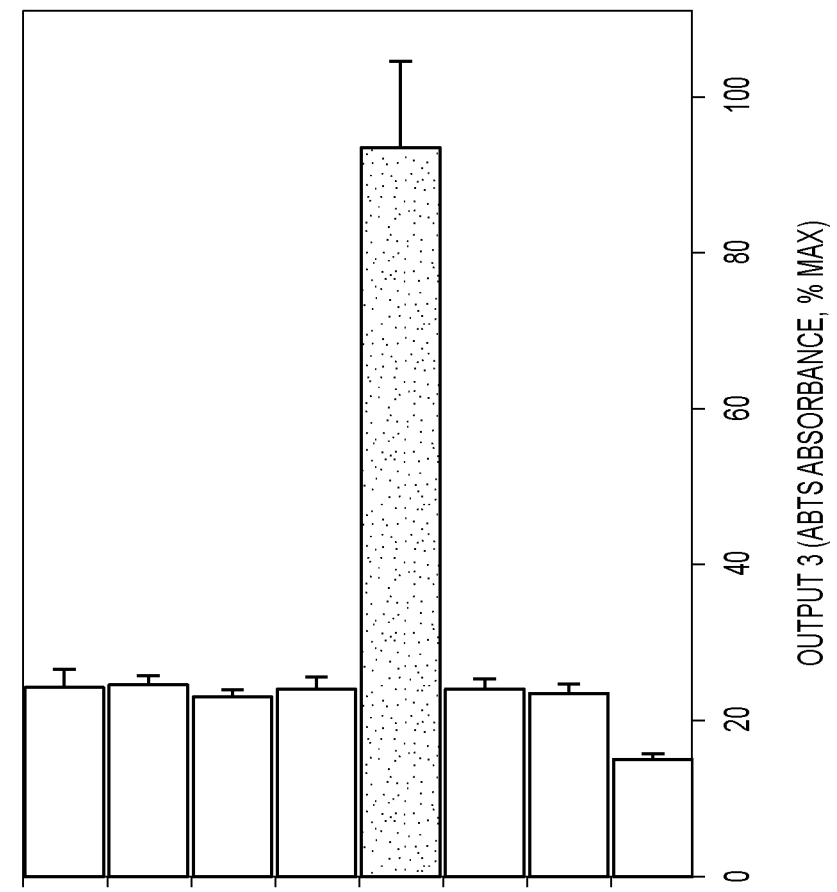
FIG. 10 *(CONT.)*

*(CONT.1)*

Model equations:
$d[A]/dt = P1[A^*]$
$d[B]/dt = P2[B^*]$
$d[A]/dt = -k1[E][A] + k2[EA]$
$d[C]/dt = k5[EAB]$
$d[E]/dt = -k1[E][A] + k2[EA]$
$d[B]/dt = -k3[EA][B] + k4[EAB]$
$d[D]/dt = k6[ED]$
$d[EA]/dt = k1[E][A] - k2[EA] - k3[EA][B]$
$d[EAB]/dt = k3[EA][B] - k4[EAB] - K5[EAB]$
$d[ED]/dt = k5[EAB] - k6[ED]$

Parameters:
Initial concentrations
$ki$: reaction rate constants
$Pi$: the rate of transport in/out $$dX/dt = F(N, t; \theta)$$

Figure 21A:
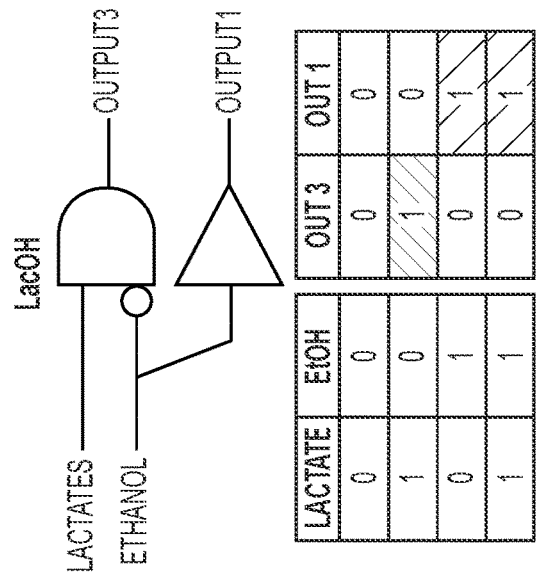
Figure 21A:
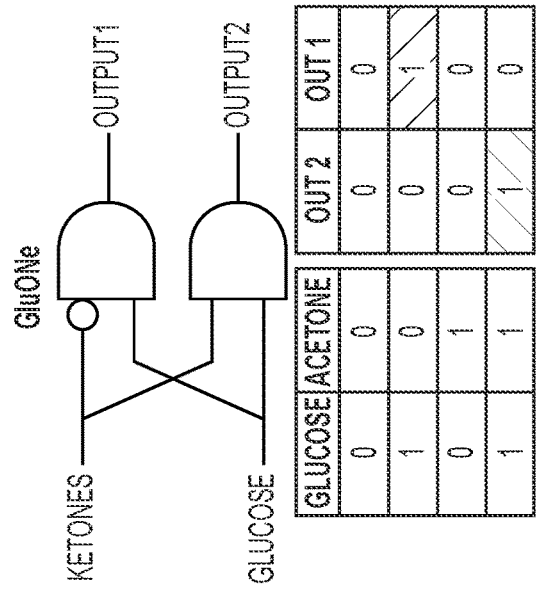
Figure 21A:
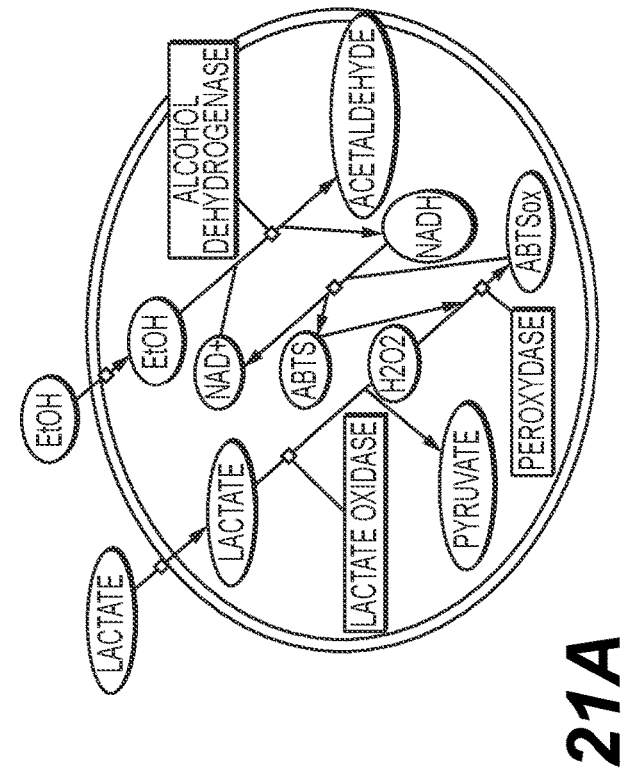
Figure 21A:
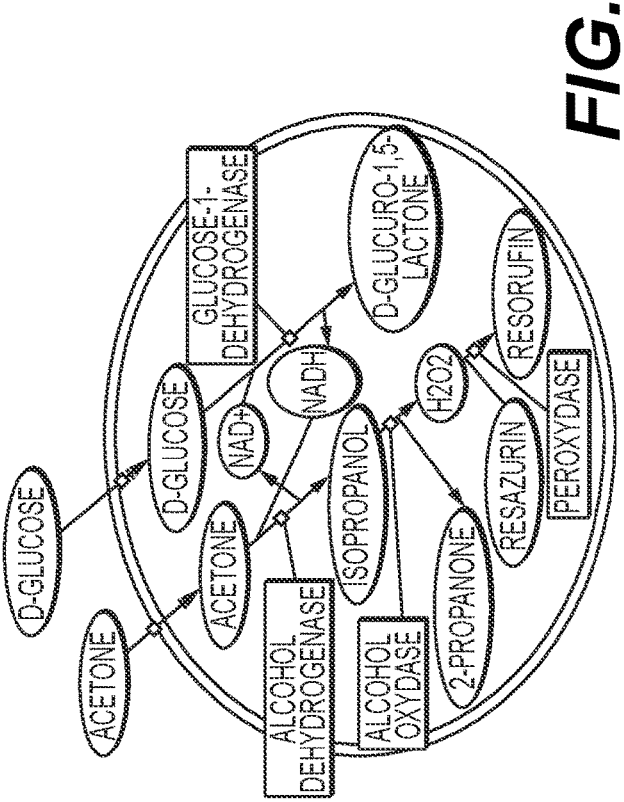
Figure 21A:
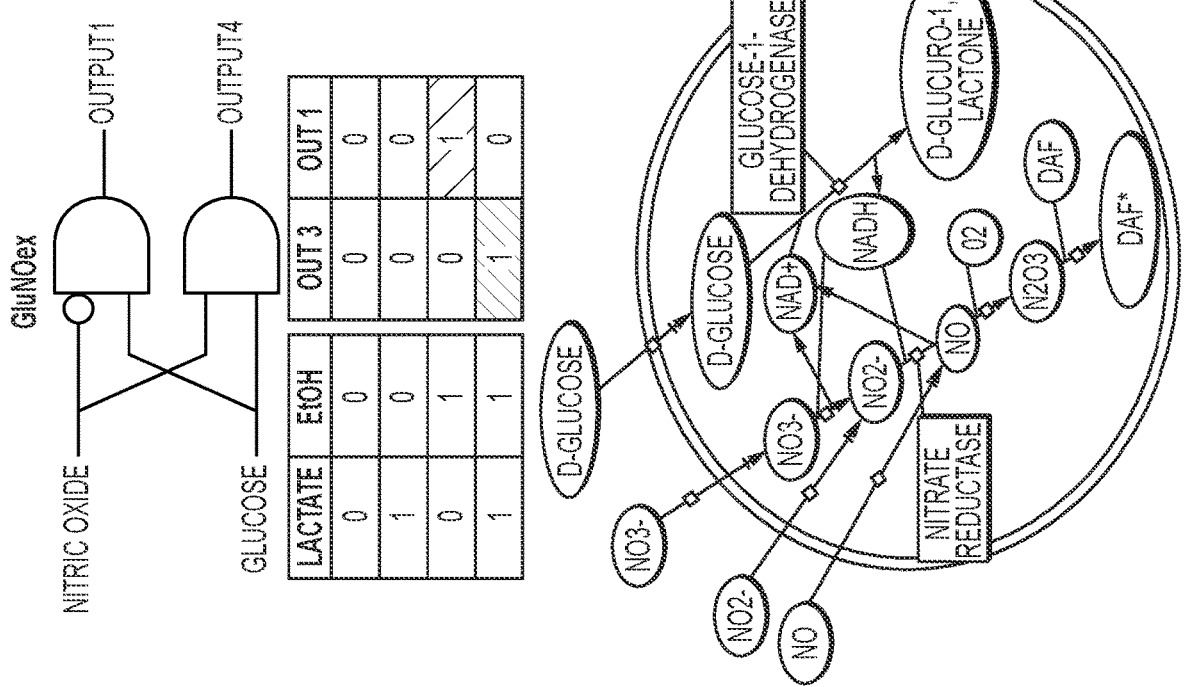
Figure 21B:
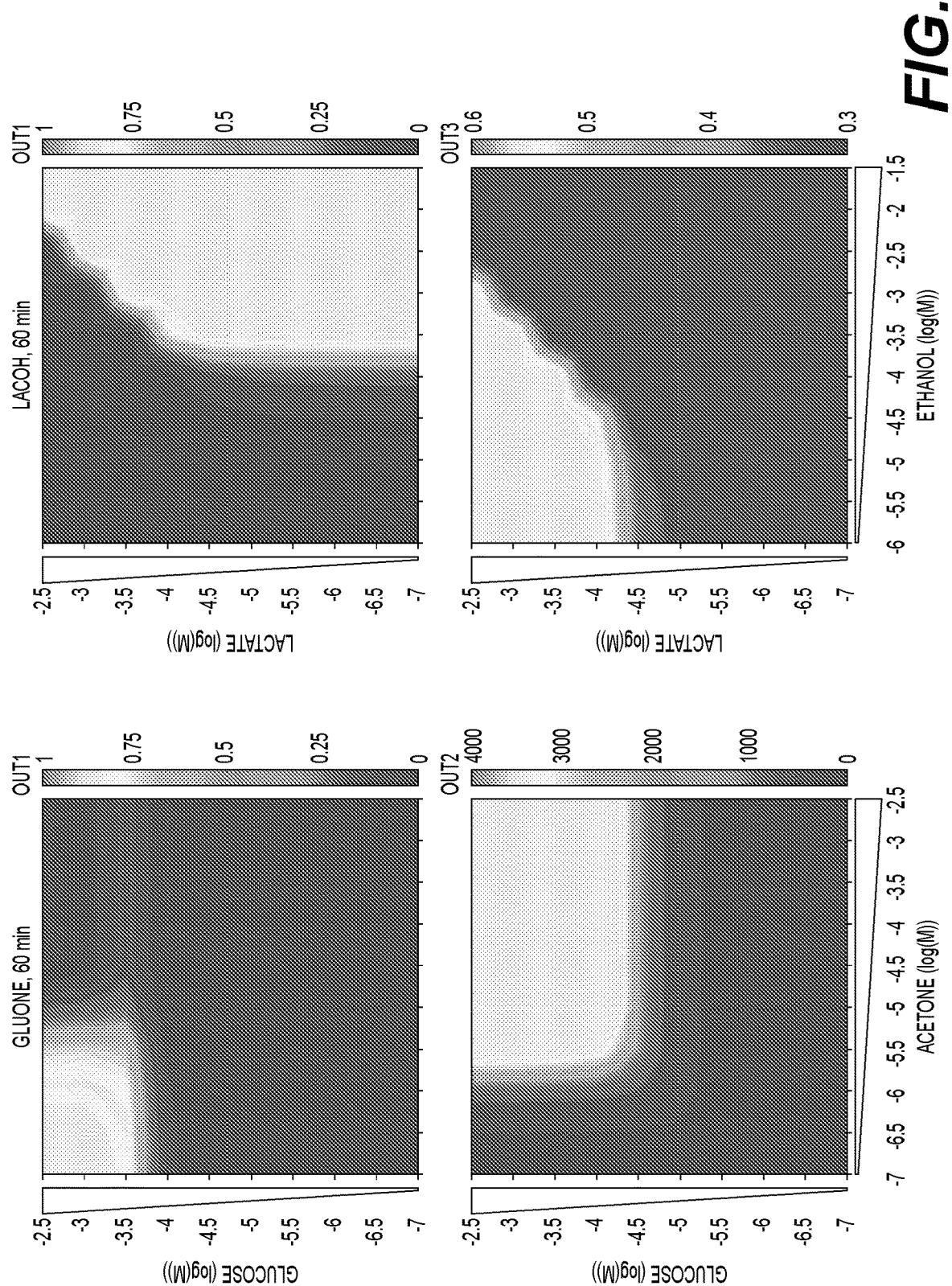
Figure 21B:
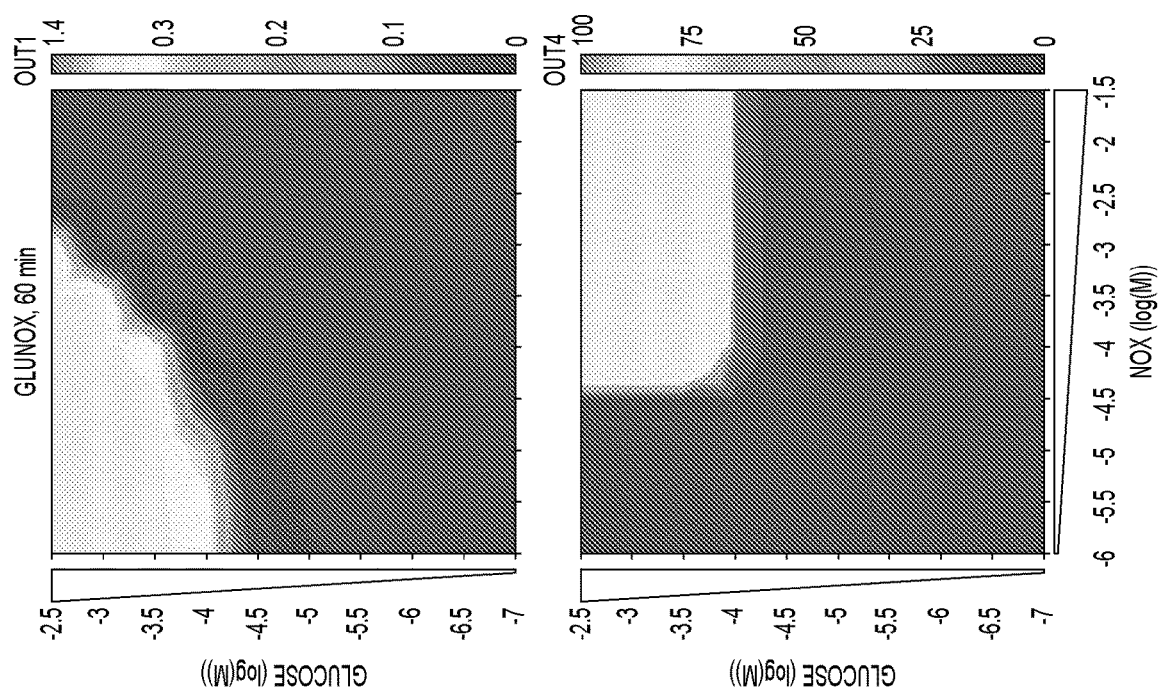
Figure 21C:
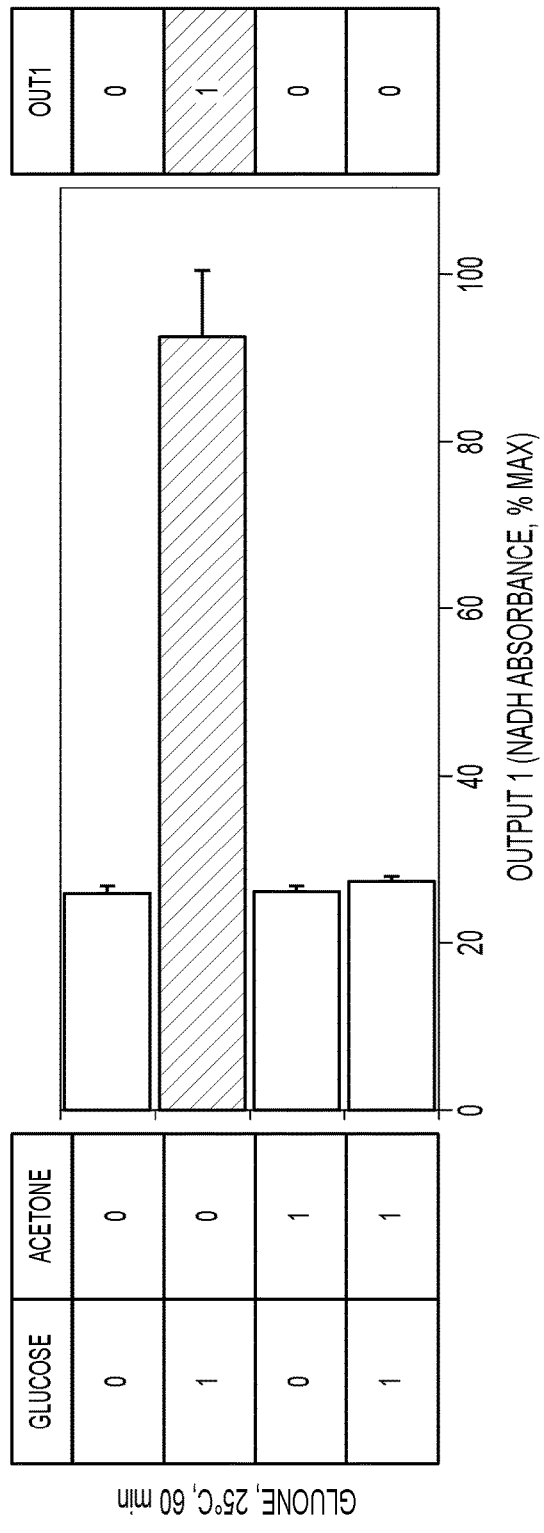
Figure 21C:
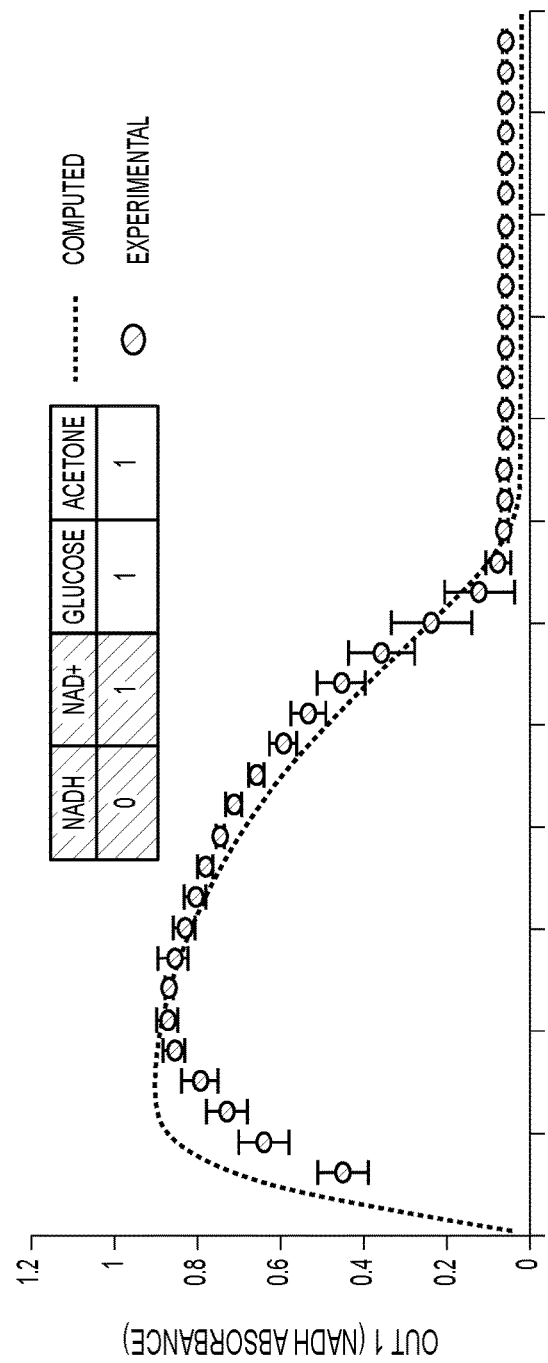
Figure 21C:
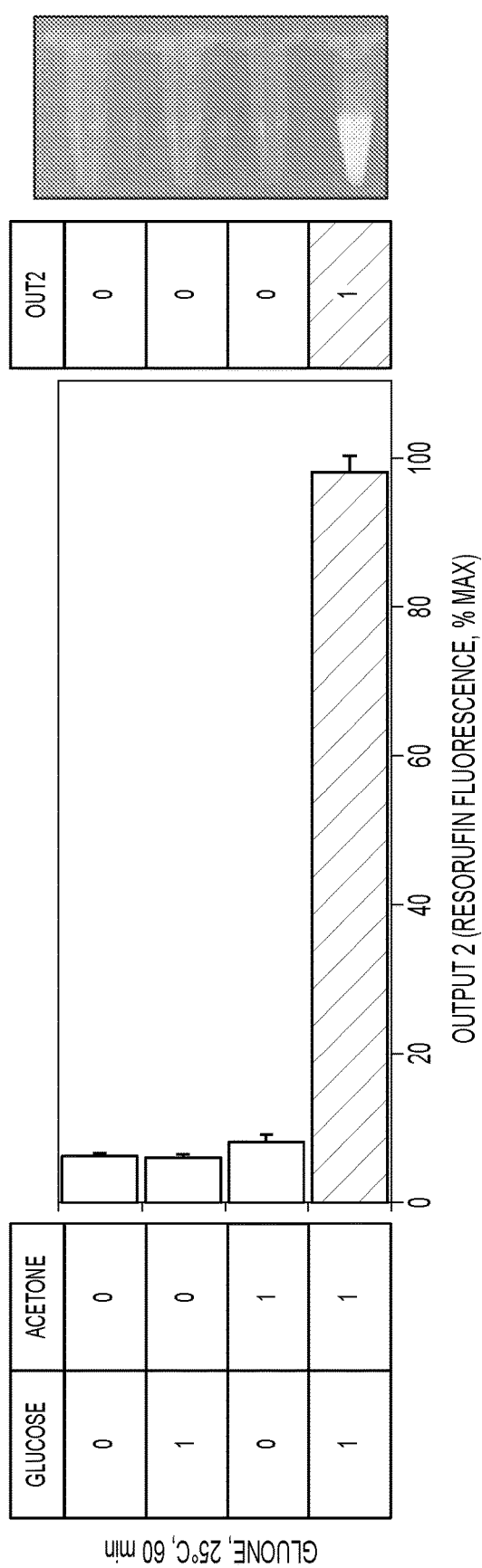
Figure 21C:
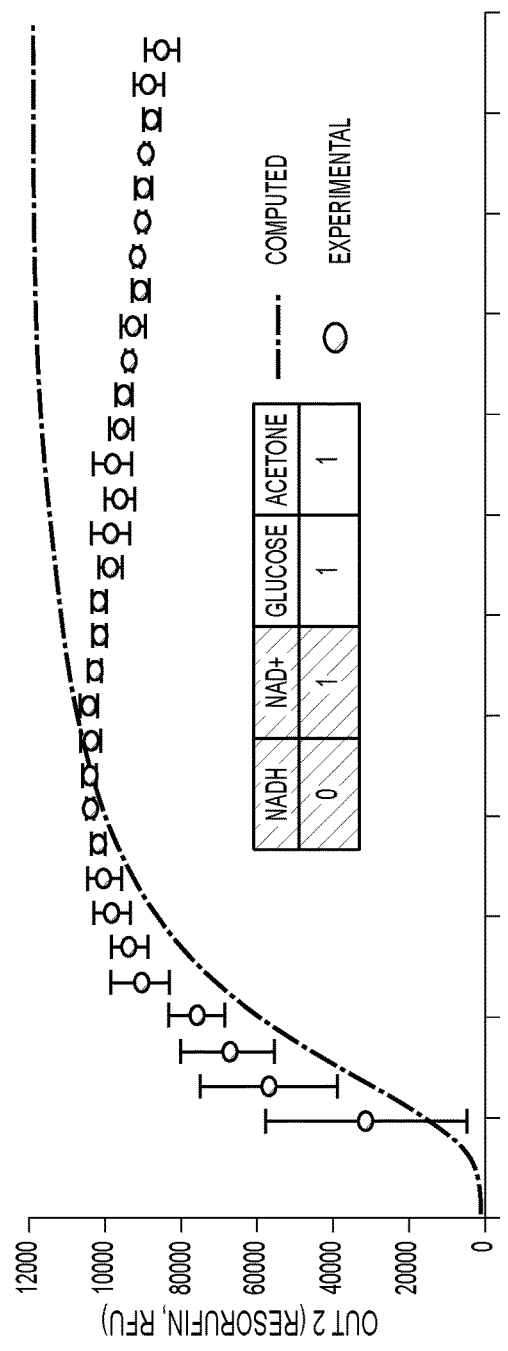

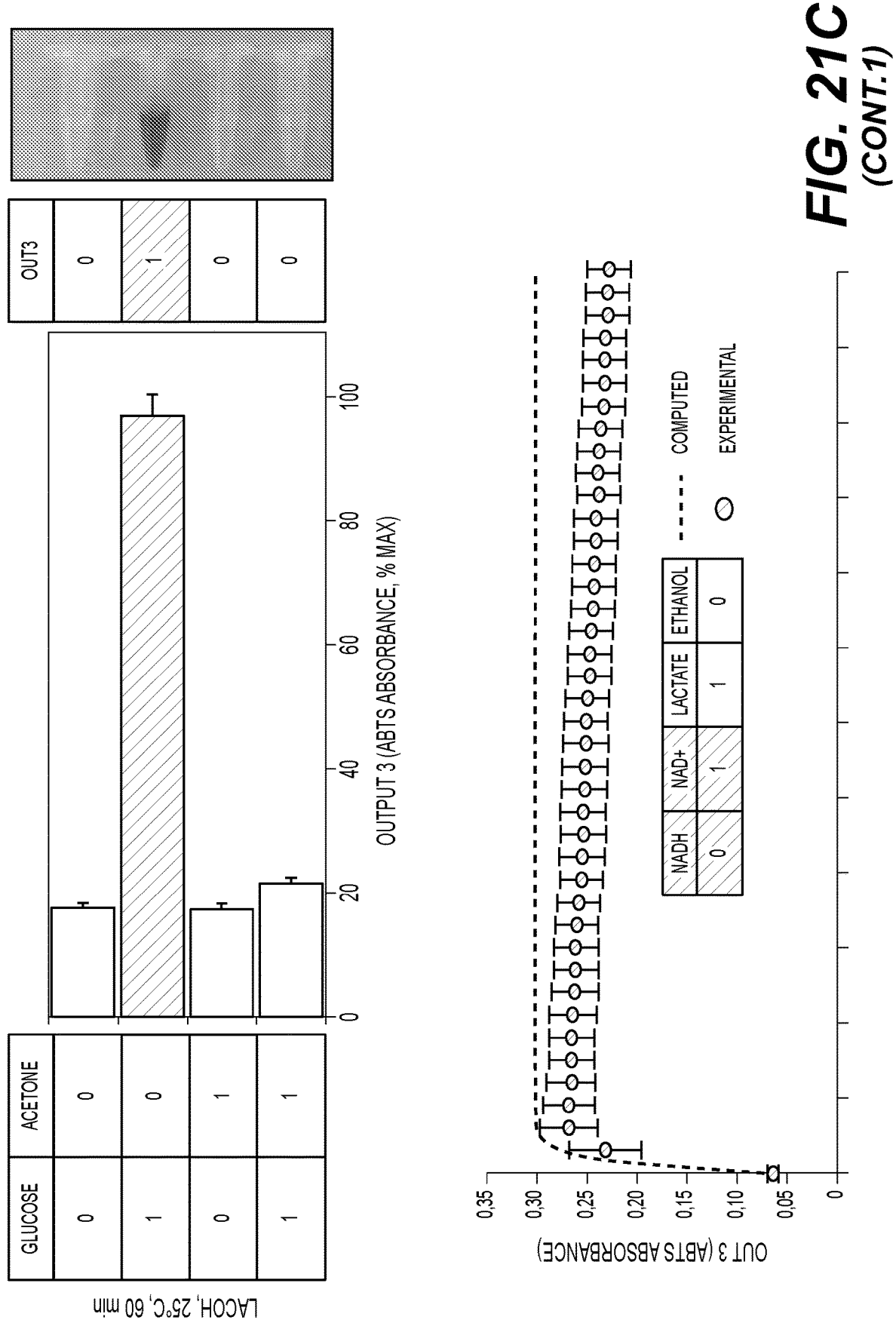
FIG. 21C (CONT.1)

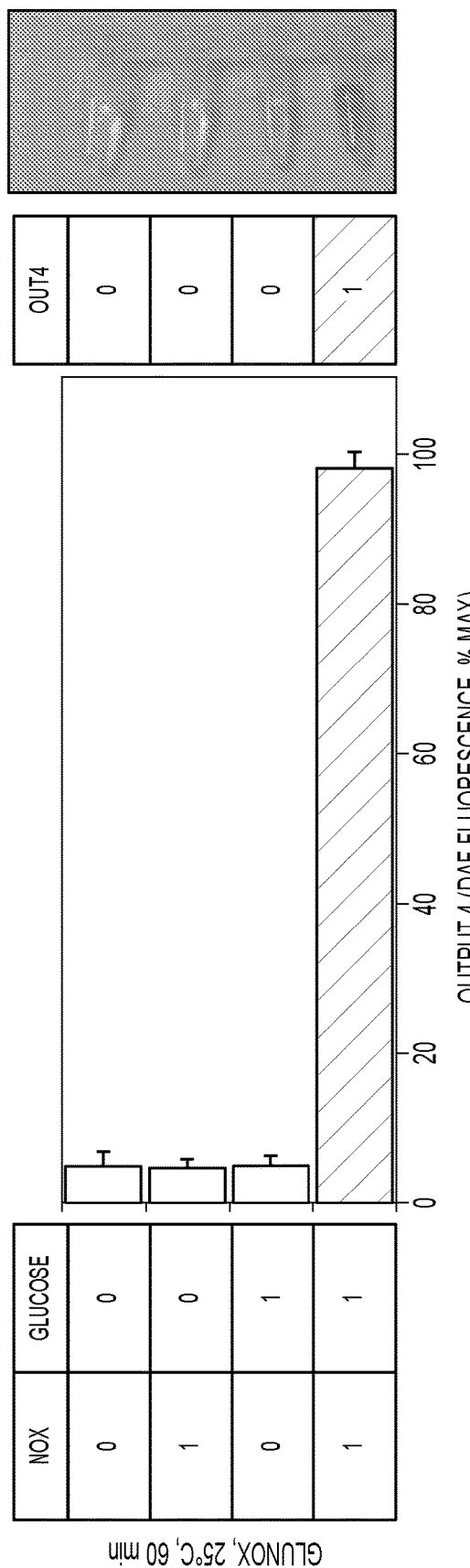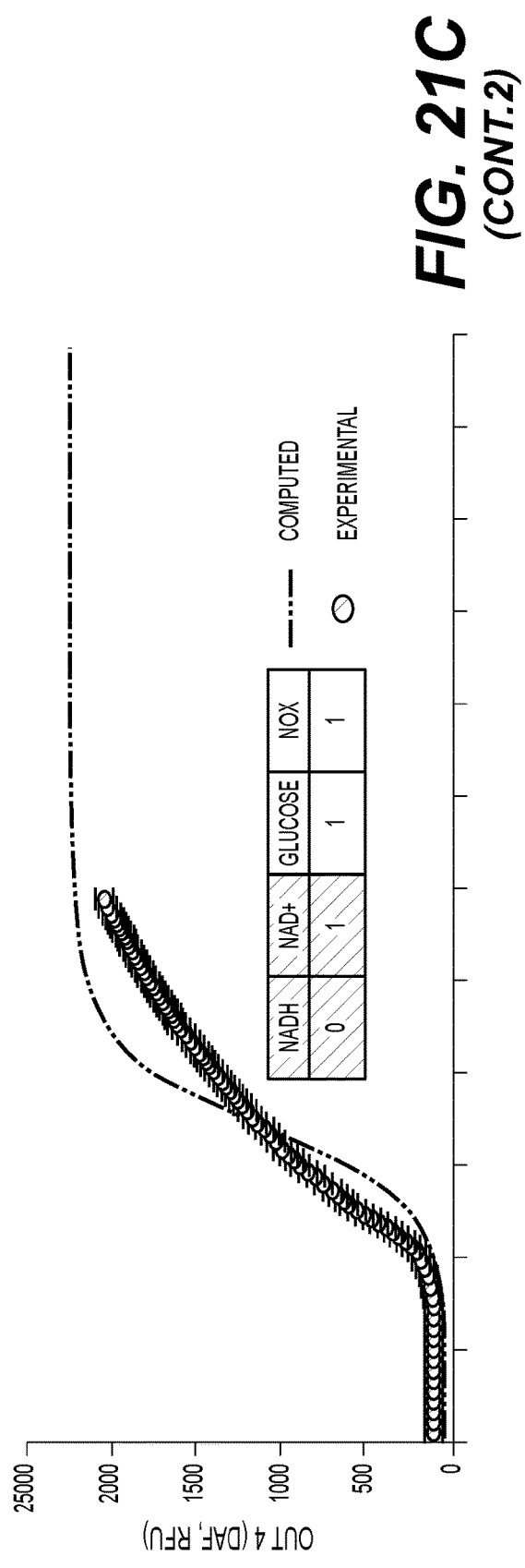
FIG. 21C (CONT.2)

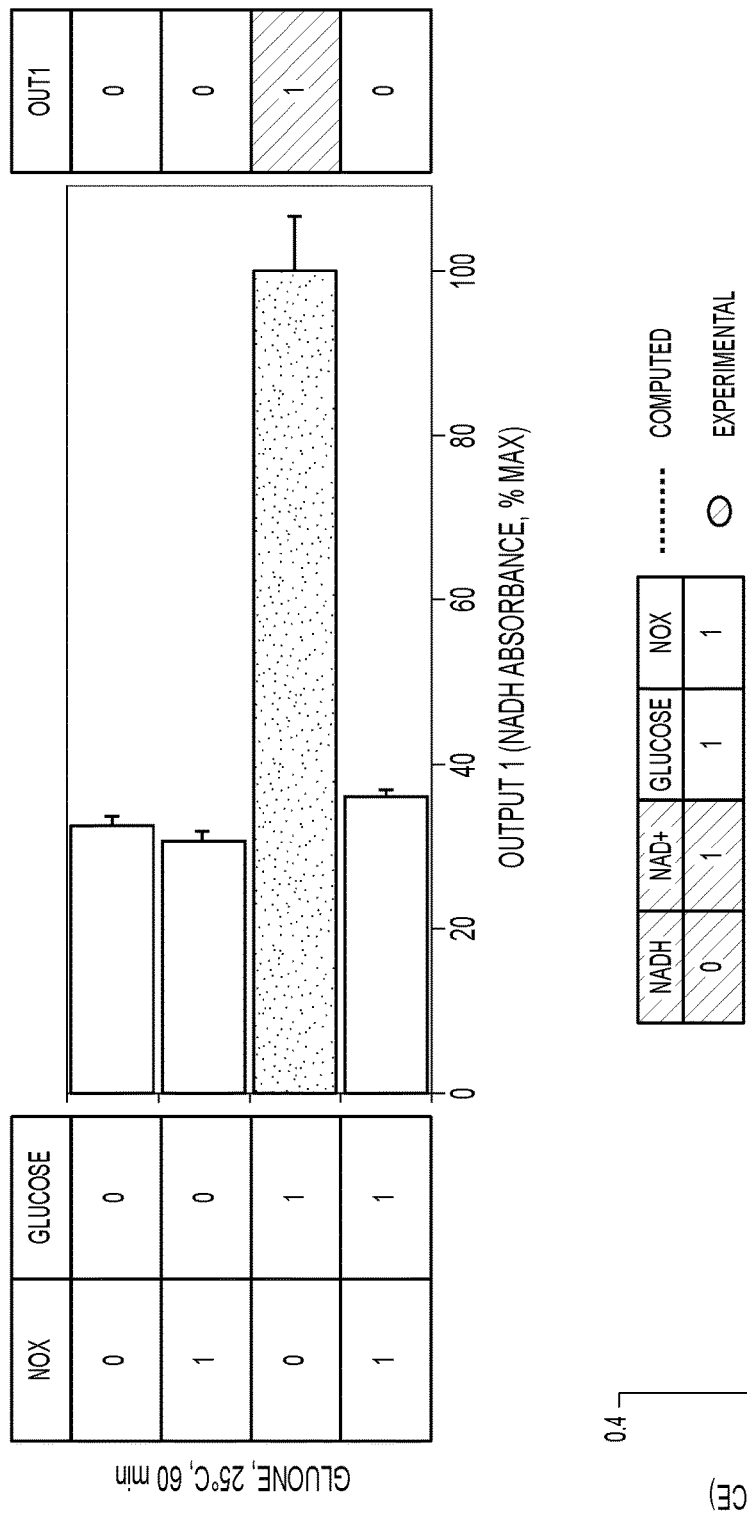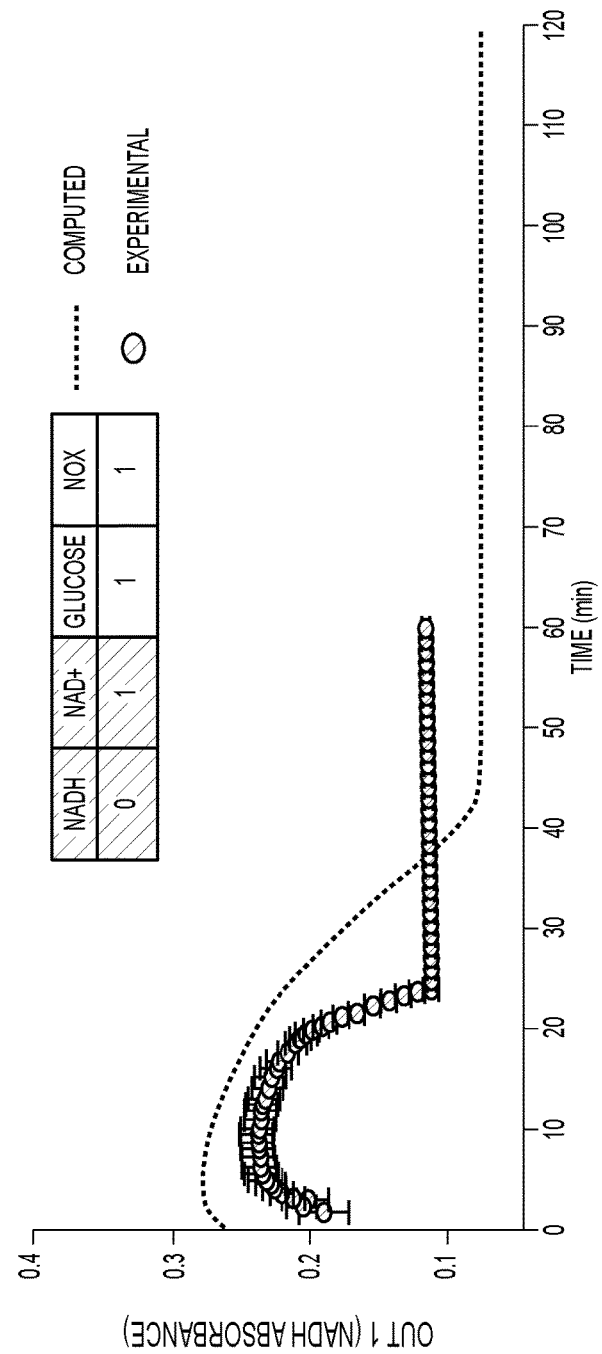
FIG. 21C (CONT.3)

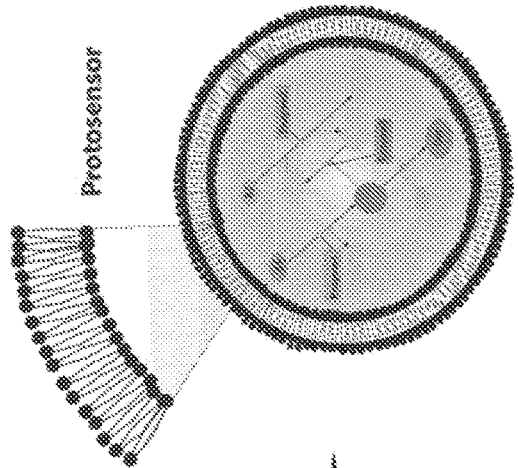
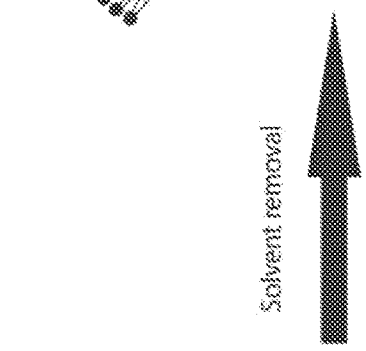
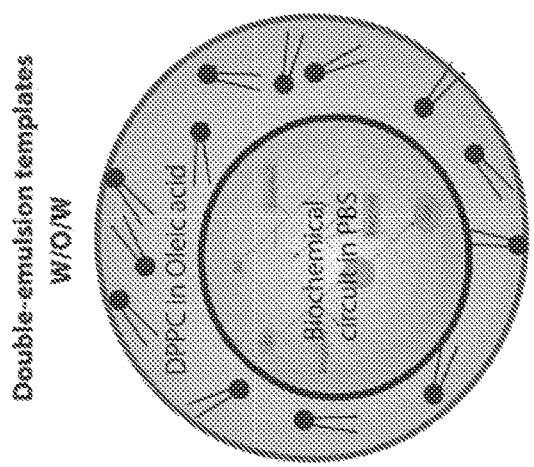
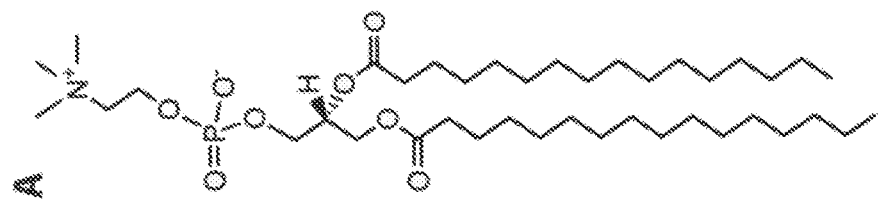
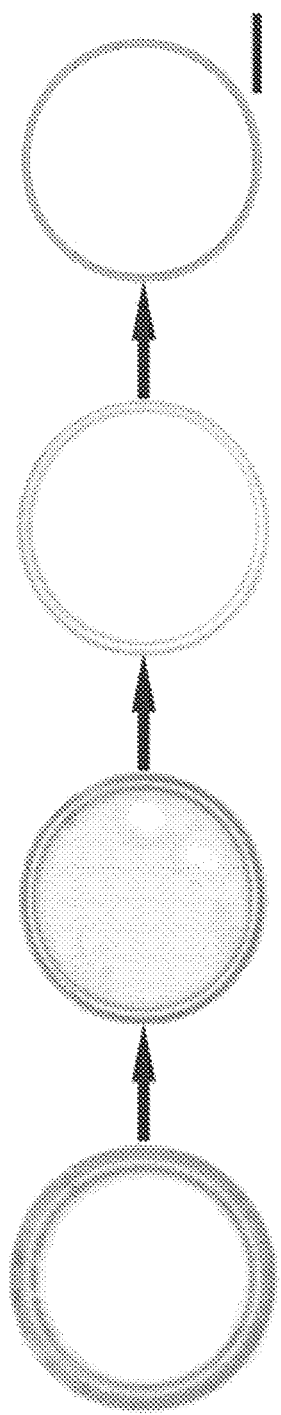
FIG. 23A
FIG. 23B
FIG. 23C

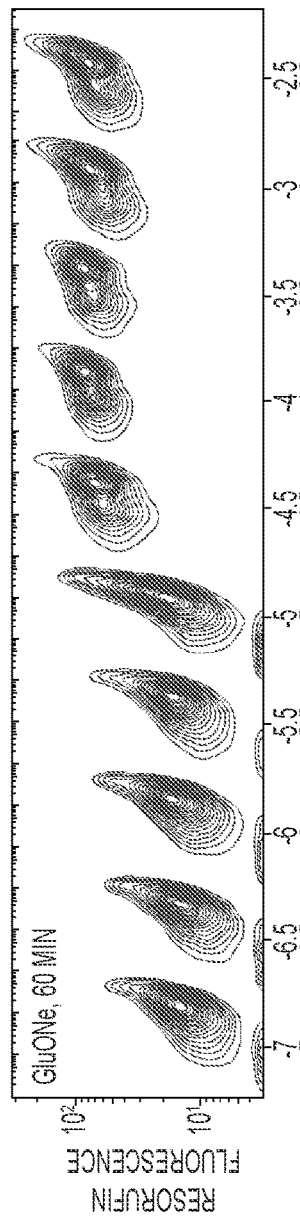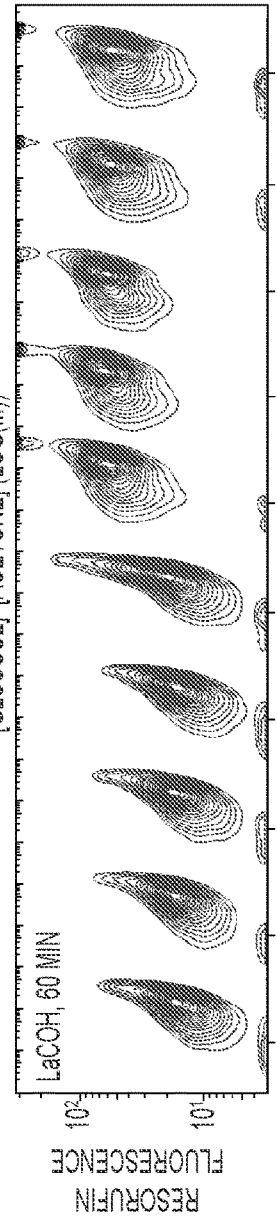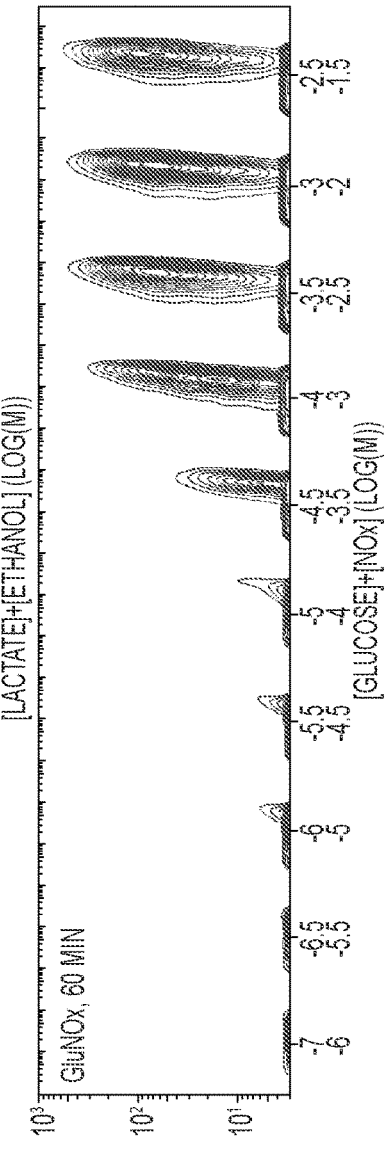

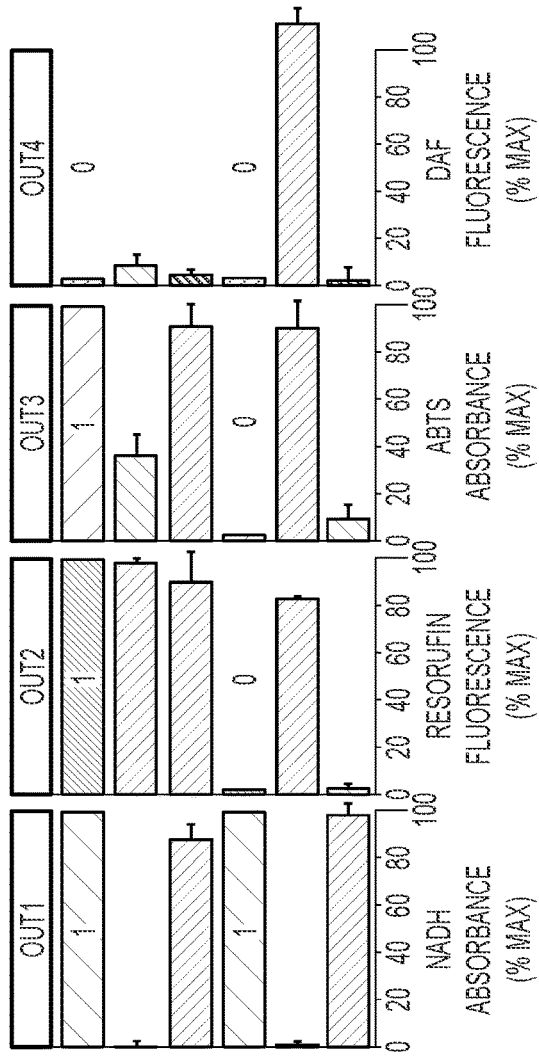
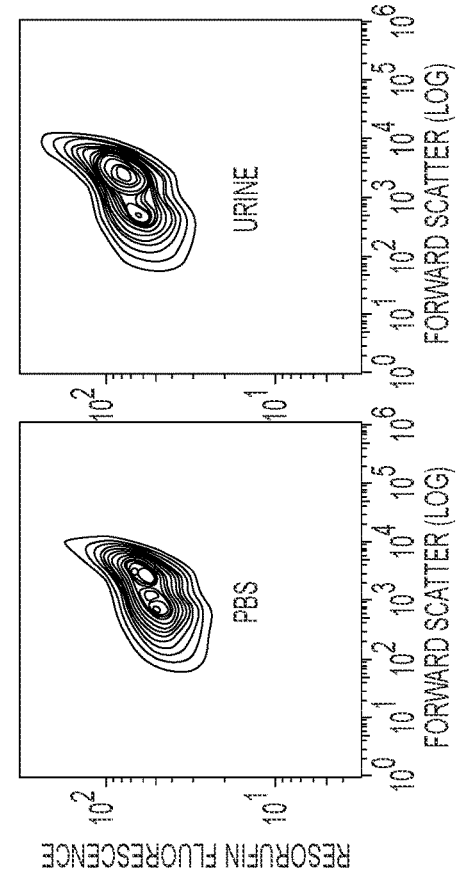
FIG. 27C
FIG. 27D

Traditional silicon serial computing

Massively parallel protocell computing

METHOD FOR THE PREPARATION OF BIOSYNTHETIC DEVICE AND THEIR USES IN DIAGNOSTICS

The present invention is directed to a method for the preparation of a non-living micro/nanoscale biosynthetic device capable of giving an information of a state of a system to analyse. Preferably, said device is used as an assay diagnostic, or to predict the risk, of a disease, or for the classification of mammal, preferably human pathologies. The invention also relates to a method for the identification and/or the quantification of a compound in a sample. Finally the present invention includes a kit comprising the biosynthetic device obtained by the method of the present invention.

Synthetic biology has become a science of designing biological components, devices, systems and organisms in a systematic and rational manner to create predictable, useful and novel biological functions Diagnostic applications have recently attracted great interest from synthetic biologists. Indeed, developing high value diagnostics, particularly clinical value remains a major technological problem of medical sciences and, in a general way, of environmental sciences. For example, medical solutions offering non-invasive and systematic screening of populations at risk in resource-limited settings, diagnosis at the patient bedside and close monitoring are thus of first importance.

The last decade witnessed important efforts to identify predictive biomarkers of diseases, as well as an interest for innovative diagnostic technologies providing with rapidity, versatility, robustness, easiness-to-use, portability, and last but not least, cost-effectiveness. Yet, novel diagnostics capable of decentralizing the biochemistry lab to the patient without scarifying medical service are still to emerge.

To achieve highest value, novel diagnostic devices would perform autonomous bio-detection of biomarkers with high sensitivity, specificity, robustness, rapidity, and possibility of direct analysis in complex matrices without sample pre-treatment.

The framework considering biological entities as systems of interacting components capable of input detection, information processing, executing logical operations, and producing an output (1), has led to the engineering of intelligent systems for bio-detection purposes and as such be used for diagnostics applications.

The engineering of cell-based biosensing system has arisen as a major focus in the field of synthetic biology (7), and proved to be useful as a versatile and widely applicable method for detection and characterization of a wide range of analytes in biomedical analysis (8). These systems are capable of producing dose-dependent detectable signals in response to the presence of specific analytes in a given sample. However, the first generation of cell-based biosensors mostly relied on native cellular sensor modules without extra signal processing abilities, and thus can only detect isolated signals with low signal to noise ratio and poor robustness when used in complex matrices.

In this perspective, top-down synthetic biology has focused on the systematic engineering of synthetic gene networks from standardized and composable genetic parts that are then assembled in living organisms (22). A wide range of modules have emerged through genetic engineering, and enhanced these systems in terms of modulation of sensitivity, specificity and dynamic range, near-real-time signal processing, multi-input (multiplexing) and logic operations, or toward the integration of orthogonal biological and electronic component (9). Cell based biosensors capable of multiplexing detection enable to classify complex conditions specified by combination of several signals. Many proofs of concept have highlighted the great advantage of in vivo integration of algorithm using biological logic circuits, in order to customize cell sensing and signaling into decision making systems, to be used for various clinical applications.

These biosensing devices are supported by a chassis, or host cell, which supplies necessary resources for functionality. The engineering of cell-based biosensor devices has been conducted in different cellular chassis, either plant, algae, mamma, yeast, and a wide spectra of bacteria species (10)

This approach has provided many useful devices and proven very valuable in the biomedical field, for example for drug production (23), to develop smart therapeutics (24) or innovative bioanalytic devices (6).

However, cell-based biosensing systems often rely on intracellular passive diffusion of analytes, or kinetics of transcriptional and translational processes that result in slow sensor responses. In addition, non-orthogonal gene circuits constitute a load in engineered cells that can interact with chassis components and result in unpredictable and noisy response profiles.

In addition, even though they proved as valuable devices capable of integrating medical expertise and providing smart analytical solutions, they still rely on the use of genetically modified living organisms, which poses ethical, evolutionary, ecological, and industrial challenges (21).

The bottom-up engineering of cell-free molecular biological circuits has witnessed a dramatic growth in achievable complexity, modularity, and programmability (25). Numerous studies have exploited nucleic acids or proteins to design molecular logic gates and biocomputing system either in vitro or in vivo (5), and it has been reported that de novo designed synthetic peptide networks can mimic some of the basic Boolean logic functions of biological networks (11). Although biochemical information processing has been extensively explored, advancing understanding about how to engineer in vitro robustness and predictability has remained a critical challenge. Biochemical circuits comprise intrinsic complexity and have thus been used less frequently than gene circuits to build synthetic systems.

To date, no clear engineering principles and methodologies exist to design and build cell-free synthetic systems according to specifications, in particular how to transform an algorithm of decision into a biochemical implementation compliant with diagnosis practices.

This is the object of the present invention.

The present invention is directed in a general way to a compartmentalized synthetic biochemical network, named "biosynthetic device", wherein this synthetic biochemical network performs a decision algorithm from input(s) (for example from biomarker inputs) and output (response of the decision algorithm).

The present invention describes and relates to a method to build said compartmentalized synthetic biochemical network in order to perform a robust decision algorithm.

Here, the inventors propose that non-living (cell-free) micro/nanoscale biosynthetic device (named also protocells according to their compartmentalized nature, and their biological information-bearing content) can be programmed to perform biodetection of disease associated biomarkers and biocomputing operations, and can be systematically generated with a robust framework to provide analytical solutions to specific environmental or clinical questions.

The methodology of the present invention particularly relies on design principle, in silico design and accurate system prediction, as well as experimental production using robust assembly methods, such as but non limited to microfluidic methods, molecular origami micro/nanostructures or encapsulation within the pores of a gel.

By implementing a full multiplexed diagnostic algorithm that discriminates between all acute metabolic complications of diabetes and achieves differential diagnosis, the inventors have demonstrated the feasibility of said approach.

The methodology relies on in silico design and accurate system prediction, as well as experimental production using for example a robust microfluidic assembly methods. The inventors have in particular demonstrated the feasibility of the approach by implementing a full diagnostic algorithm that discriminates between all acute metabolic complications of diabetes and achieves differential diagnosis. They provide experimental evidence demonstrating the technological validity, and the advantages and efficiency of this novel diagnostic approach, particularly in clinical samples for the diagnosis of human pathologies.

In a first aspect, the present invention is directed to a method for the preparation of a non-living micro/nanoscale biosynthetic device capable of giving an information of a state of a system to analyze, said method comprising the step of:
spatially confining (or compartmentalized) or encapsulating within a microenvironment,
at least biomolecular element(s), wherein said biomolecular element(s) supporting biochemical reactions to achieve biosensing of at least one biomolecular signal, and said biomolecular element(s) supporting further biochemical reactions to achieve multiplexing and integration of sensed signals into user-defined signal processing/computing/logic operations;
wherein,
said micro/nanoscale biosynthetic device is capable of performing programmable signal processing/computing operations on said biomolecular signal, and
wherein, in presence of said system to analyze, or a sample thereof, said micro/nanoscale biosynthetic device is capable of generating of at least one output signal, from said embedded biochemical reactions, in accordance to biomolecular parameters detected in the complex biological matrix, resulting from the presence of the system to analyse and the biosynthetic device, and said signal processing operations carried-out, and
wherein said at least one output signal being indicative of the state of the system to analyse.

In the present description the wording "biosynthetic device" is intended to designate a compartmentalized (also used are the wording "confined" or "encapsulated" synthetic biochemical network, wherein this synthetic biochemical network performs a decision algorithm from input(s) (for example from biomarker inputs) and output (response of the decision algorithm).

By non-living micro/nanoscale biosynthetic device according to the present invention, it is intended to exclude living cells, bacteria, virus, yeast or recombinant, engineered forms thereof In the present description, is also used the wording "confined" or "encapsulated" for the term "compartmentalized".

In a preferred biosynthetic device, the synthetic biochemical network is compartmentalized or encapsulated in a compartment, for example a vesicular system or in any other kind of compartment, having a vesicular nature or not such but not limited to a porous gel, a porous polymeric bead, phospholipids, synthetic copolymers a droplet, a liposome or is bound on a molecular origami structure system.

By non-living micro/nanoscale biosynthetic device according to the present invention In a preferred embodiment said compartment, protocell or vesicular system as defined above is delimited by a synthetic, semi-synthetic or naturally occurring membrane within the synthetic biochemical network able to perform a decision algorithm (also named biochemical synthetic circuits) and which contain said biochemical element(s), is encapsulated.

Preferred are micro/nanoscale biosynthetic devices.

By micro/nanoscale biosynthetic device it is intended to designate a device comprising a compartment, protocell(s) or vesicular system(s) as define below and in the Examples, and having preferably a size (diameter) comprised between 5 nm and 20 µm, more preferably comprised between 10 nm and 10 µm.

In the present description the wording "microenvironment" or "compartment", "protocell" and a module can be used interchangeably when these term are intended to designate a vesicular system or in any other kind of compartment, having a vesicular nature or not which is delimited by a synthetic, semi-synthetic or naturally occurring membrane within the synthetic biochemical network able to perform a decision algorithm or biochemical synthetic circuits, which comprises said biochemical element(s), is encapsulated.

In a more preferred embodiment of the method of the present invention, said microenvironment consists in a vesicular system which is delimited by a synthetic, semi-synthetic or naturally occurring membrane within the biochemical synthetic circuits which comprises said biochemical element(s) are encapsulated.

More preferably, the synthetic biochemical network able to perform a decision algorithm or the biochemical synthetic circuits is encapsulated within a phospholipid bilayer, which enables to digitize space through the definition of an insulated interior containing the synthetic biochemical network or synthetic circuit, and an exterior consisting of the medium or "complex biological matrix" to test (e.g. a mammal, preferably a human clinical sample or an environmental sample).

Although many types of vesicular system or protocells have been described regarding the nature of their membranes, they are generally composed of highly ordered amphiphilic molecules. These amphiphiles, for instance phospholipids or synthetic copolymers, comprise hydrophilic headgroups and hydrophobic chains, which can assemble into a bilayer. Orientation of hydrophilic heads in contact with the aqueous medium and hydrophobic chains with the interior in each layer is thermodynamically favored. The physicochemical properties of protocell membranes bilayers strongly depend on the nature of the amphiphiles, which will impact permeability, thickness, stability, or elasticity.

By biomolecular elements, it is intended to designate molecules that are present in living organisms, including large macromolecules such as proteins, carbohydrates, lipids, and nucleic acids, as well as small molecules such as primary metabolites, secondary metabolites, and natural products.

In a preferred embodiment of the method of the present invention, said at least biomolecular element(s) is selected from synthetic, semi-synthetic biomolecular elements or isolated from naturally occurring biological systems.

In a more preferred embodiment said at least biomolecular element(s) is selected from the group consisting of proteins, nucleic acids, preferably not expressing nucleic acids, and metabolites. Enzymes and metabolites are particularly more preferred biomolecular element(s).

Surprisingly, it has been demonstrated that these proteins, particularly the enzymes, when encapsulated in these vesicular systems exhibit a very good stability, and enhanced kinetics, even at room temperature and their activity can be then preserved during a long time (more than 3 months a room temperature)

In a preferred embodiment of the method of the present invention, said biomolecular signal is selecting from at least one biochemical or molecular parameter, more preferably selected from clinical, pollution, contamination biomarkers giving diagnostic information of a state of a system to analyse.

In a preferred embodiment of the method of the present invention, said programmable signal processing/computing operations on said biomolecular signal is an analog or digital, optionally storing and/or amplifying signal.

In a preferred embodiment of the method of the present invention, said output signal which is capable of generating by said micro/nanoscale biosynthetic device is selected from a biological, chemical, electronic or photonic signal, preferably a readable and, optionally, measurable physicochemical output signal, or a mechanical action or the synthesis and/or output secretion of a compounds of interest.

Among the signal which can be used as output signal, we can cite particularly and for example colorimetric, fluorescent, luminescent or electrochemical signal. These examples are not intended to limit the output signal which can be used in the present invention. Their choice mostly depends on assay specifications, in terms of sensitivities or technical resources. Importantly, colorimetric outputs are human readable, a property of interest for integration into low-cost, easy-to-use point of care devices, while for example luminescent signals offer ultrahigh sensitivities and wide dynamic range of detections. However, instead of measuring traditional end point signals, other biosensing frameworks exist, and can be achieved thanks to properties inherent to biological systems. It is thus possible to define different modes of readout, such as linear, frequency, or threshold, or multivalued modes of detection.

In another preferred form, in the method of the present invention, said programmable signal processing/computing operations on said biomolecular signal integrates the use of defined/programmable decision algorithms, preferably Boolean (logic gates) algorithms.

In another preferred embodiment of the method of the present invention, said prepared biosynthetic device is a device for its use as an assay diagnostic of, or predictive of the risk of, a disease, or for the classification of human pathologies and/or give information on the state of an arbitrary environment to analyze, through rational assembly of said biomolecular element(s).

In another preferred embodiment of the method of the present invention, said biomolecular element(s) supporting biochemical reactions to achieve said biosensing of at least one biomolecular signal, are selected from an automated in silico and experimental method comprising the steps of:
 a) the design and biochemical implementation of appropriate synthetic biochemical reaction circuits performing user-defined biochemical operations by selecting from said standard biomolecular elements stored in silico in appropriate and accessible databases;
 b) the mathematical dynamic modeling and prediction of for instance the sensitivity analysis, robustness analysis of said in silico designed biosynthetic devices;
 c) generating at least one microenvironment or module encapsulated within a synthetic membrane, said microenvironment or module comprising said at least biomolecular element(s), selected in step a);
 and
 d) generating a biosynthetic device by assembling said microenvironments or encapsulated module generated in step c)

In another preferred embodiment, said method further comprises after the step d) the steps of:
 e) measuring a multiplicity of known samples that have been characterized with respect to the disease/classification of pathologies/state of an arbitrary environment which is desired to analyze, and
 f) optimization of the logical relationships within and between the biomolecular elements and repeating one or more of these steps iteratively so as to further optimize the performance of the algorithm of interest compared with existing diagnostic techniques as to produce an optimized biomarker.

In a preferred embodiment, said at least biomolecular element(s) selected in step a) in an enzyme or a metabolite.

In another preferred embodiment of the method of the present invention, said microenvironment (or module) of said device comprises at least two compatible biomolecular elements, preferably two compatible enzymes or compatible metabolites.

In another preferred embodiment of the method of the present invention, said device comprises at least two different microenvironments (or modules), this device being capable of biosensing of at least two different biomolecular signals.

In another preferred embodiment of the method of the present invention, said biomolecular element(s) is spatially encapsulating within a liposome, a droplet, a polymeric support with selective permeability, more preferably within a liposome.

In another aspect, the present invention relates in a general way to a micro/nanoscale biosynthetic, preferably diagnostic, device obtainable or obtained by the method according to the present invention, said biosynthetic device comprising a compartmentalized synthetic biochemical network, wherein this synthetic biochemical network performs a decision algorithm from input(s) (for example from biomarker inputs), preferably from at least two inputs, and output (preferably corresponding to the response of the decision algorithm).

In a preferred embodiment, the present invention relates to a micro/nanoscale biosynthetic, preferably diagnostic, device obtainable or obtained by the method according to the present invention, said device comprising:
 a) Synthetic or semi-synthetic biomolecular element(s) or element(s) isolated from naturally occurring biological systems, preferably selected from the group consisting of proteins, more preferably enzymes, nonexpressing nucleic acids and metabolites,
 and wherein,
 said biomolecular element(s) or element(s) is (are) spatially confined/compartmentalized within a synthetic, semi-synthetic or naturally occurring membrane or polymeric support with selective permeability, b) said biomolecular or isolated elements supporting biochemical reactions to achieve biosensing of at least one biomolecular signal in a complex biological matrix,
c) said biomolecular elements supporting biochemical reactions to achieve multiplexing and integration of sensed signals into user-defined signal processing/computing/logic operations
e) said device being capable of performing, programmable signal processing/computing operations on biomolecular signal,
f) said device being capable of generating of at least one readable/measurable output by embedded biochemical reactions, in accordance to biomolecular parameters detected in a complex biological matrix and signal processing operations carried-out, giving information on the biological matrix point.

In a preferred embodiment, the present invention relates to a micro/nanoscale biosynthetic diagnostic, device obtainable or obtained by the method according to the present invention, more preferably in the field of health, agronomic food or environment diagnostic, health diagnostic field being the more preferred.

In another aspect, the present invention is directed to a method for the identification and/or the quantification of a compound in a sample, comprising the steps of:
a) bringing into contact a micro/nanoscale biosynthetic device obtainable or obtained by a method according to the present invention, or a micro/nanoscale biosynthetic device as defined in the present invention, with a sample susceptible to contain said compound, to generate a mixture,
b) incubating said mixture in conditions adapted for the performance of at least one biochemical reaction, to generate at least said output signal, preferably readable/measurable physicochemical output signal, wherein said output signal being indicative of the presence and/or the level of the compound which is desired to analyze in said sample
c) detecting or measuring the output signal generated at step b), and
d) determining, form the signal generated/measured in step c), the presence and/or the level of said compound.

In another aspect, the present invention is directed to a method for the diagnostic of, or predictive of the risk of, a disease, or for the classification of human pathologies, said method comprising:
a) obtaining one biosynthetic device or a multiplicity of biosynthetic devices obtainable or obtained by a method according to the present invention, or a micro/nanoscale biosynthetic device as defined in the present invention, said device containing one type of compartment, microenvironment, module or protocell, or different types thereof, the distribution of which (compartment, microenvironment, module, protocell or devices) has previously been optimized with respect to the diagnostic purpose of interest;
b) bringing into contact said biosynthetic device(s) with a patient sample;
c) detecting or measuring the output signal generated at step b) for each device), said signal generated/measured in step c), being indicative of the diagnostic of, or predictive of the risk of, a disease, or for the classification of human pathologies in said patient.

In a preferred embodiment of the method for the diagnostic according to the present invention, said sample to test is selected from urine, serum, blood, foods, raw materials, and environmental sample. More preferably selected from urine, serum or blood, when the method is a method for the diagnostic of, or predictive of the risk of, a disease, or for the classification of human pathologies.

Are preferred, pathology or disease for which biomarkers associated with said pathology are known. Particularly selected from the group of diabetes, cardiovascular, renal, ocular and healing pathology. Diabetes being the more preferred.

In a particularly preferred aspect, the present invention is directed to a micro/nanoscale biosynthetic device obtainable or obtained by a method according to the present invention, or a micro/nanoscale biosynthetic device as defined in the present invention for use for the diagnosis of glycosuria in a patient, wherein said patient suffers from diabetes.

Numerous human studies have consistently demonstrated that concentrations of branched-chain amino acids (BCAAs) in plasma and urine are associated with insulin resistance and have the quality to predict diabetes development (see Giesbertz P. et al. Curr Opin Clin Nutr Metab Care. 2016 January; 19(1):48-54)

Thus, in another particularly preferred aspect, the present invention is directed to a micro/nanoscale biosynthetic device obtainable or obtained by a method according to the present invention, or a micro/nanoscale biosynthetic device as defined in the present invention for use for measuring the branched-chain amino acids (BCAA) in a patient sample.

In another preferred aspect, the present invention is directed to a micro/nanoscale biosynthetic device obtainable or obtained by a method according to the present invention, or a micro/nanoscale biosynthetic device as defined in the present invention for use for the diagnostic of differential disease state classification of diabetes or a diabetes complication chosen among: diabetes, hypoglycemia, diabetic ketoacidosis, hyperosmolar non-ketotic diabetes, lactic acidosis, insulin resistance, early insulin resistance and ethylism.

In a preferred embodiment, in the micro/nanoscale biosynthetic device obtainable or obtained by a method according to the present invention, or the micro/nanoscale biosynthetic device as defined in the present invention, the selected biochemical elements encapsulated in said module are selected from the group consisting of enzymes or metabolites, preferably selected from the following:
enzymes: Glucose-1-dehydrogenase, Glucose oxydase, Alcohol-dehydrogenase, leucine dehydrogenase, Nitrate reductase, Lactate oxidase, Alcohol oxidase, Horse radish-peroxidase, and
metabolites: resazurin, NADH, NAD, ABTS, MTT (3-(4, 5-dimethylthiazol-2-yl)-2,5-diphenyltetrazolium bromide).

In a preferred embodiment, the micro/nanoscale biosynthetic device obtainable or obtained by a method according to the present invention, or the micro/nanoscale biosynthetic device as defined in the present invention is used for the diagnostic of insulin resistance or early insulin resistance in a patient, wherein said module contains as encapsulated biochemical elements:
enzyme: leucine dehydrogenase; and, optionally
metabolites: MTT, NADH, NAD.

In a preferred embodiment, the micro/nanoscale biosynthetic device obtainable or obtained by a method according to the present invention, or the micro/nanoscale biosynthetic device as defined in the present invention is used for the diagnostic of insulin resistance or early insulin resistance, and diabetes in a patient, wherein said method or device implements two different modules:

a) a first module containing as encapsulated biochemical elements:
    enzyme: leucine dehydrogenase; and, optionally
    metabolites: MTT, NADH, NAD; and
b) a second module containing as encapsulated biochemical elements:
    enzyme: Glucose-1-dehydrogenase, or Glucose oxydase, and Horse radish-peroxidase; and, optionally
    metabolites: resazurin.

In a particular embodiment, the micro/nanoscale biosynthetic device obtainable or obtained by a method according to the present invention, or the micro/nanoscale biosynthetic device as defined in the present invention is used for the diagnostic of insulin resistance or early insulin resistance, and diabetes in a patient, wherein said method or device implements one module, as a micro/nanoscale biosynthetic device, vesicule or a liposome, according to the present invention, said one module containing as encapsulated biochemical elements:
    enzymes: both glucose oxydase, or glucose 1-dehydrogenase, and leucine dehydrogenase, and, optionally Horse radish-peroxidase (HRP);
and, optionally,
    metabolites: rezasurin, NADH, NAD, and, optionally, MTT.

Said one module being capable of measurinf the BCAAs level and the glucose level in a patient sample, as but non-limited to, urine or blood sample.

In the micro/nanoscale biosynthetic device obtainable or obtained by a method according to the present invention, or the micro/nanoscale biosynthetic device as defined in the present invention, it is preferred that said output signal, is a chemical, biological, electronic or photonic signal, or a physicochemical output signal, preferably readable/measurable signal, or/and is capable of carrying out a mechanical action or the synthesis and/or output secretion of a compounds of interest, Examples of readable/measurable signal can be particularly cited:

Intracellular protein staining, RNA detection, Enzyme-linked immunospot (ELISPOT), Fluorometry, fluorescence staining, quantification using limiting dilution assays, colorimetric measurement, indicator substances, kinetic patterns, concentration patterns ELISA and similar assays, high-throughput genomics and proteomics, mass spectroscopy or other signal well known by the skill person.

In another aspect, the present invention relates to a kit comprising at least a biosynthetic device obtainable or obtained by a method according to the invention or as defined in the present invention.

Preferably, the kit according to the present invention comprises at least a module, as but non limited to a vesicule, a liposome (non-living biosynthetic device) containing as encapsulated biochemical elements:
    enzyme: leucine dehydrogenase; and, optionally
    metabolites: MTT, NADH, NAD; and, optionally
b) a second module containing as encapsulated biochemical elements:
    enzyme: Glucose-1-dehydrogenase and Horse radish-peroxidase; and, optionally
    metabolites: resazurin.

In a particular embodiment, the kit according to the present invention comprises one module, as a vesicule or a liposome, according to the present invention and containing as encapsulated biochemical elements:
    enzymes: both glucose oxydase, or glucose 1-dehydrogenase, and leucine dehydrogenase, and, optionally Horse radish-peroxidase (HRP);
and, optionally,
    metabolites: rezasurin, NADH, NAD, and, optionally, MTT.

In a particular embodiment, the kit according to the present invention comprises one module, as a vesicule or a liposome according to the present invention and containing as encapsulated biochemical elements:
    enzymes: both glucose oxydase, or glucose 1-dehydrogenase, and leucine dehydrogenase, and, optionally Horse radish-peroxidase (HRP);
and, optionally,
    metabolites: rezasurin, NADH, NAD, and, optionally, MTT.

The following examples, the figures and the legends hereinafter have been chosen to provide those skilled in the art with a complete description in order to be able to implement and use the present invention These examples are not intended to limit the scope of what the inventor considers to be its invention, nor are they intended to show that only the experiments hereinafter were carried out.

Other characteristics and advantages of the invention will emerge in the remainder of the description with the Examples and Figures, for which the legends are given hereinbelow.

FIGURE LEGENDS

Figure 1B:
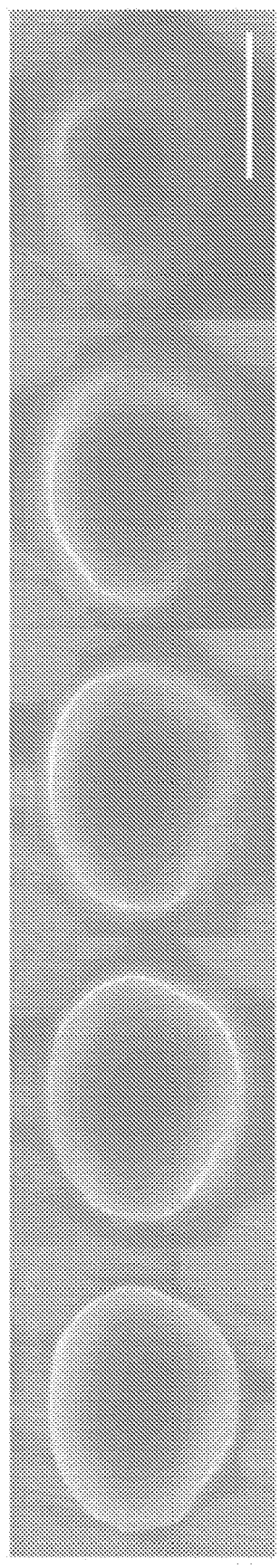

FIGS. 1A-1B: Environmental Scanning Electron Microscopy (ESEM) photomicrograph of protosensors. DPPC vesicles were fixed overnight at 4° C. in 2.5% glutaraldehyde solution in PBS, and then washed with water prior to direct observation. (A) Stereoscopic micrograph of individual protosensor (B) Kinetic visualization of electron beam interacting with a protosensor. From left to right: 10 seconds were sufficient to melt the DPPC bilayer and release intra-vesicular content. (Scale bar=10 μm)

Figure 2:
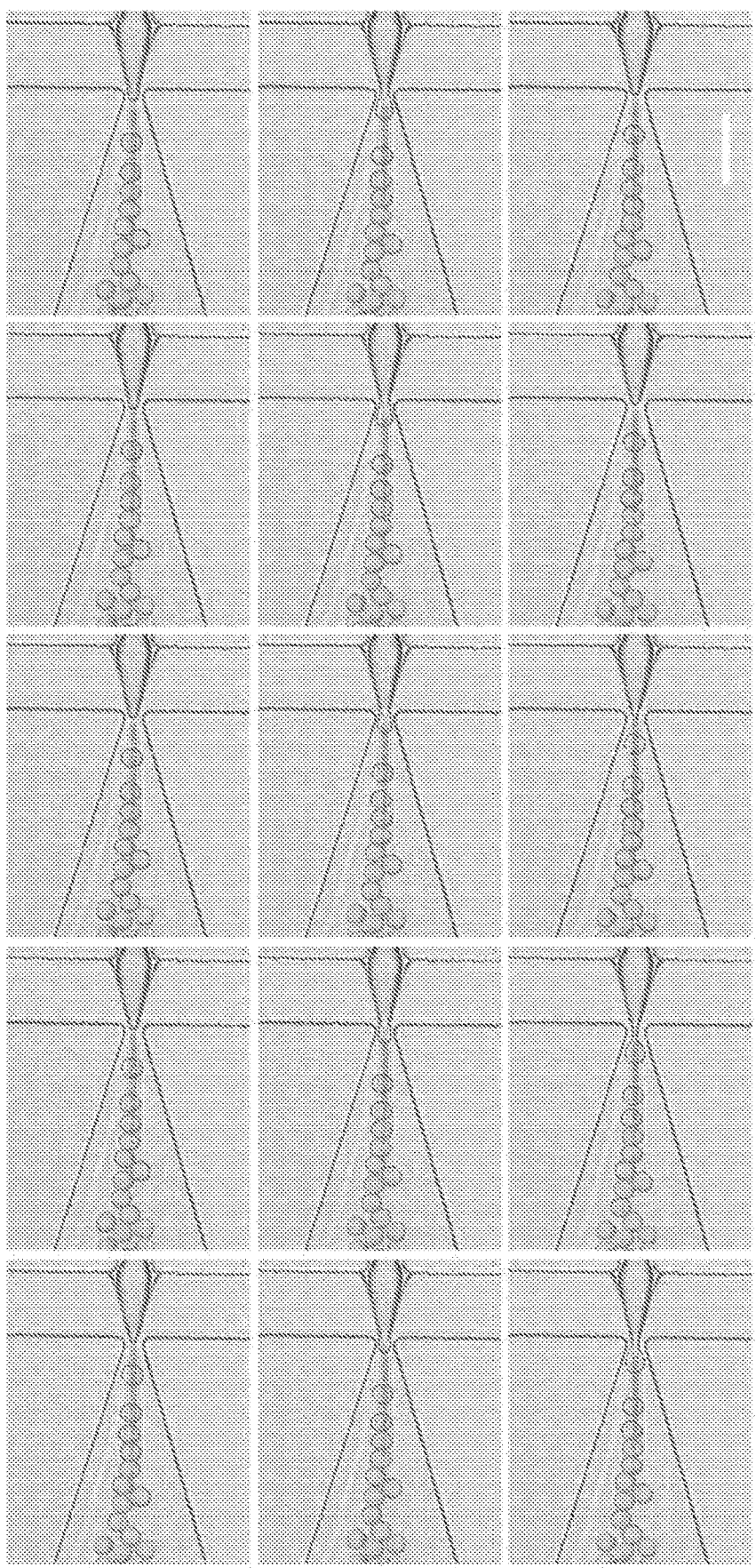

FIG. 2: Timelapse photomicrograph of protosensors fabrication within microchannels. (Read from left to right, top to bottom). This movie was recorded at 20 000 FPS and corresponds to ~0.5 μs. (Scale bar=40 μm)

FIGS. 3A-3C: UPLC-Mass spectrometry experiments to assay enzyme encapsulation in protocells. Experiments were performed on an Acquity UPLC (Waters) coupled with a TSQ Quantum (Thermofischer). Briefly, we used a Kinetex C18 column (100×2.1 mm 2.6 um) with H2O+0.01% formic acid and acetonitrile+0.01% formic acid as eluents and a flow rate of 0.5 ml/ml, with ESI+ detection. (A) Chromatogram of G1DH enzyme in PBS buffer and MS spectra of main peak, which enables to identify the enzyme with a mass corresponding to literature (~30 kDa) (B) Chromatogram of AO enzyme in PBS buffer and MS spectra of main peak, which enables to identify the enzyme with a mass corresponding to literature (~74 kDa) (C) Chromatogram of protosensor encapsulating G1DH and AO enzymes in PBS buffer, and MS spectra of main peaks, which enables to identify the two enzymes.

Figure 4:
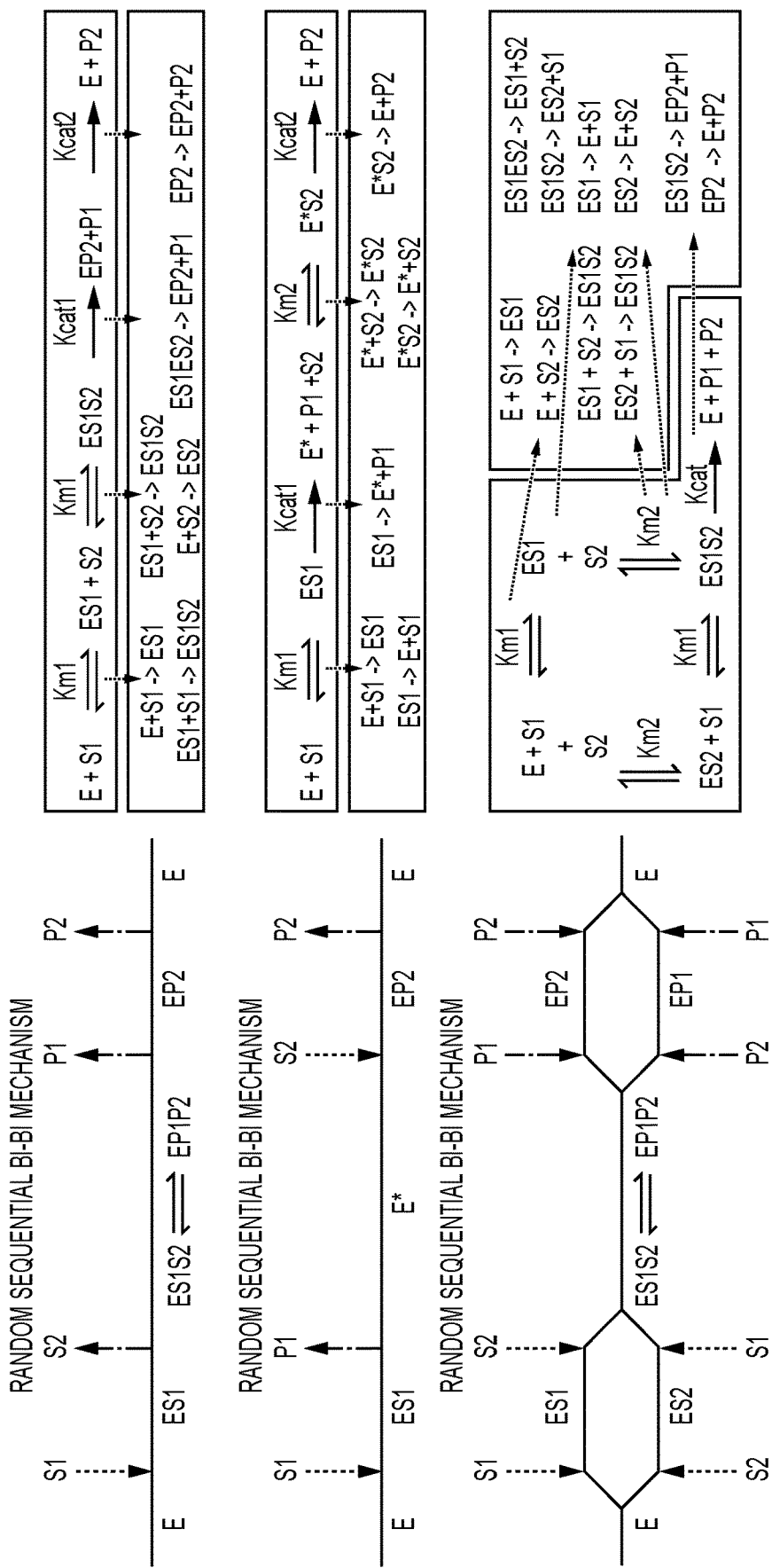

FIG. 4: Multisubstrate mechanisms for enzymatic reactions and corresponding HSIM equations.

Figure 5A:
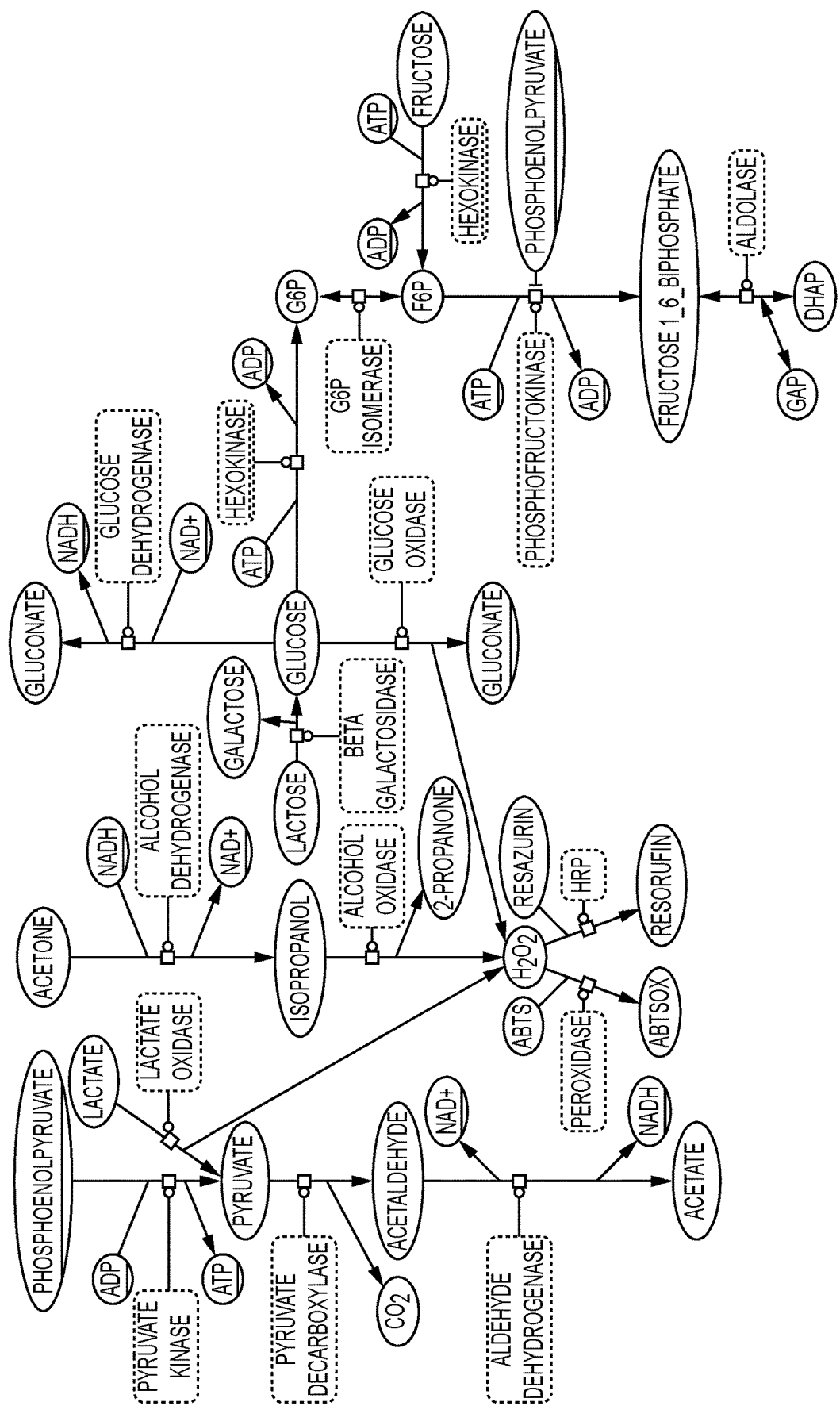
Figure 5B:
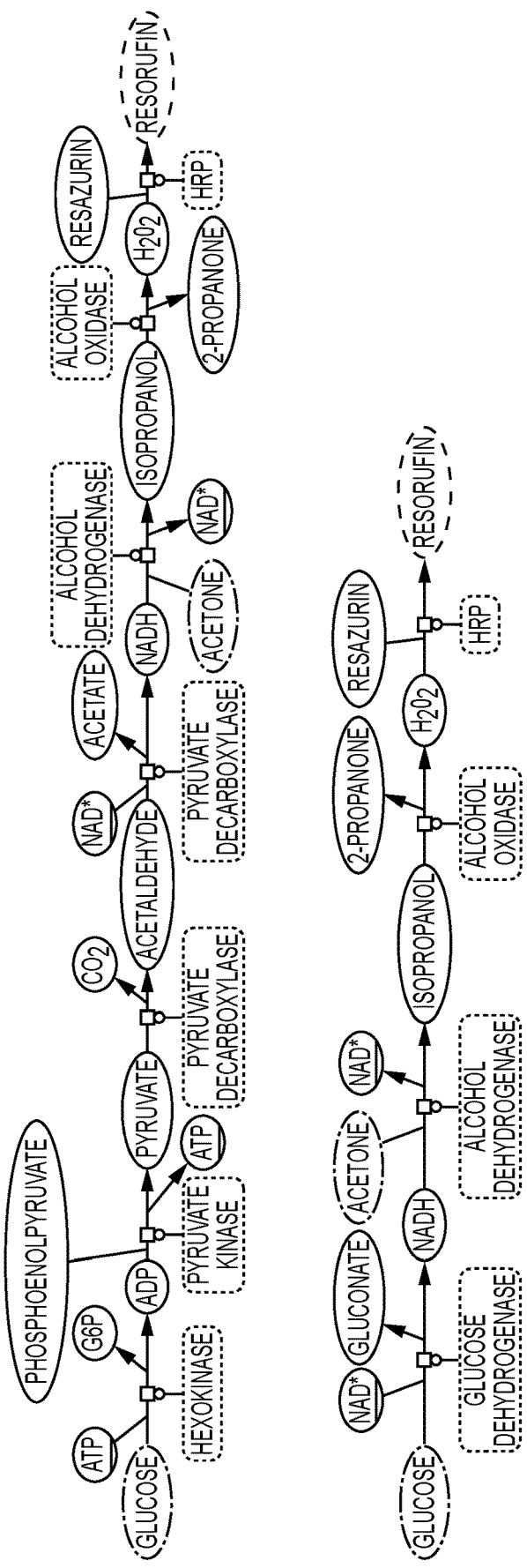

FIGS. 5A-5B: Example of automated biochemical implementation of user defined enzymatic Boolean logic gate from natural metabolic networks. (A) Input arbitrary metabolic network comprising biochemical reactions from glycolytic pathways, which will be mined to find enzymatic logic gates. An implementation of a logic gate is a subnetwork where appropriate biomolecular inputs and output are identified. (B) A given Boolean function with its truth table is given to the in silico tools (NetGate and Netbuild), in this case the GluONe system, and the metabolic network will be searched for corresponding concatenated logic gates. Briefly, in a first step, all the possible implementations of the logic gates present in the input network are enumerated. In a second step, these implementations are checked against the given truth tables and the gates found are sorted. In this example, the software found 2 implementations satisfying GluONe biomolecular logic from the input network. The simplest one is the synthetic circuit chosen in this study.

Figure 6A:
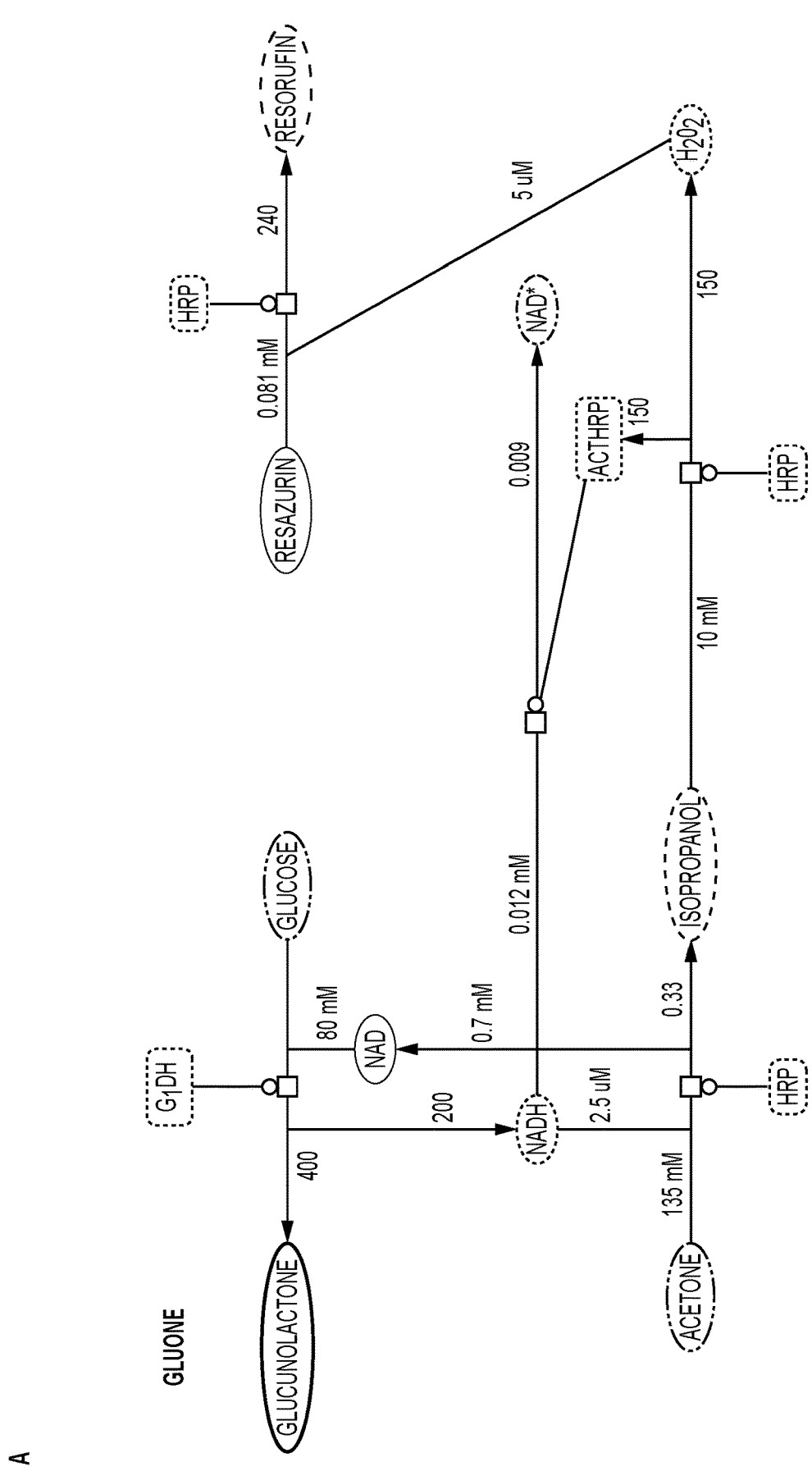
Figure 6B:
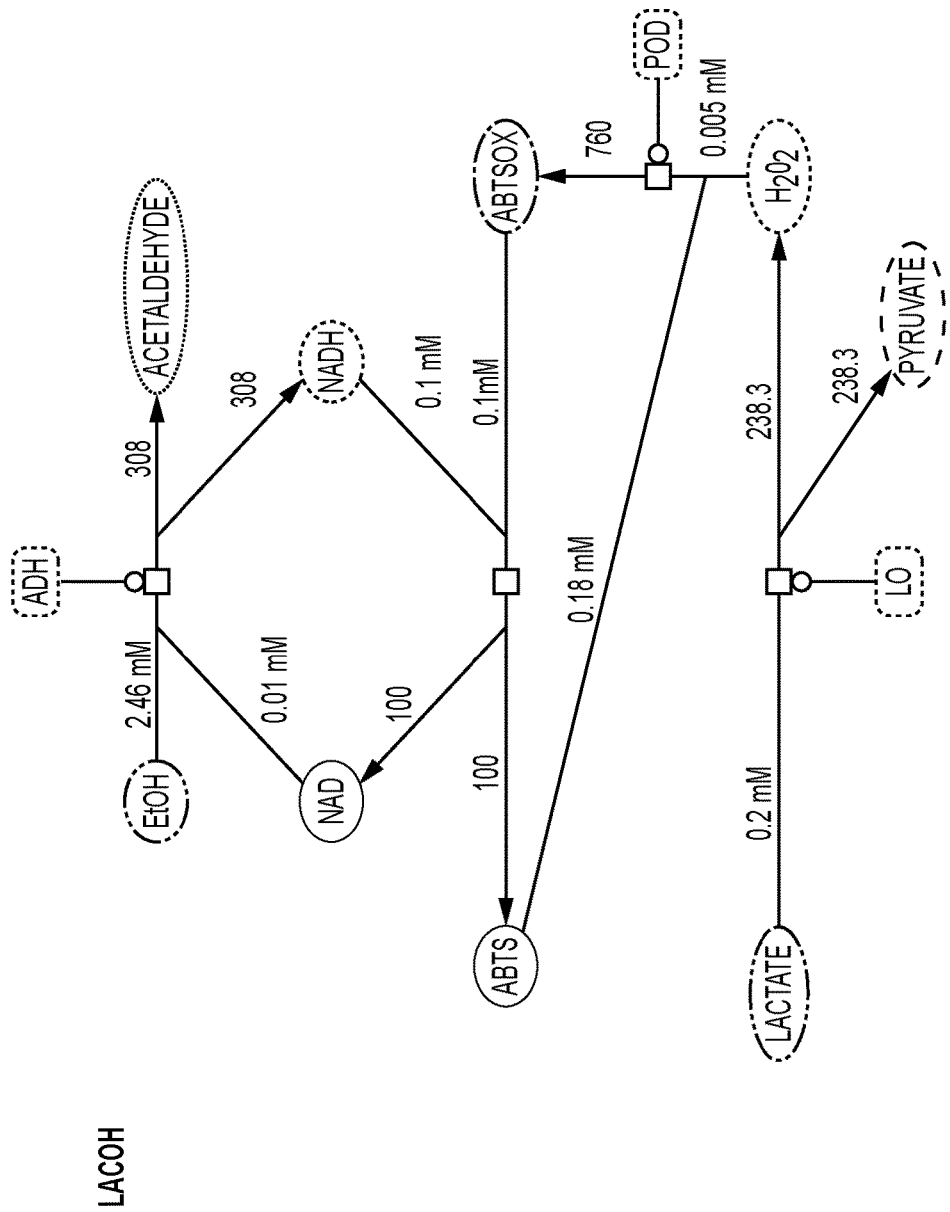
Figure 6C:
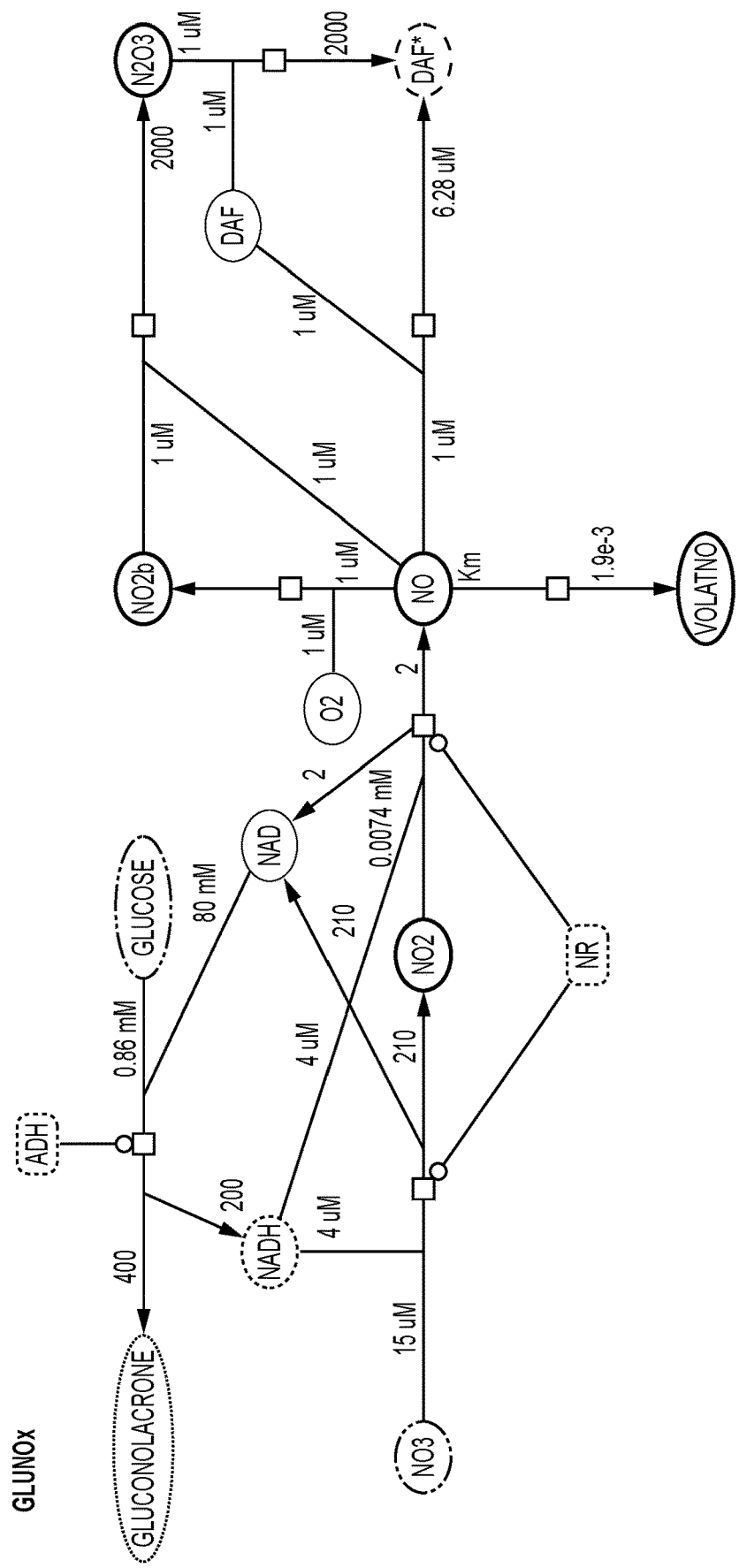

FIGS. 6A-6C: Topology of biochemical circuits with kinetic parameters that were designed and used in this study. Metabolites corresponding to systems inputs are depicted in yellow. (A) The GluONe system takes Glucose and Acetone as inputs in the medium and applies AND and N-Imply Boolean logic to inputs, to generate a absorbance and fluorescent output signal in the molecular form of NADH and Resorufin, respectively. It comprises 4 different enzymes and 2 different metabolites. (B) The LacOH system takes Lactate and Ethanol as inputs in the medium and applies N-Imply Boolean logic to inputs, to generate an absorbance and colorimetric output signal in the molecular form of oxidized ABTS. It comprises 3 different enzymes and 2 different metabolites. (C) The GluNOx system takes Glucose and NOx as inputs in the medium and applies AND Boolean logic to inputs, to generate a fluorescent output signal in the molecular form of nitrosylated DAF-2. It comprises 3 different enzymes and 2 different metabolites.

Figure 7A:
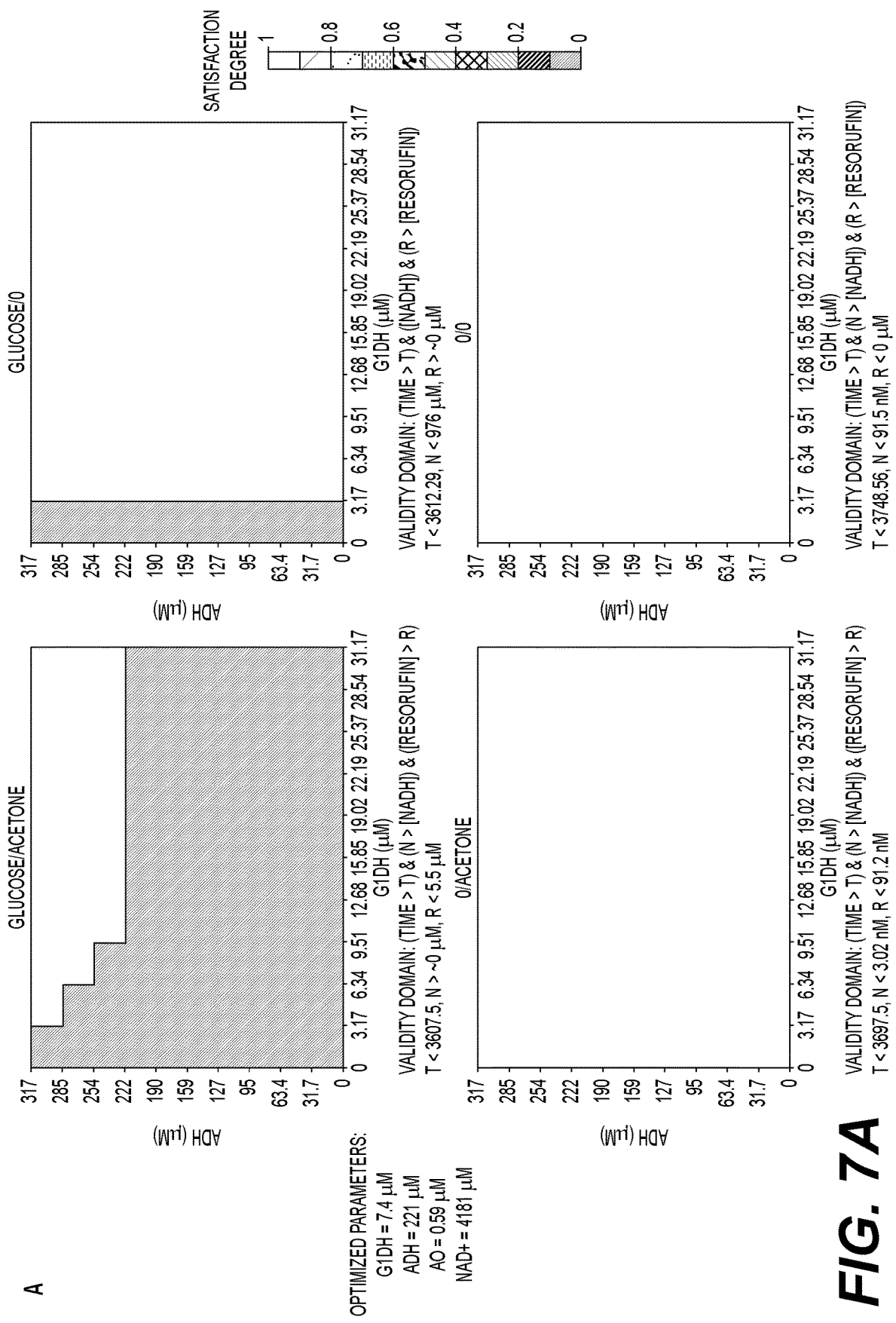
Figure 7B:
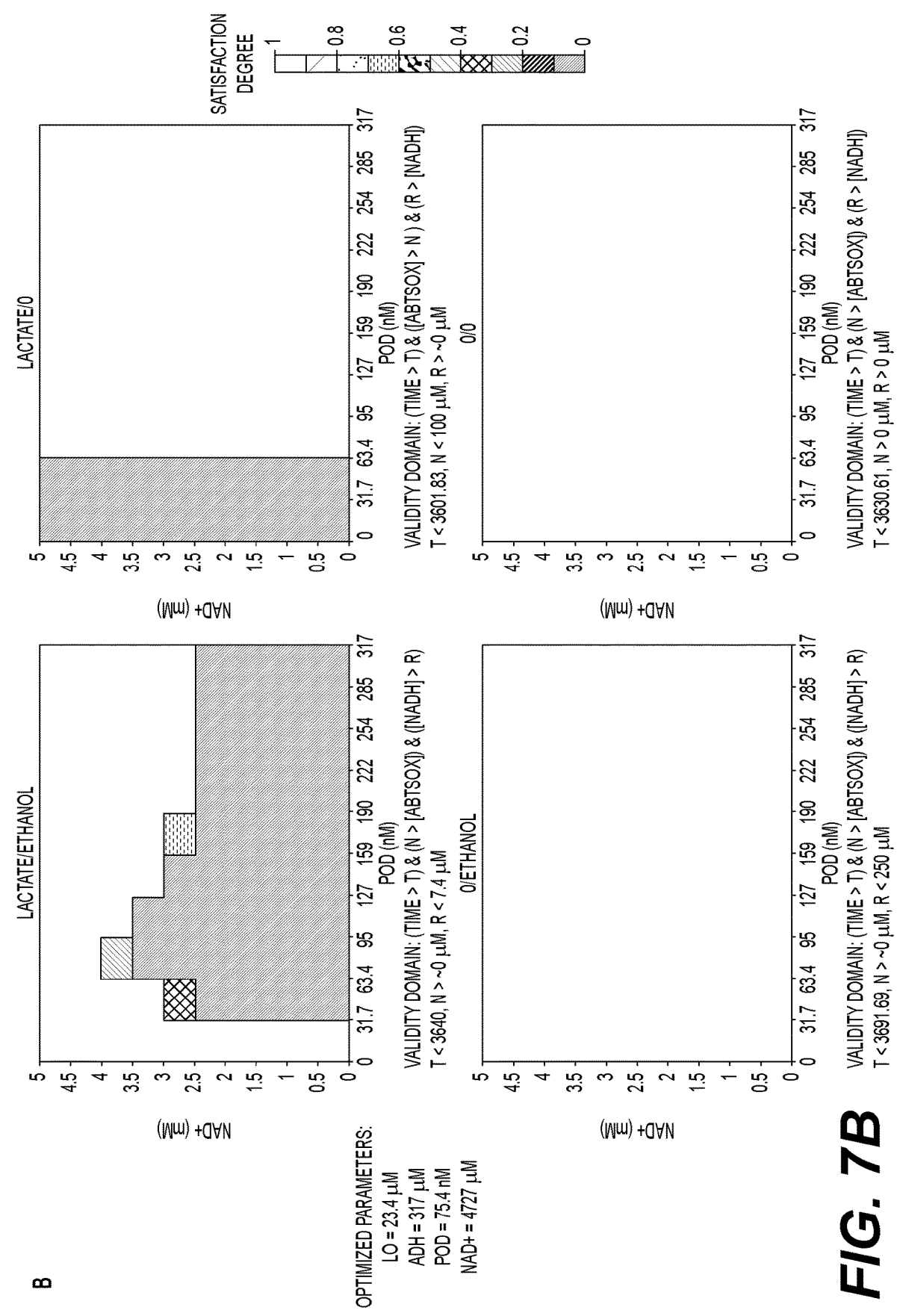
Figure 7C:
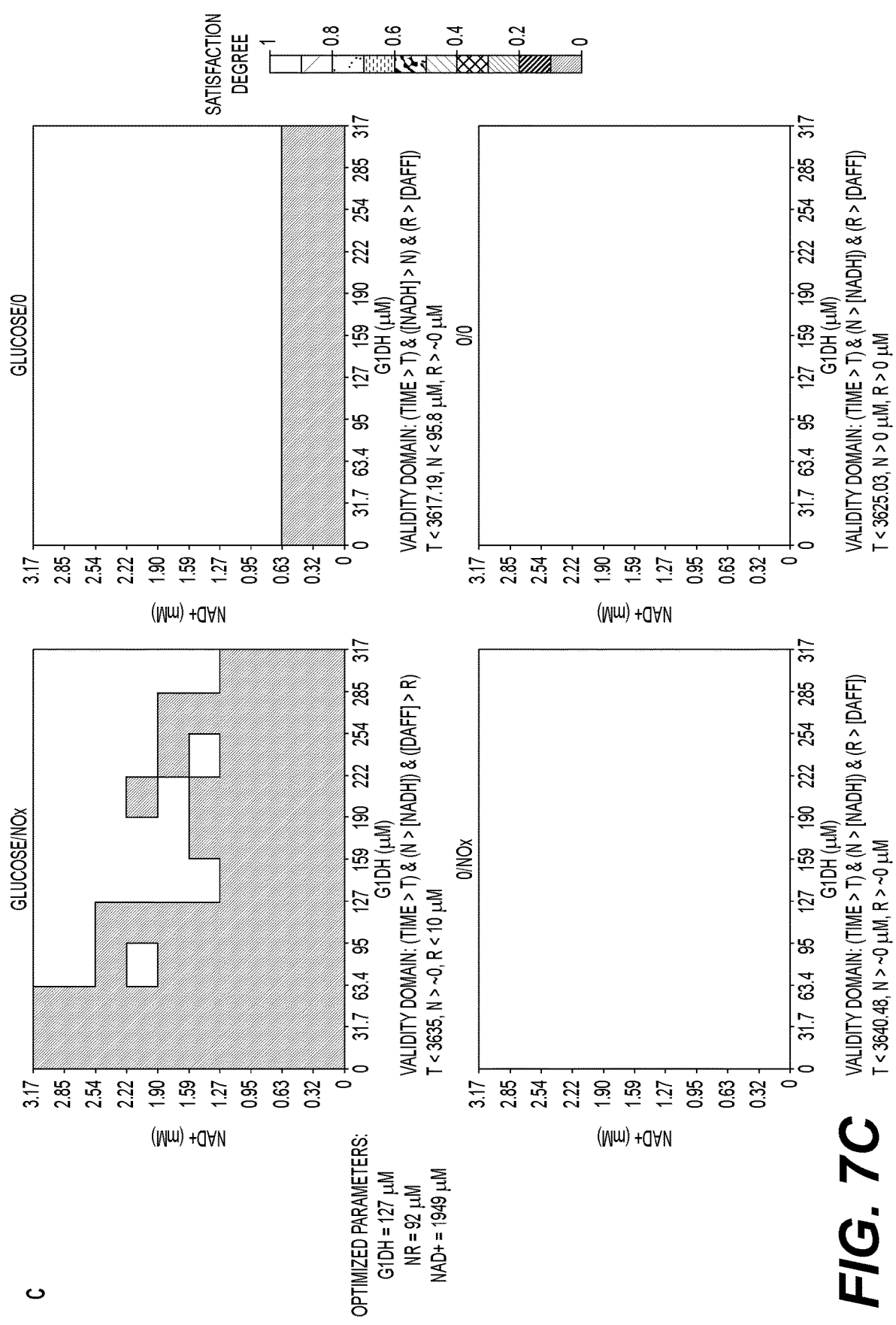

FIGS. 7A-7C: Mapping satisfaction degree landscape for (A) GluOne, (B) LacOH and (C) GluNOx biochemical circuits in protocells and different input biomarkers according to clinical specifications. Satisfaction degrees of temporal logic formulas at 10 minutes were computed while varying the two most sensitive parameters of respective models (e.g. ADH and G1DH), for each combination of inputs. Validity domain for temporal specification of output concentration thresholds at steady state are depicted below each maps. Optimized concentration parameters were then computed using C-MAES method implemented in Biocham.

Figure 8A:
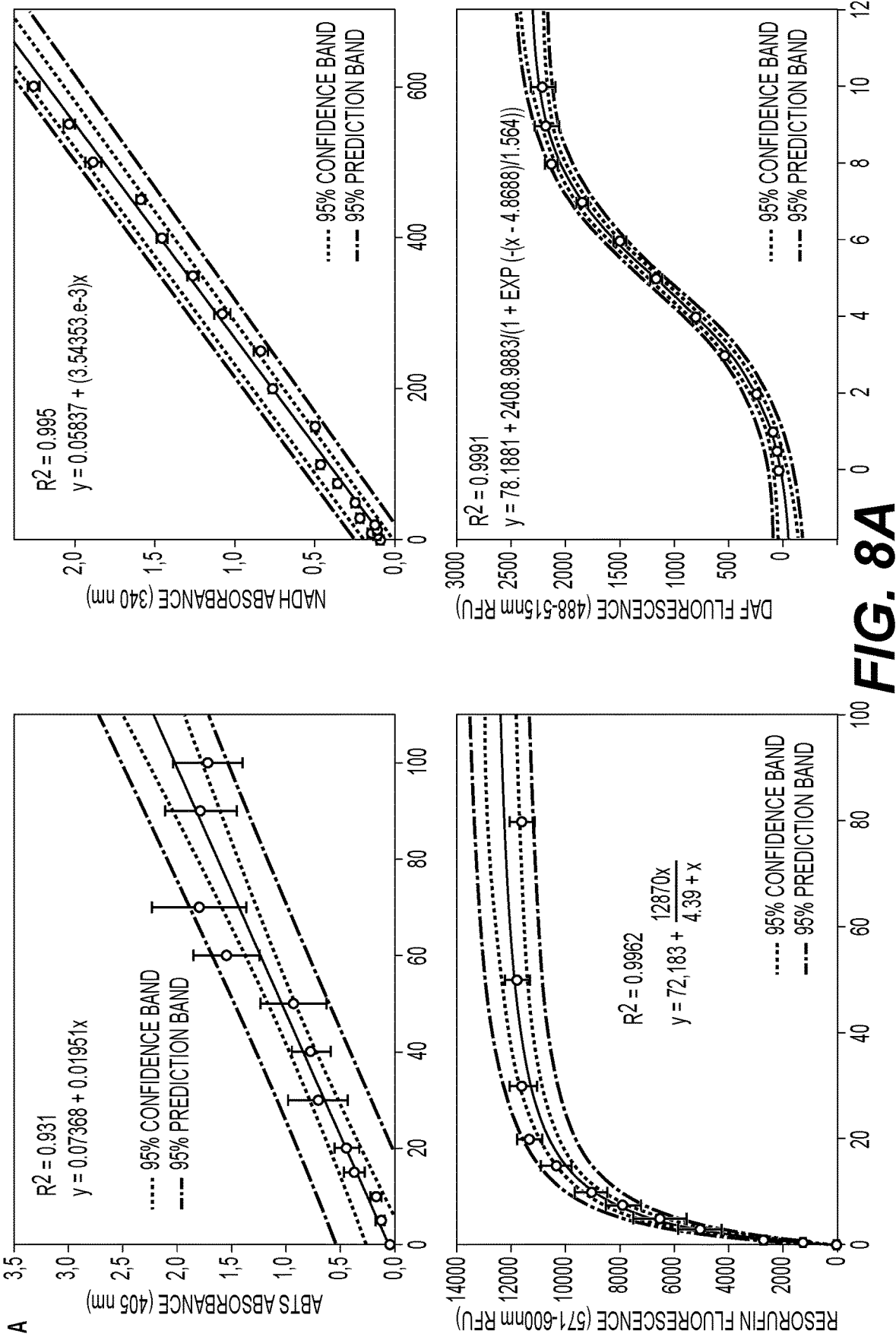
Figure 8B:
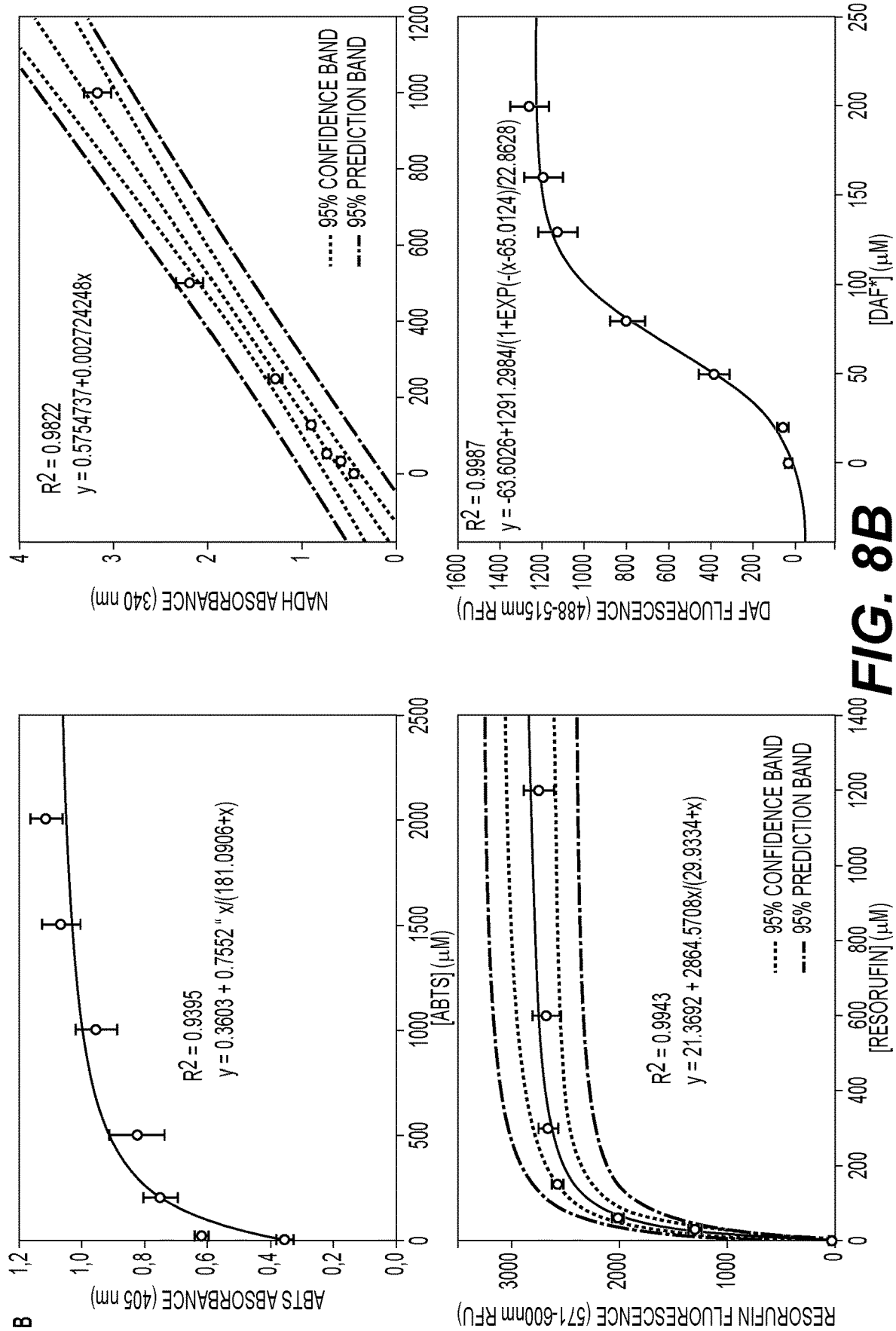

FIGS. 8A-8B: Experimental calibration curves used to compute output signals. In order to obtain a mathematical relation between concentration of outputs and experimental fluorescence and absorbance measurements, we measured signals from samples spiked with known concentration of output molecules. (A) Output molecular signal in PBS buffer (B) Output molecular signals in protosensors. Depicted are the mathematical formulas used to compute output signals in in silico simulation.

FIG. 9: Detailed experimental kinetic characterization of synthetic biochemical circuits in vitro. Enzymes and metabolites were mixed in p96 100 µl wells in PBS, homogeneized via smooth agitation, and inputs were added last. Kinetic measurements were performed on a Synergy H1 plate reader, under slow agitation at 25° C.

FIG. 10: Detailed experimental logic characterization of synthetic biochemical circuits in vitro. In this figure are depicted measurements obtained as previously detailed in FIG. 9.

Figure 11:
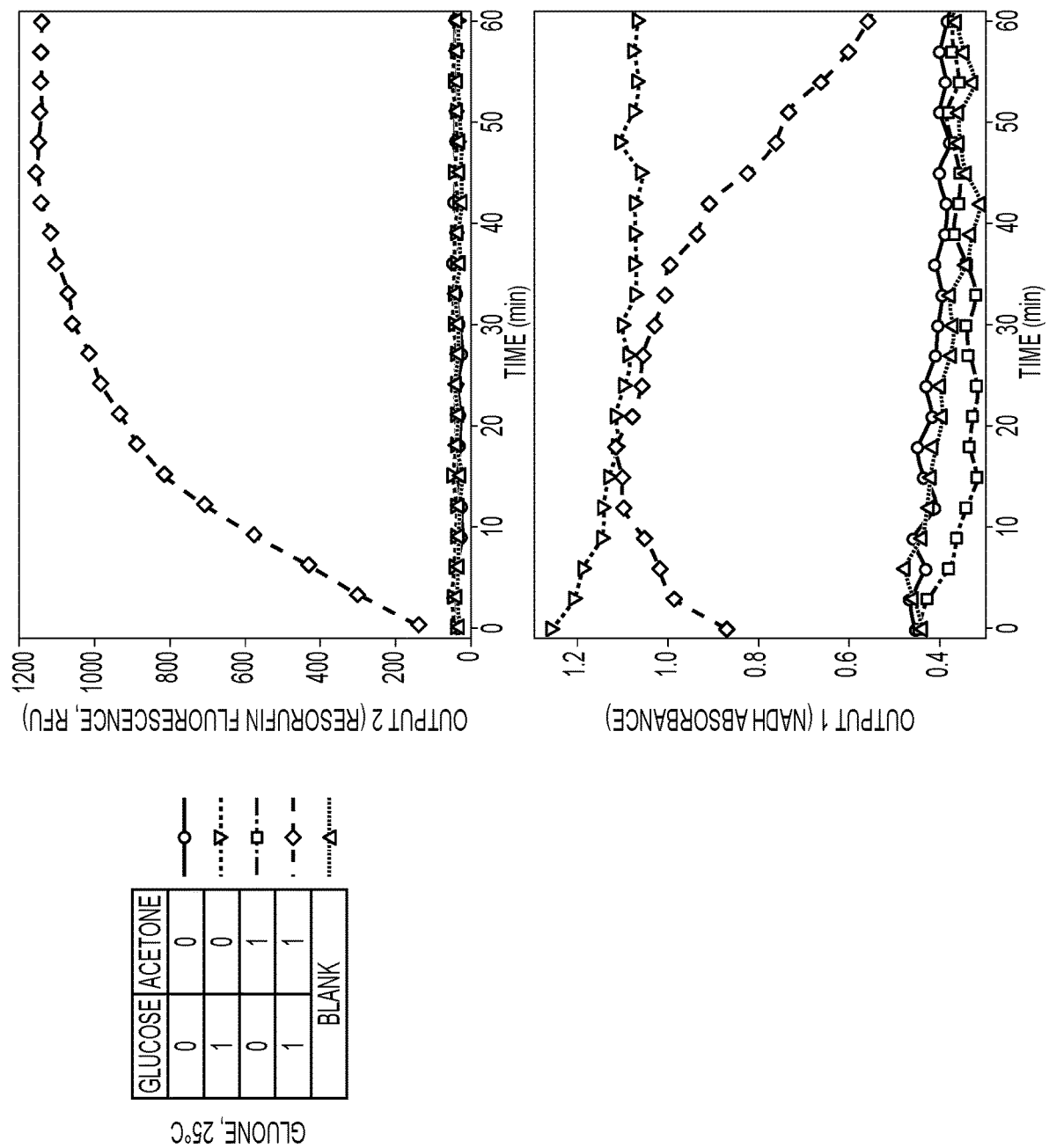
Figure 11:
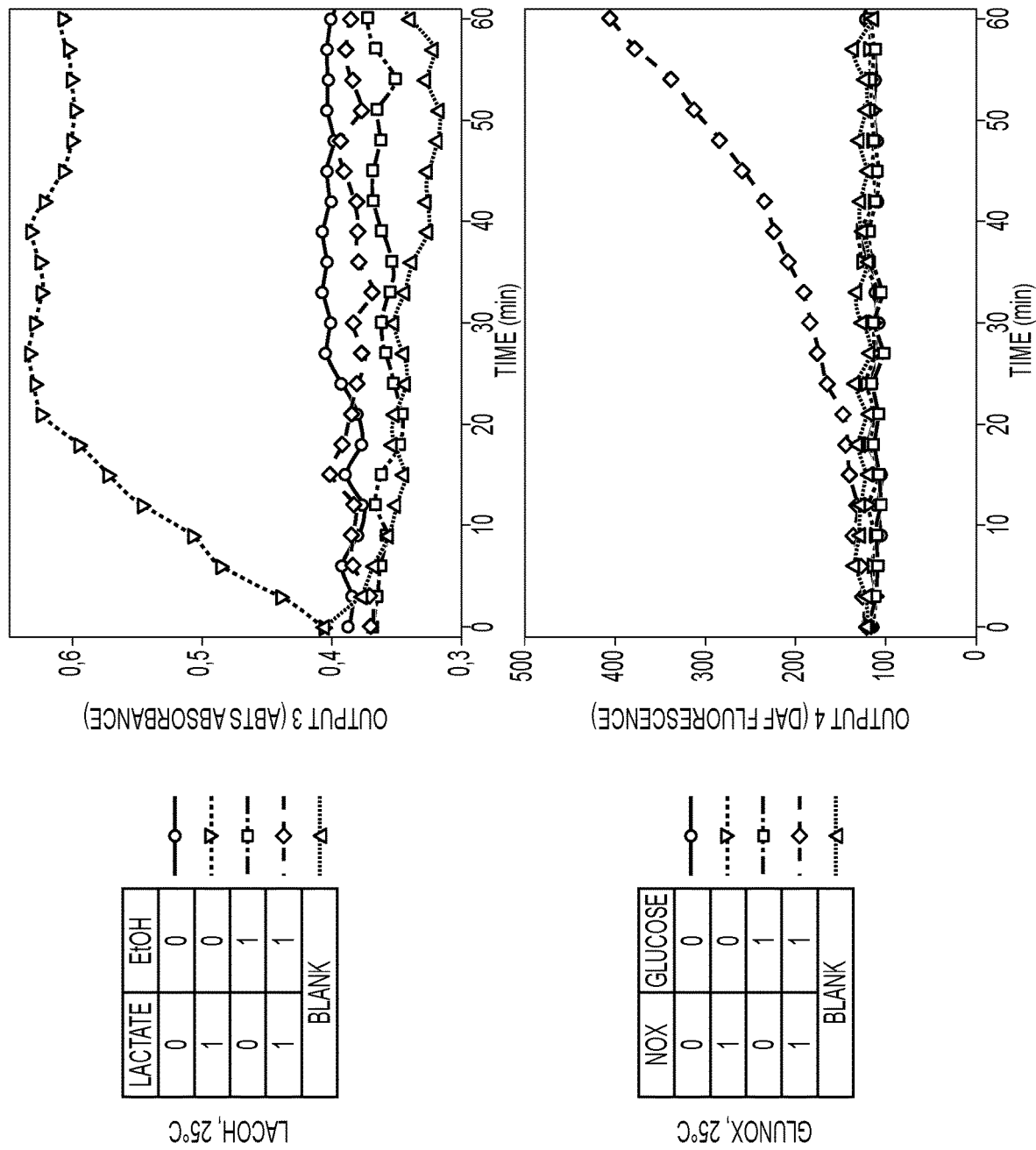

FIG. 11: Detailed experimental kinetic characterization of synthetic biochemical circuits in protocells.

Figure 12:
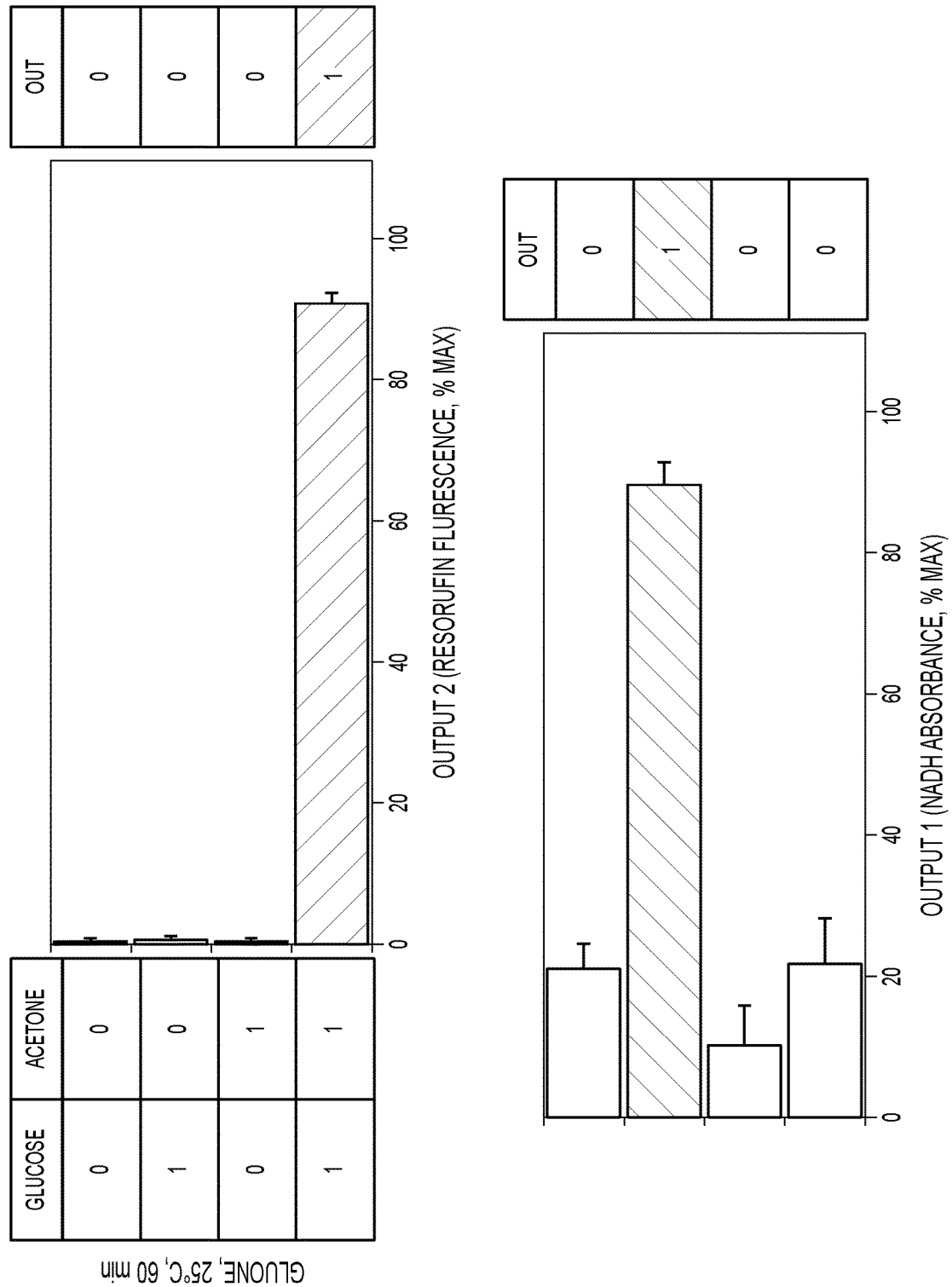
Figure 12:
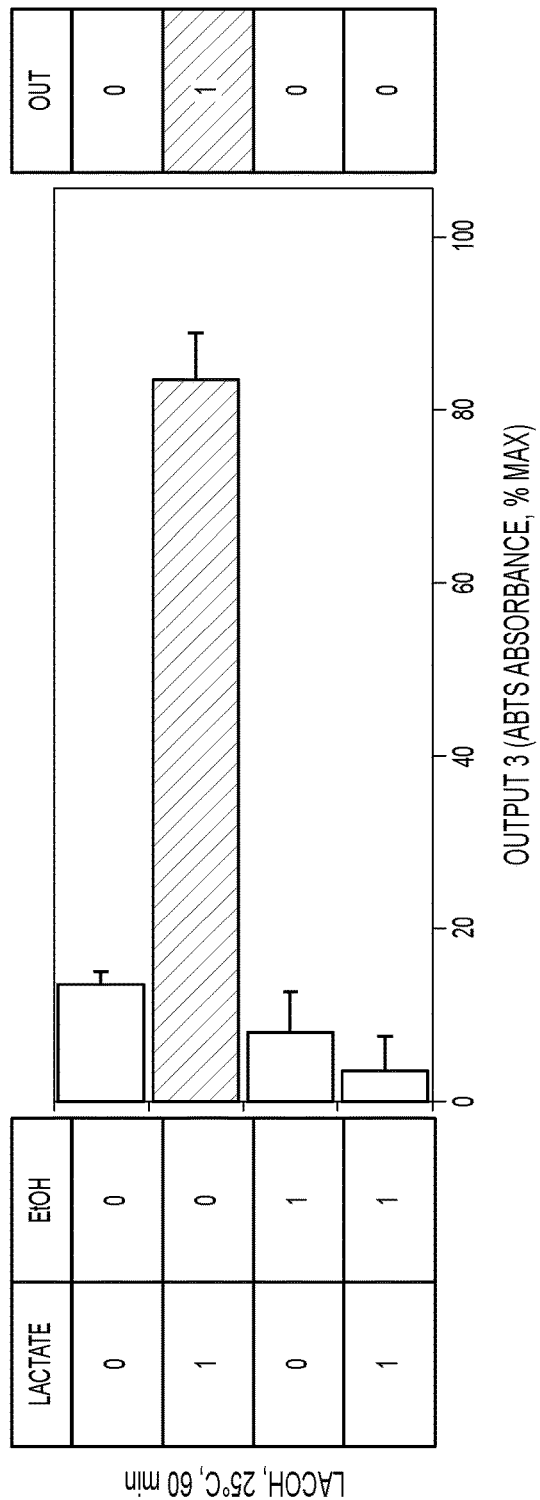
Figure 12:
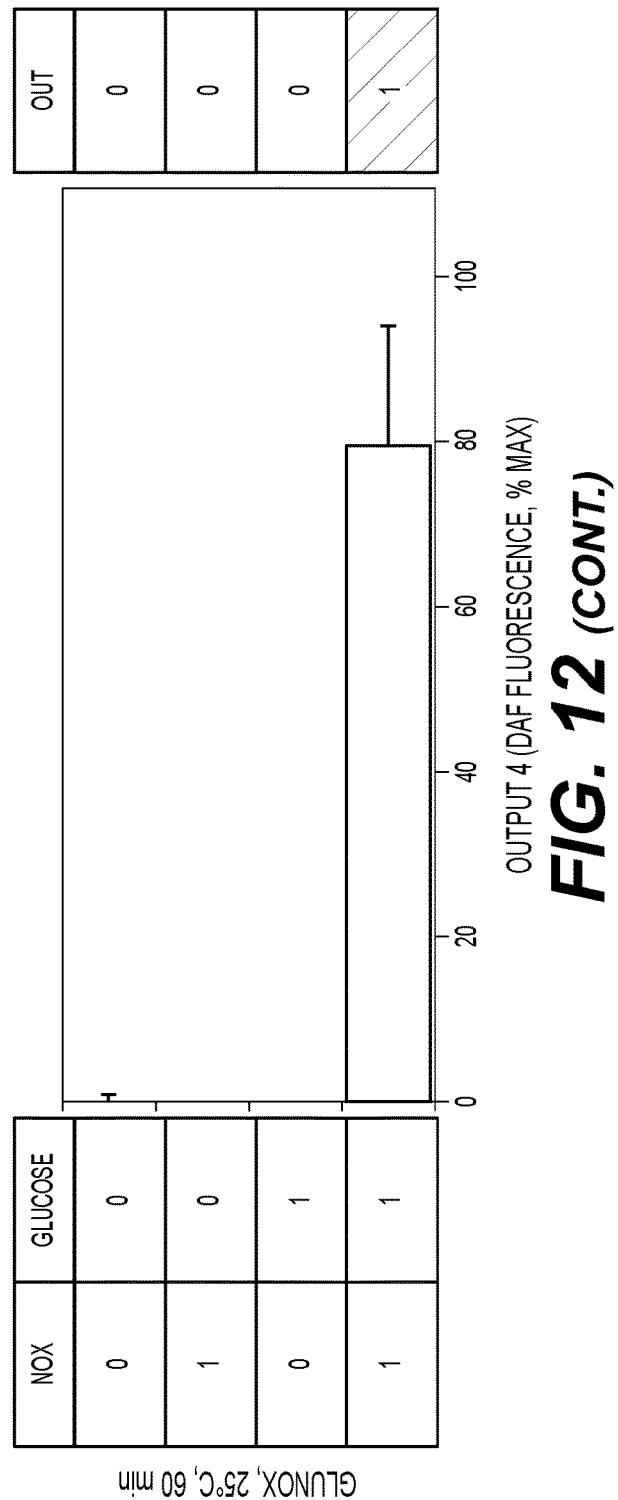

FIG. 12: Experimental truth tables of protosensors operating in PBS buffer.

Figure 13:
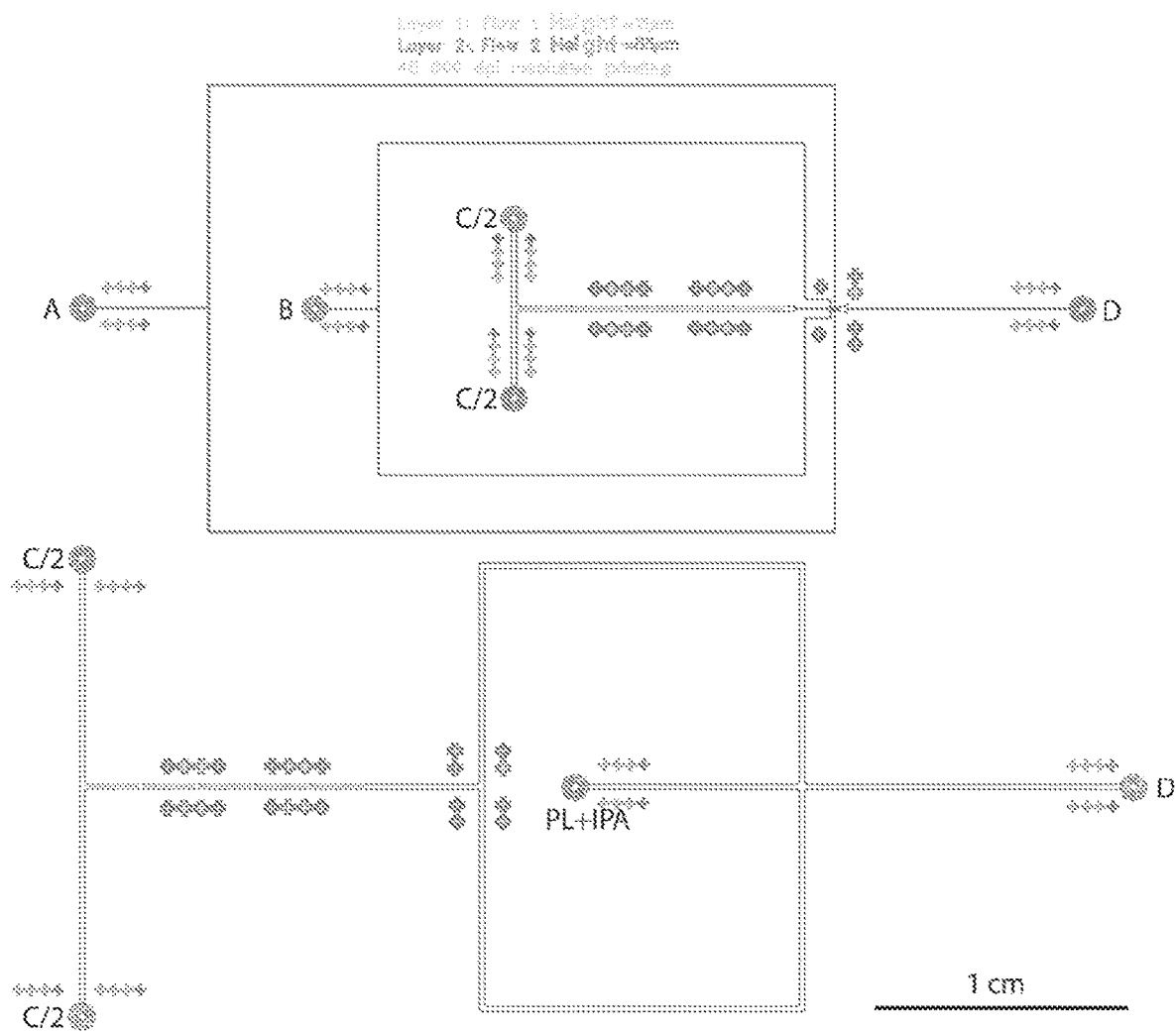

FIG. 13: Microfluidic chips used in this study to generate protosensors. (A) Buffer (10% v/v methanol, 15% w/v glycerol, 3% w/v pluronic F68 in PBS), 1 µl/min (B) DPPC dissolved in oleic acid, 0.4 µl/min (C) Enzymes in PBS, 0.4 µl/min (D) Out. Top: Double emulsion templating device, all experiments in this study were performed using this device. Bottom: Hydrodynamic flow focusing device. In this device, phospholipids are dissolved in an Isopropyl Alcohol buffer.

Figure 14:
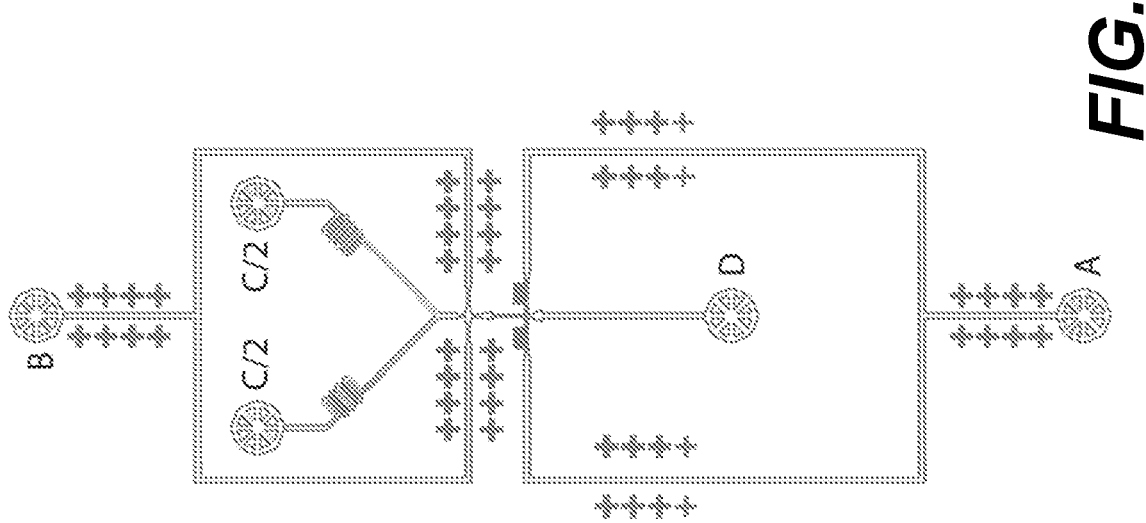
Figure 14:
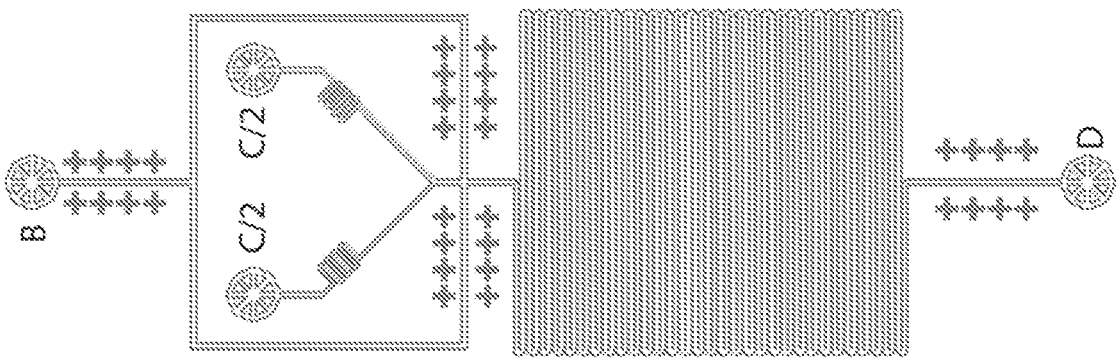
Figure 14:
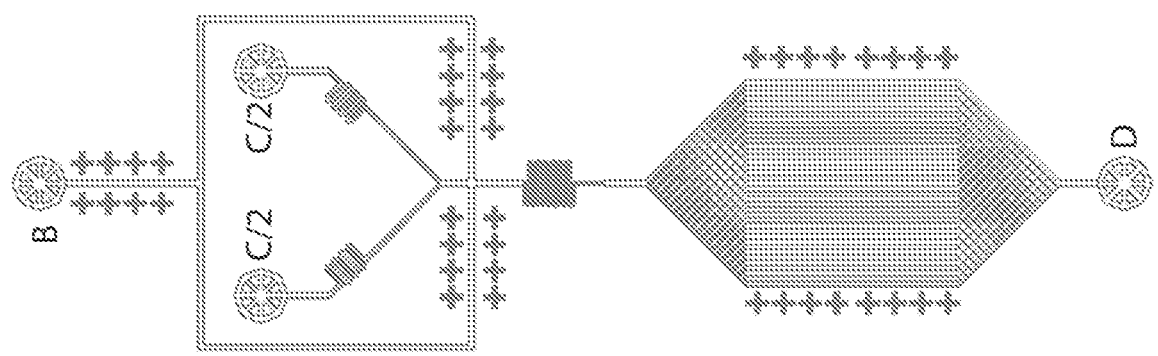

FIG. 14: Miscellanenous microfluidic chips used in this study. (A) Buffer (10% v/v methanol, 15% w/v glycerol, 3% w/v pluronic F68 in PBS), 1 µl/min (B) DPPC dissolved in oleic acid, 0.4 µl/min (C) Enzymes in PBS, 0.4 µl/min (D) Out. Left: Simple emulsion templating device. Used to generate and visualize the stability of simple emulsion in a built-it tank. This chip can also be used for two steps vesicle preparation, where the output of the chip is transferred in a solution containing buffer A. Middle: Same as previously, but the architecture of the tank differs. Right: Alternative two-step on-chip to produce vesicles. This device works as expected to produce protocells but is flowrates modes are more difficult to operate than the main chip we used in this study.

Figure 15A:
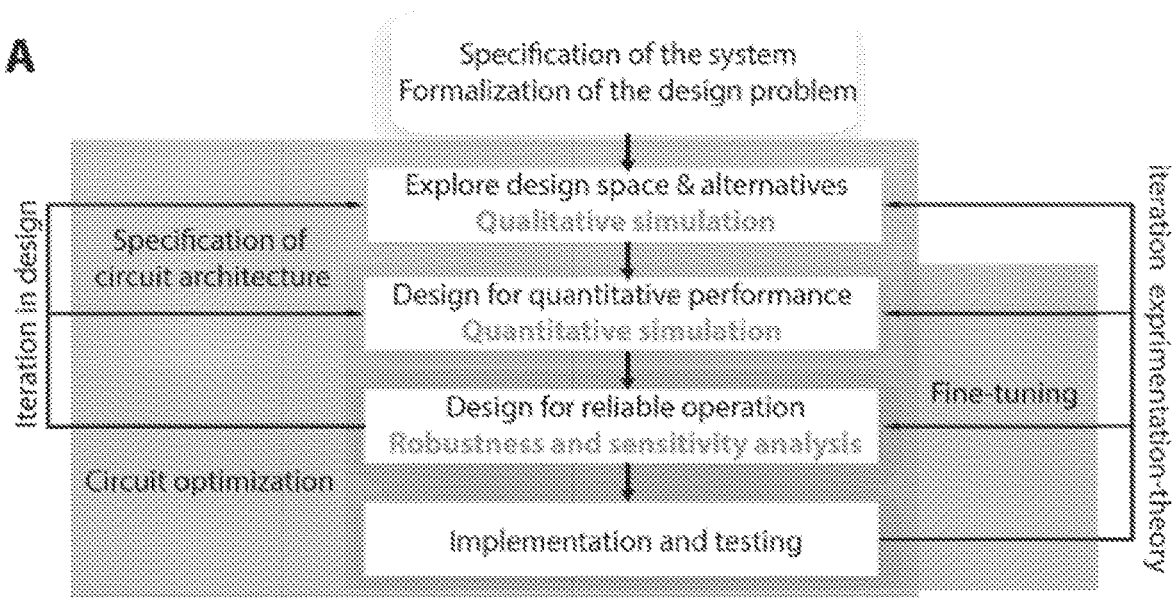
Figure 15B:
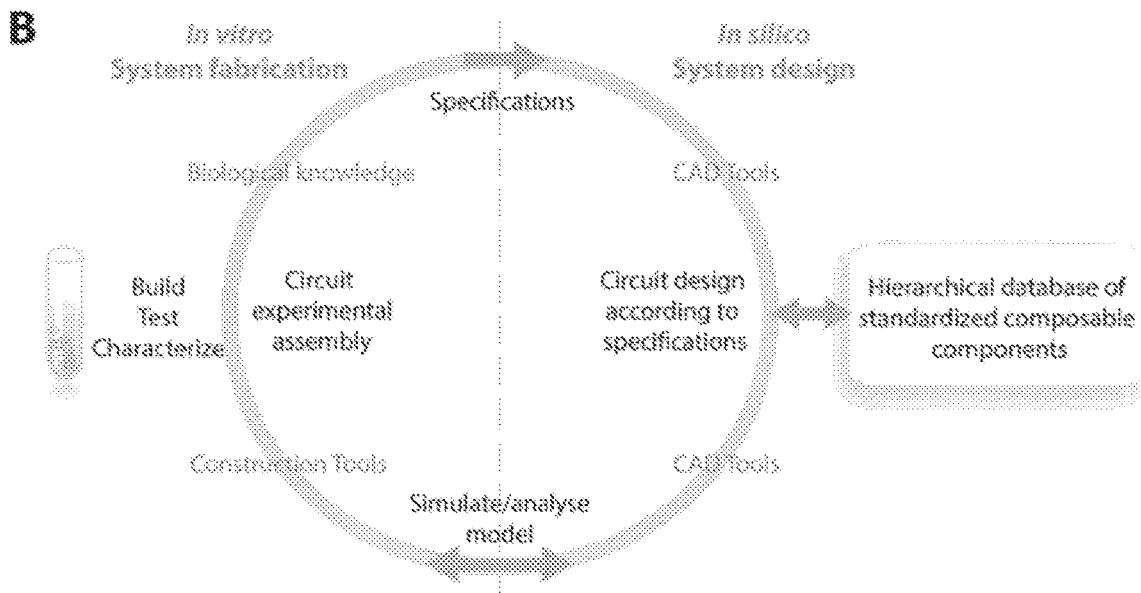

FIGS. 15A-15B: Computer-assisted design of synthetic systems. (A) Bottom-up engineering of biochemical circuits proceeds from formal specification of the systems behavior to in silico implementation and in vitro testing, with an iterative approach to design. (Adapted from Marchisio and Stelling (33)). (B) Iterative circle of system design to fabrication.

Figure 16:
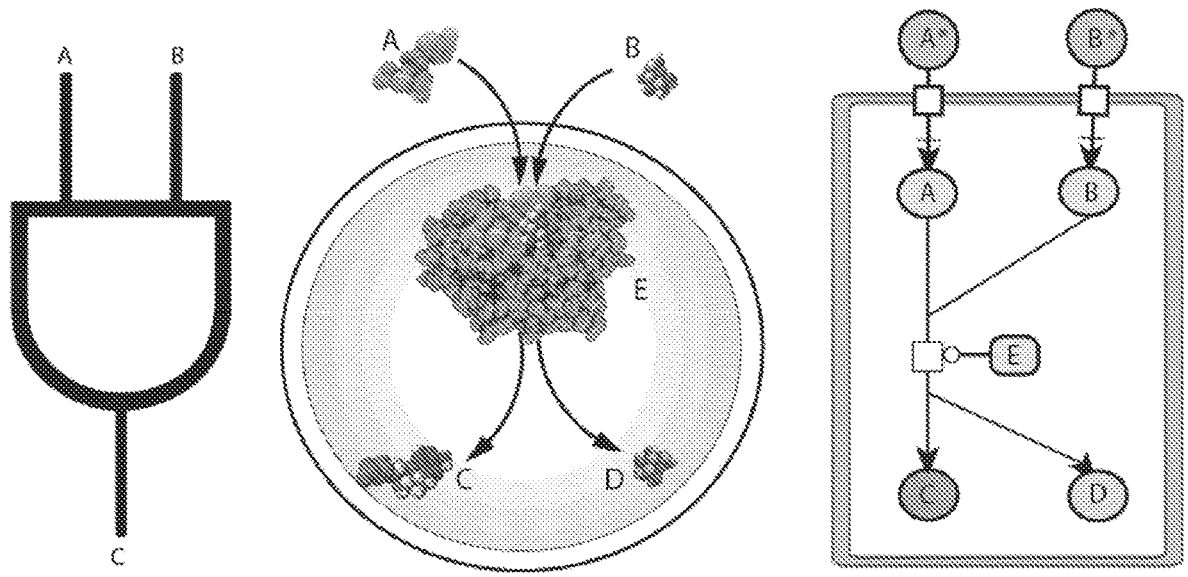
Figure 16:
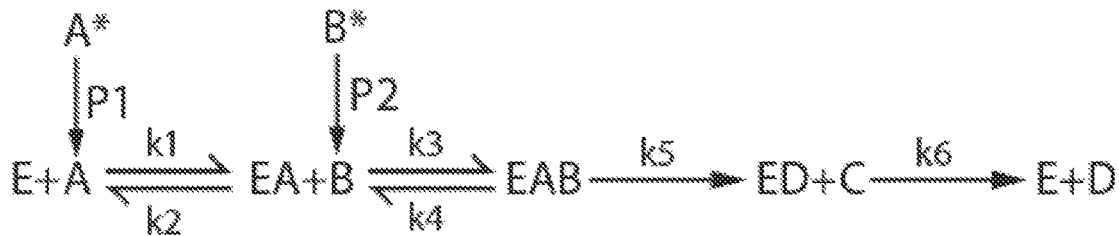

FIG. 16: Example of a model of an enzymatic circuit mimic an AND Boolean Logic gate inside a protocell, and example of a deterministic ODE model describing its operation.

Figure 17:
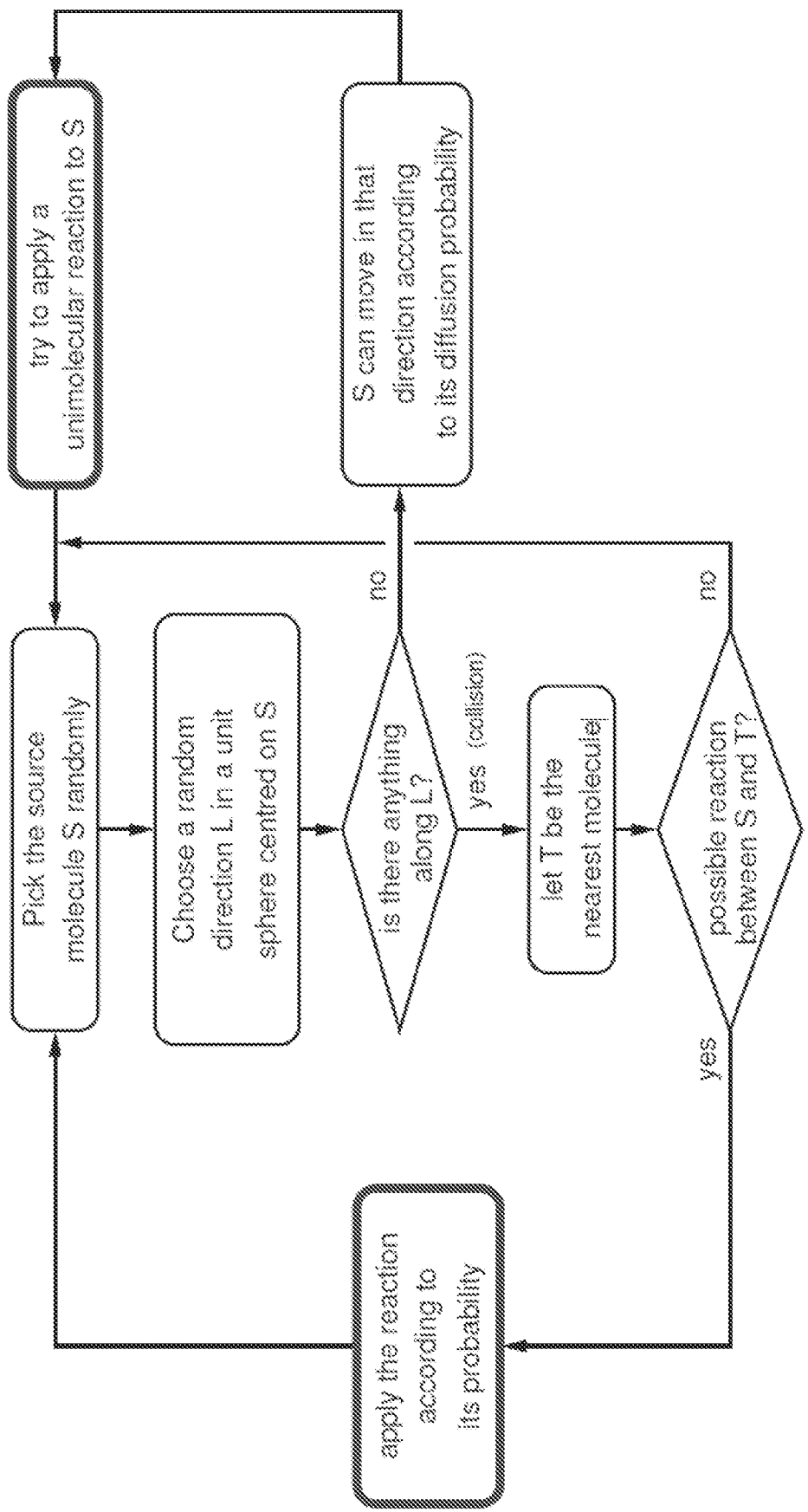

FIG. 17: Algorithm that HSIM performs at each time step for each molecule defined as entities.

Figure 18:
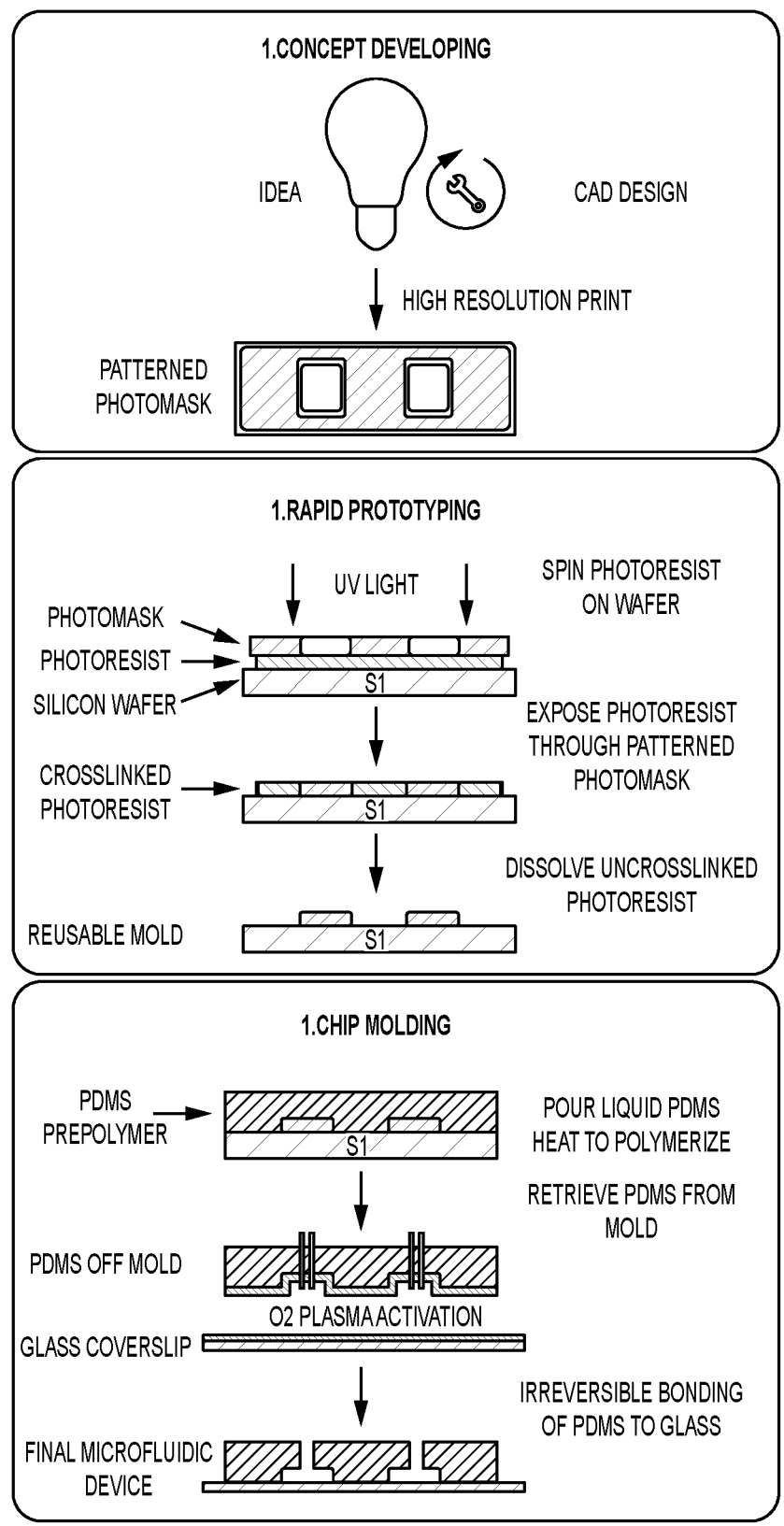

FIG. 18: Straightforward framework for PDMS chip manufacturing: from concept to realization.

Figure 19:
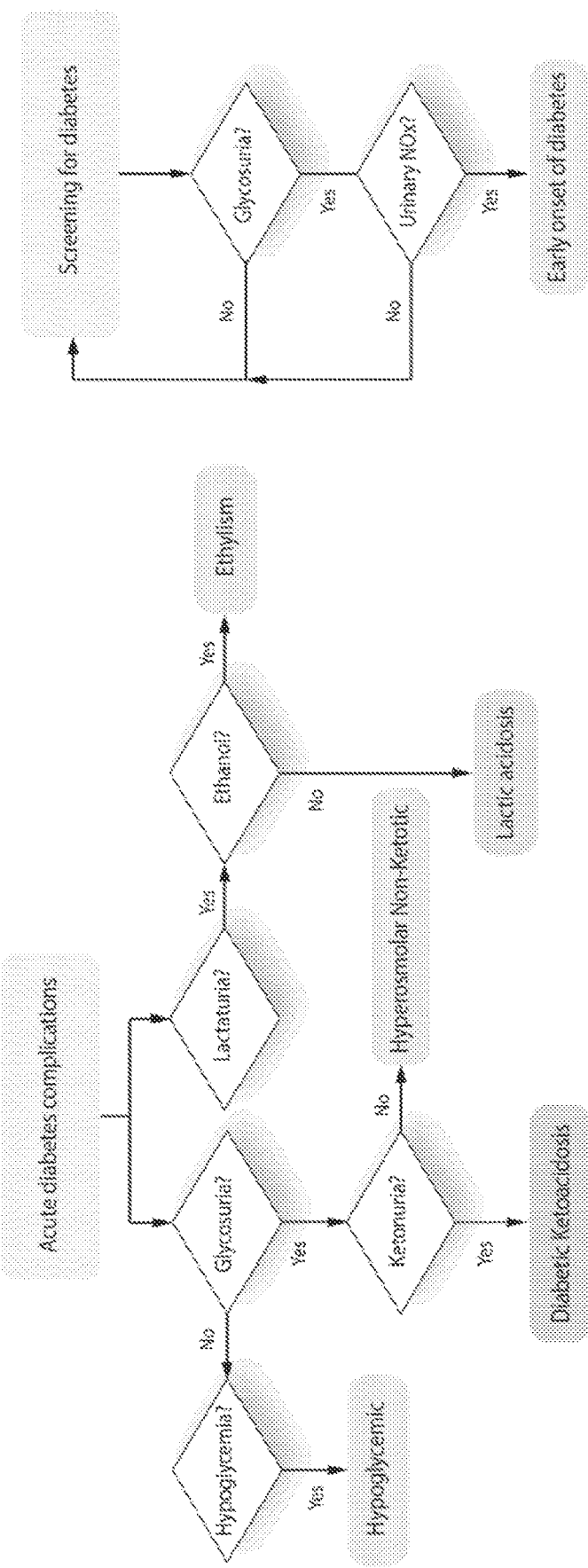

FIG. 19: Proof-of-concept diagnostic algorithm used in this study, and integrated within protosensors to achieve differential diagnosis of diabetes acute complications, and screening for diabetes. Diabetes associated acute complications, namely diabetic ketoacidosis, hyperglycemia hyperosmolar state, hypoglycemia and lactic acidosis, are clinical emergencies that represent a major health care burden associated with sever mortality, morbidity and frequent complications. Here we propose a diagnostic algorithm enabling diagnosis of these complications, as well as a proof-of-concept screening assay, from markers present in urines.

Figure 20A:
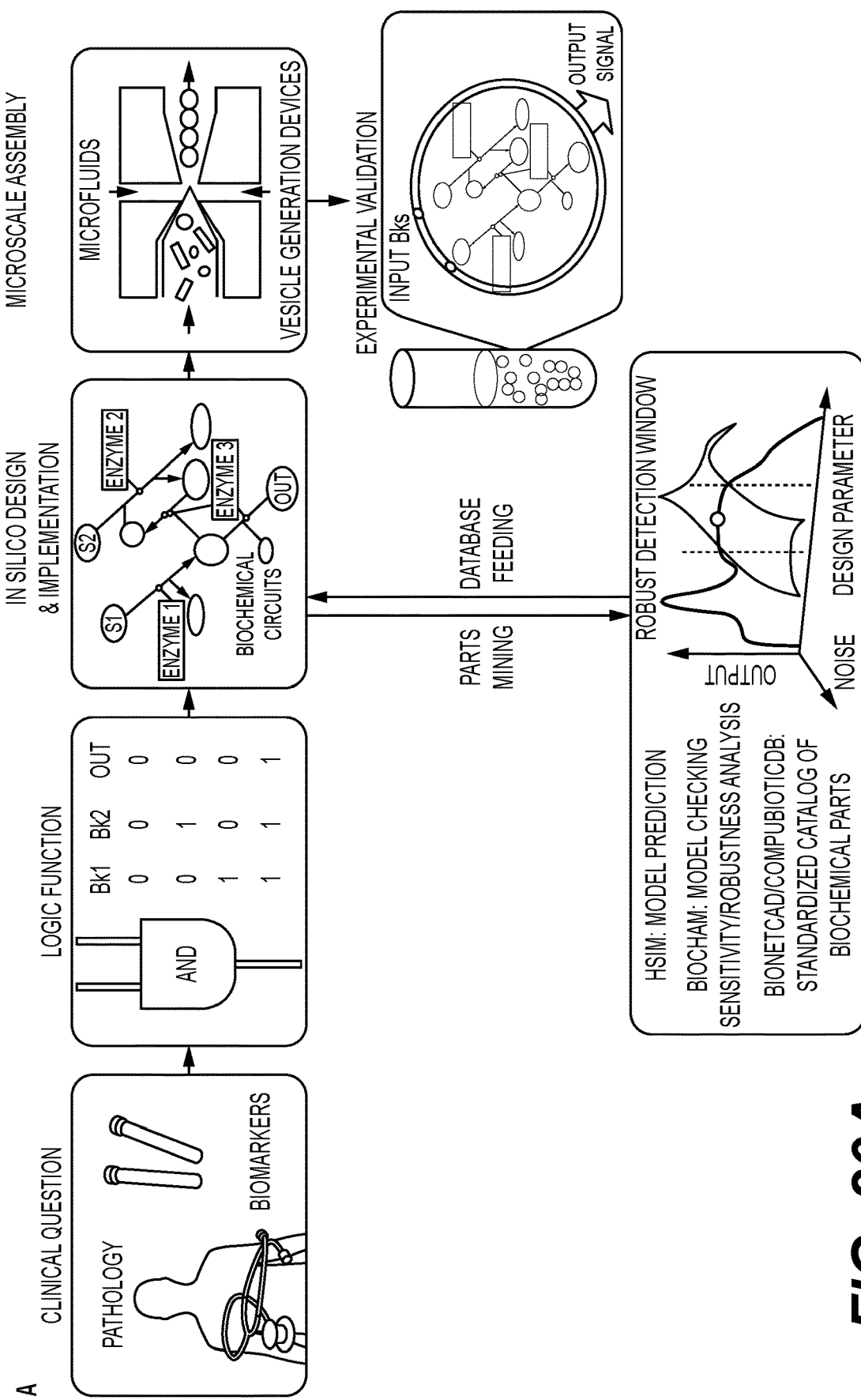
Figure 20B:
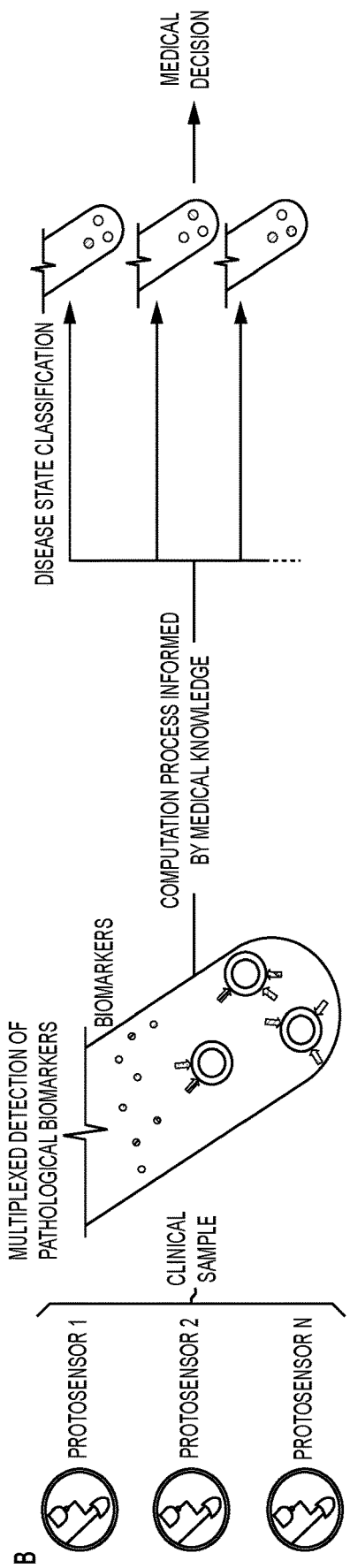

FIGS. 20A-20B: General design methodology, architecture and operational principle of protosensors for medical diagnosis. (A) Arising from a clinical need to detect pathologies associated with patterns of specific biomarkers, medical diagnosis can be abstracted to a computational process formalized using Boolean logic in vitro and embedded into synthetic biochemical circuits. This de novo circuits can be assembled, or programmed in silico from naturally occurring building blocks, and encapsulated in synthetic containers to yield diagnostic devices, or protosensors, capable of detecting patterns of specific biomarkers in human clinical samples and integrates these signals in a medical decision algorithm. If a pathological pattern of biomarker is detected, the protosensor generates a colorimetric output. (B) Different types of protosensors corresponding to different clinical questions can be used at the same time to enable multiplexed detection of pathological biomarkers and achieve differential diagnosis of pathologies in clinical samples.

FIGS. 21A-21C: In silico design, simulation and experimental validation of synthetic biochemical circuits for medical diagnosis. (A) Formal Boolean description depicted using basic logic gates symbols, In silico circuits implementation with biochemical parts, and theoretical truth tables for the three models (B) HSIM simulation, (C) In vitro circuits implementation and experimental measurements and comparison with HSIM predictions.

Figure 22:
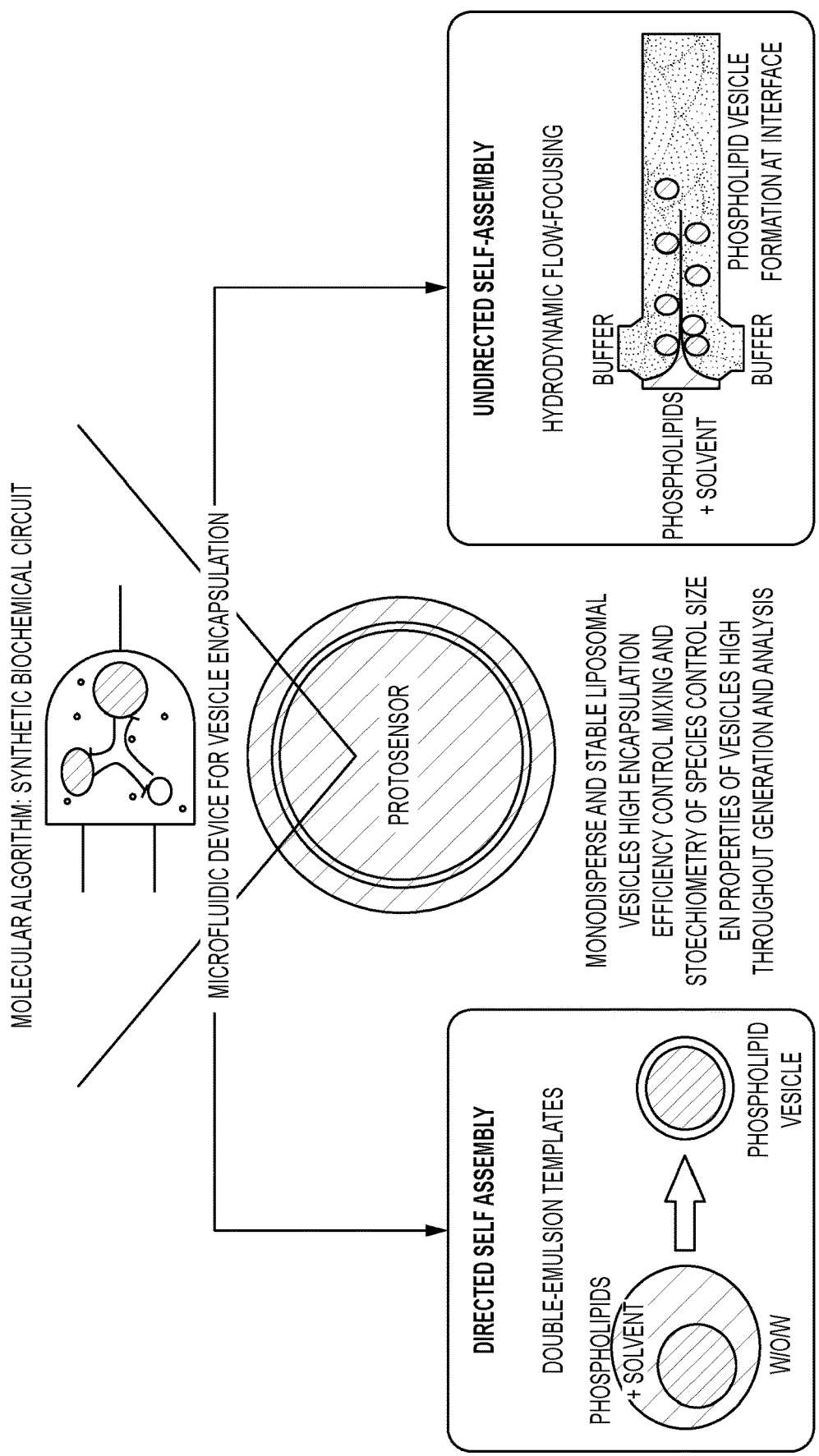

FIG. 22: Microfluidic approaches explored in these Examples to achieve controlled and high-throughput protocell fabrication.

FIGS. 23A-23C: Double emulsion template for protosensor fabrication. (A) Chemical structure of Dipalmitoylphosphatidylcholine (DPPC) (B) The microfluidic flow-focusing droplet generation device generates double emulsion templates, and Oleic acid is then extracted to generate protosensors. (C) Visualization of the extraction process at 0, 1, 2 and 3 hours (Scale bar=2.5 µm).

Figure 24:
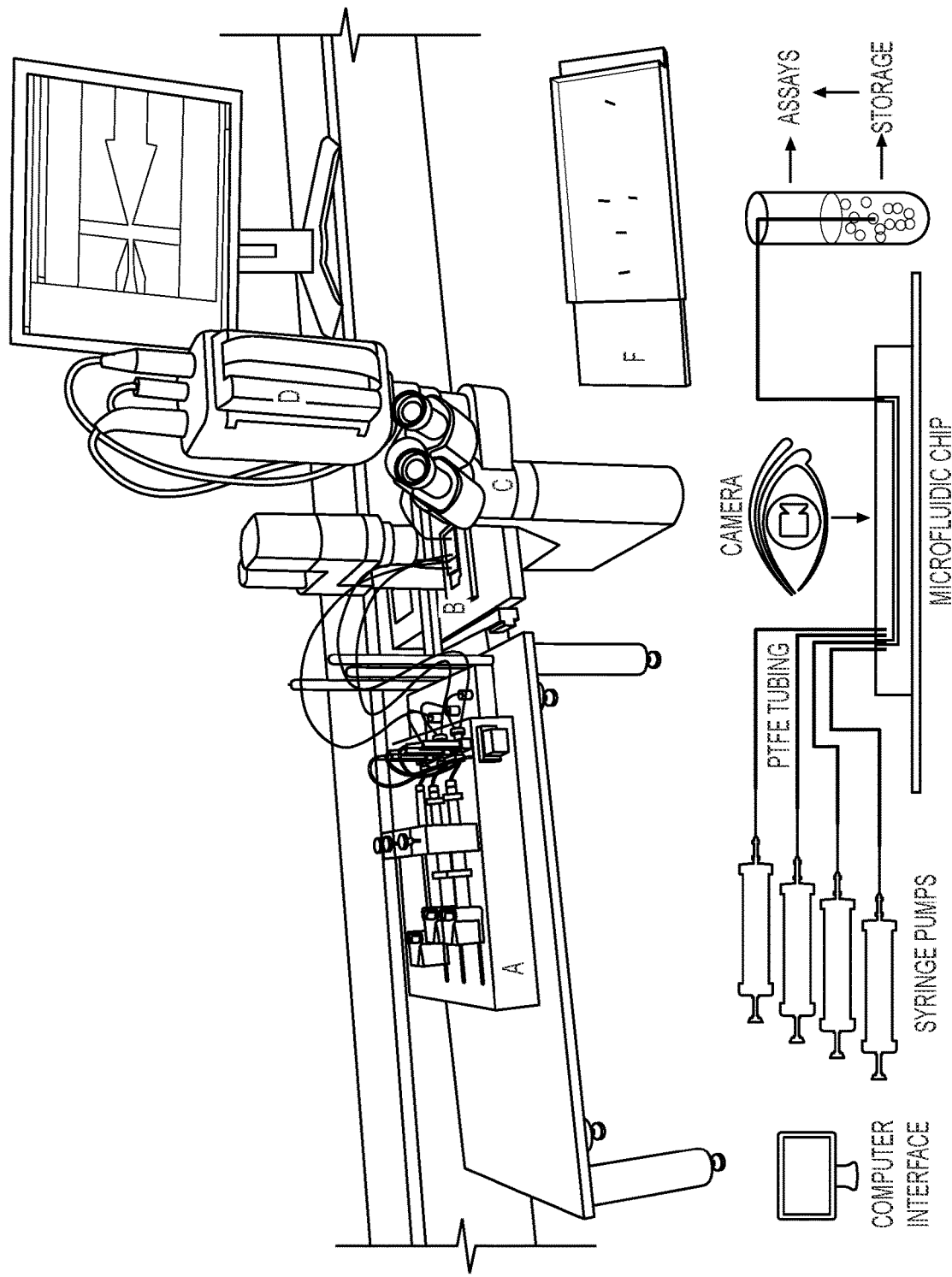

FIG. 24: Experimental setup for microfluidic production of protocells. (A) Syringe pumps enable displacement driven flow in the microfluidic device (B). Protocell formation is under microscopic control using an inverted microscope (C) mounted with a ultrafast camera (D). A computer interface enables to visualize in real time the fabrication process (E), and gives nanometric control on syringe pumps flow rates. (F) Photograph of the PDMS chip used in these Examples to generate protocells.

Figure 25A:
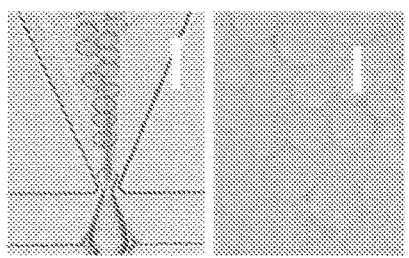
Figure 25A:
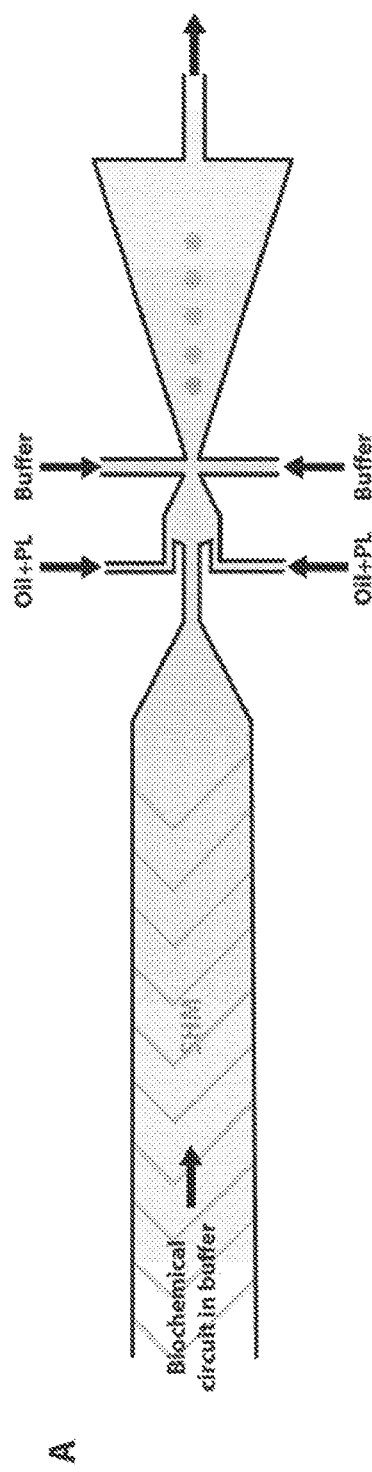
Figure 25B:
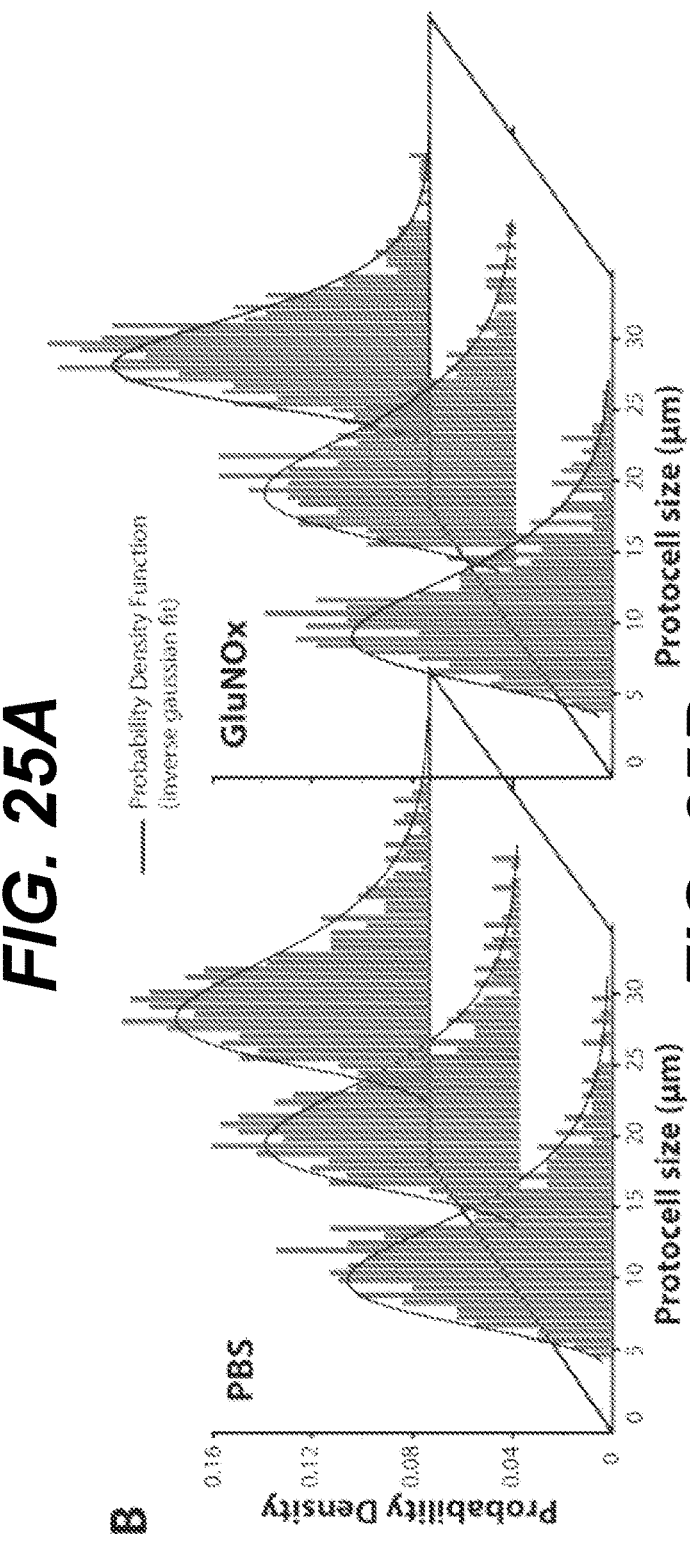
Figure 25C:
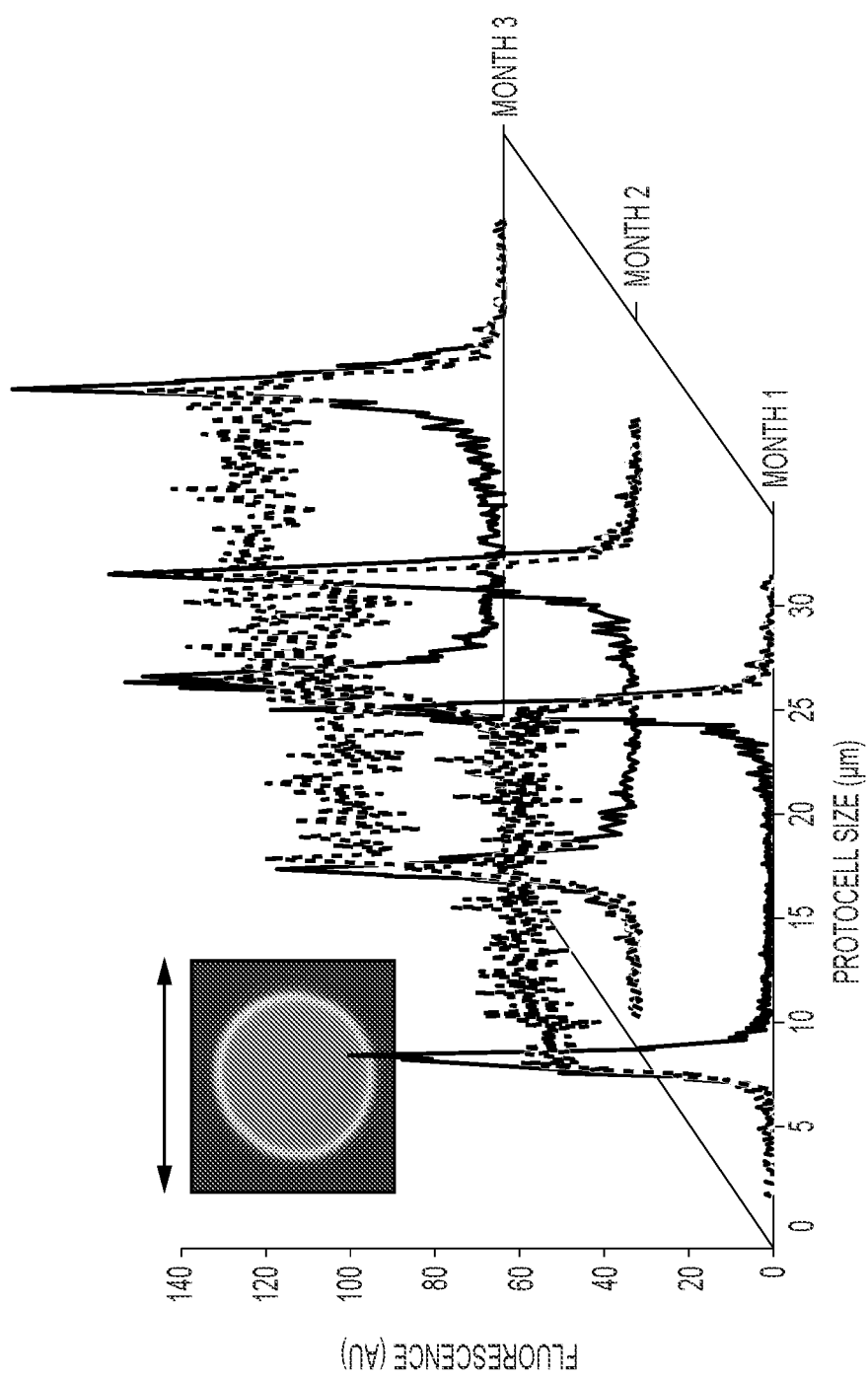

FIGS. 25A-25C: Experimental construction of protosensors using microfluidics. (A) Left: Double emulsion template microfluidic device architecture and operation. This method relies on the generation of W/O/W double emulsions. Buffer: 10% v/v methanol, 15% w/v glycerol, 3% w/v pluronic F68 in PBS (1 µl/min) Oil+PL: DPPC dissolved in oleic acid (0.4 µl/min) Biochemical circuit buffer: enzymes and metabolites in PBS (0.4 µl/min). Right: microscopic validation of protosensor generation on chip (Top, scale bar=20 µm), bright field optical validation of protosensors isolated for subsequent analysis (Bottom, scale bar=10 µm). (B) Size dispersion and stability of protosensors generated with the microfluidic method, after encapsulating PBS (left) and GluNOx network (right). (C) Months long stability of encapsulation. AlexaFluor-488 labeled IgG where encapsulated in protocells and fluorescence was then monitored by confocal microscopy for three months. Yellow: protocell membrane fluorescence as labeled with phospholipid dye DiIC18. Blue: AlexaFluor-488 labeled IgG fluorescence.

Figure 26A:
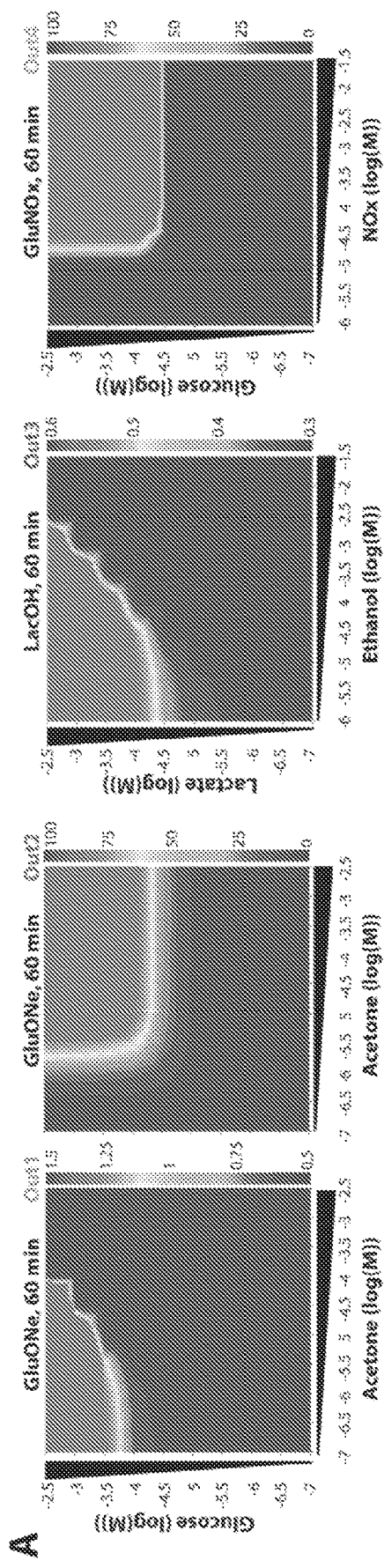

FIGS. 26A-26B: In silico and experimental validation of analytical properties of protosensors. (A) Heat maps depicting computed output signals at 60 minutes using HSIM models simulations, for the 3 different systems after induction with increasing biomarker concentration (B) Experimental validation of computer prediction at the single (proto)cell level using flow cytometry. For LacOH, in order to get a fluorescent output signal measurable with a flow cytometer, we exchanged ABTS with Resorufin, which are analogous.

FIGS. 27A-27D: Experimental validation of medical protosensors robust multiplexed biosensing and logic. (A) Confocal microscopy validation of "ON" output signals responses at 60 minutes after induction with respective biomarkers. From top to bottom: GluONe (Out1, Out2), LacOH (Out3), GluNOx (Out4). The phospholipid bilayer is stained in yellow using the dye DiC18. For LacOH, in order to get a fluorescent output signal measurable in confocal microscopy we exchanged ABTS with Resorufin, which are analogous. (B) Experimental truth tables of protosensors operating in human urines. (C) Multiplexing Logic: example of comparison between expected (valid analytical response according to molecular inputs present in the sample), batch mode analysis (non-encapsulated synthetic circuits) and protosensors analysis (encapsulated synthetic circuits). PBS media was spiked with multiple biomarkers (in this case, acetone, ethanol and nitric oxides or glucose, acetone and lactate), and output signals were measured at 60 minutes (D) Flow cytometry evaluation of protosensors structural robustness in urines. GluONe protosensors were induced and incubated for 2 hours at 25° C. in human urine, and analyzed using flow cytometry while recording Resorufin fluorescence and forward scattered light.

Figure 28:
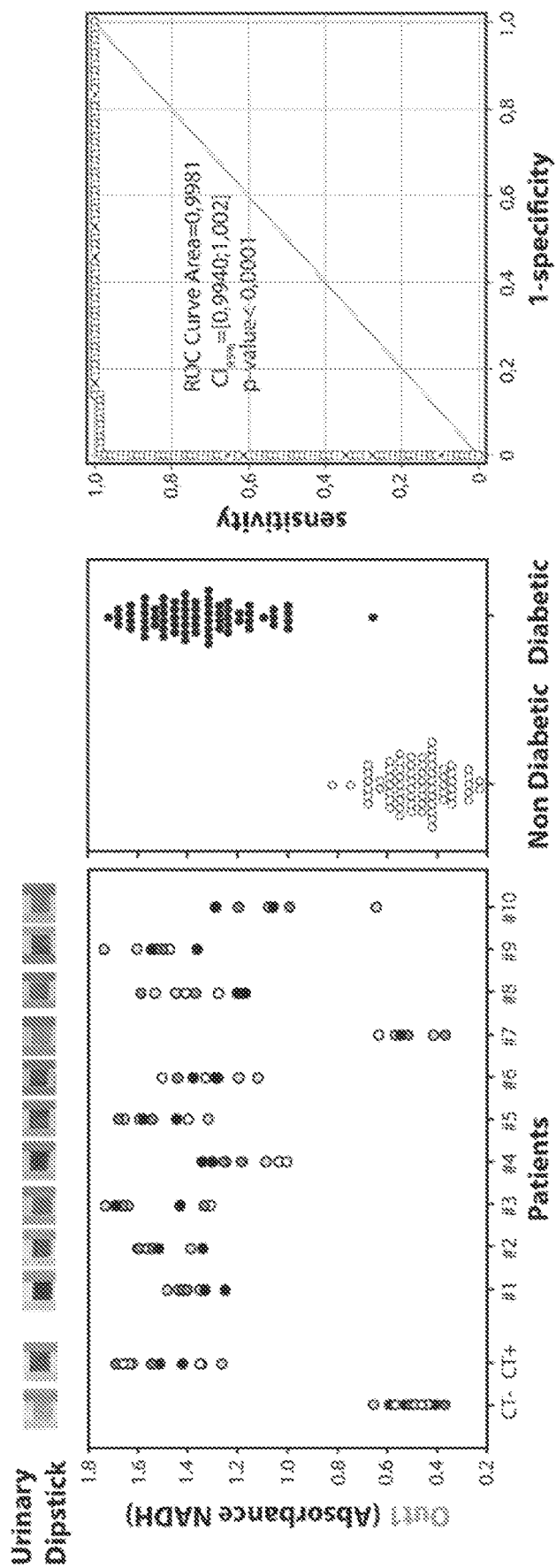

FIG. 28: Protosensor mediated detection of pathological glycosuria in patient clinical samples. Left: Dot histogram of data used for statistical analysis. Right: Receiver Operating Characteristic (ROC) analysis curve depicting statistic sensitivity versus (1-specificity). A set of 72 measurement performed in non-pathological urine were compared to 72 measurements performed in urine from diabetic patients. We used GluONe protosensors for this assay, and measured Out1 signal (NADH absorbance) after 60 minutes.

Figure 29A:
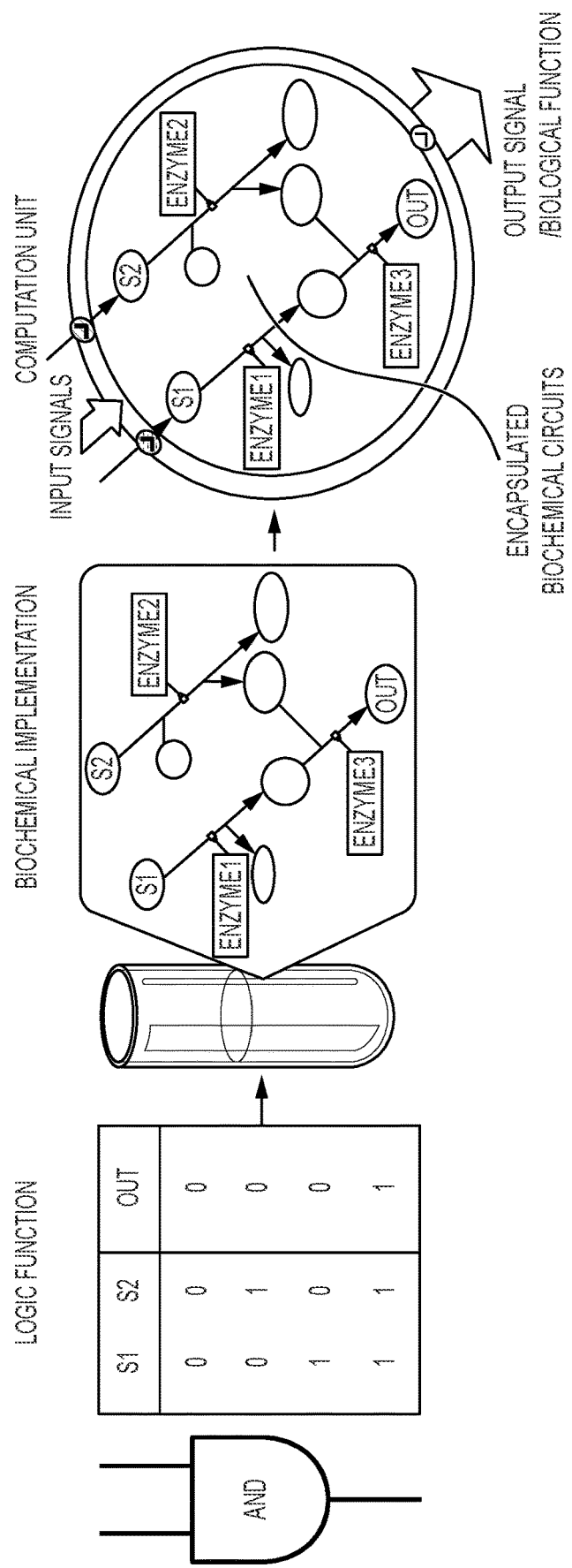
Figure 29B:
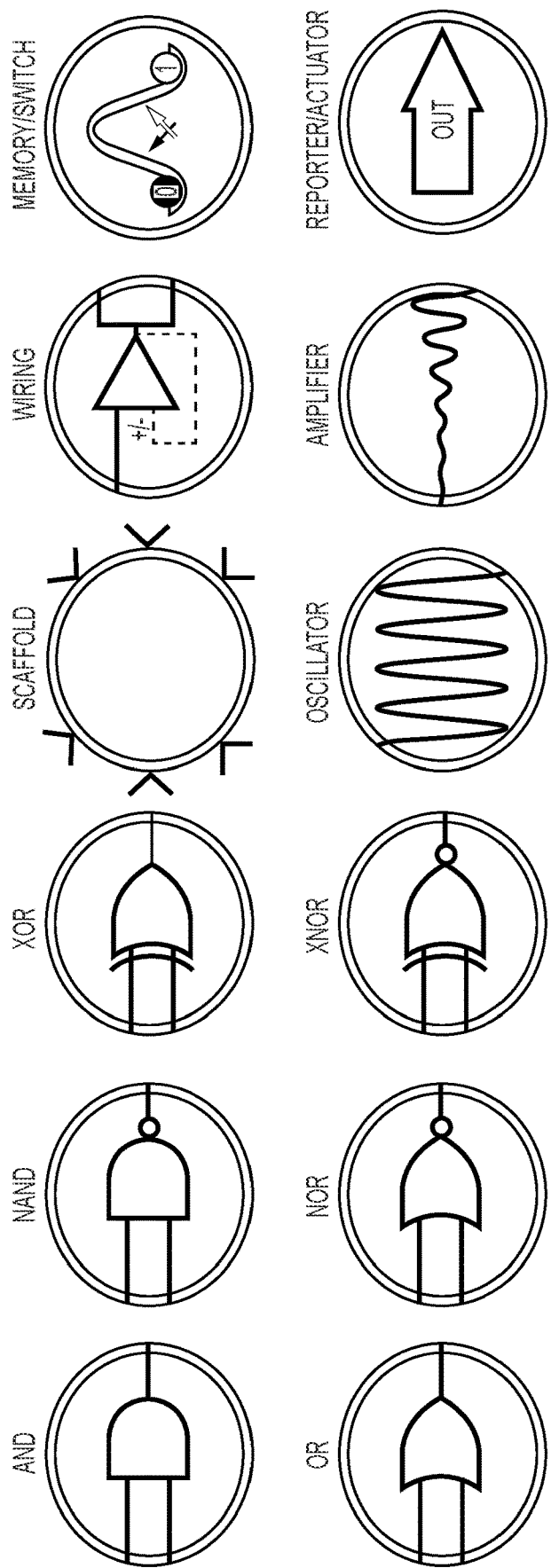

FIGS. 29A-29B: (A) Rational design of a computation unit implementing a given logical function. (B) Different types of computation units. An AND gate outputs true only if the two inputs are true; An OR gate outputs true if at least one of the inputs is true; A XOR gate outputs true only when one of the inputs is true; The NAND, NOR and XNOR gates outputs the opposite value of the AND, OR and XOR gates respectively.

Figure 30:
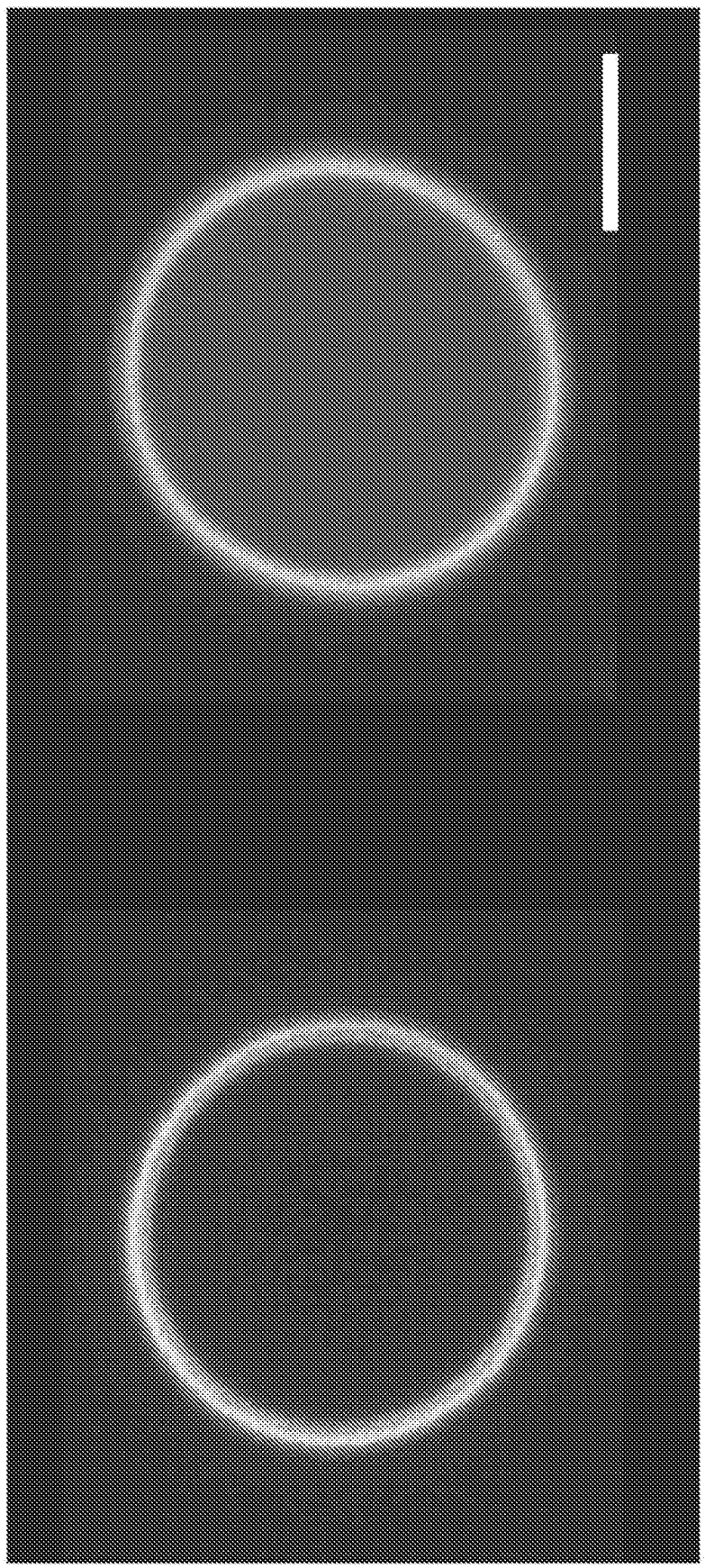

FIG. 30: Example of experimental fluorescence signal triggered in micrometric protocells. Enzymatic electron transfer from carbohydrate to the redox sensor probe (in that case resazurin is reduced into the red fluorescent product resorufin). Phospholipidic protocells encapsulating biochemical species were generated using microfluidic devices, and imaged using a confocal microscope. Left no induction; right induced with glucose (scale bar=5 µm).

Figure 31:
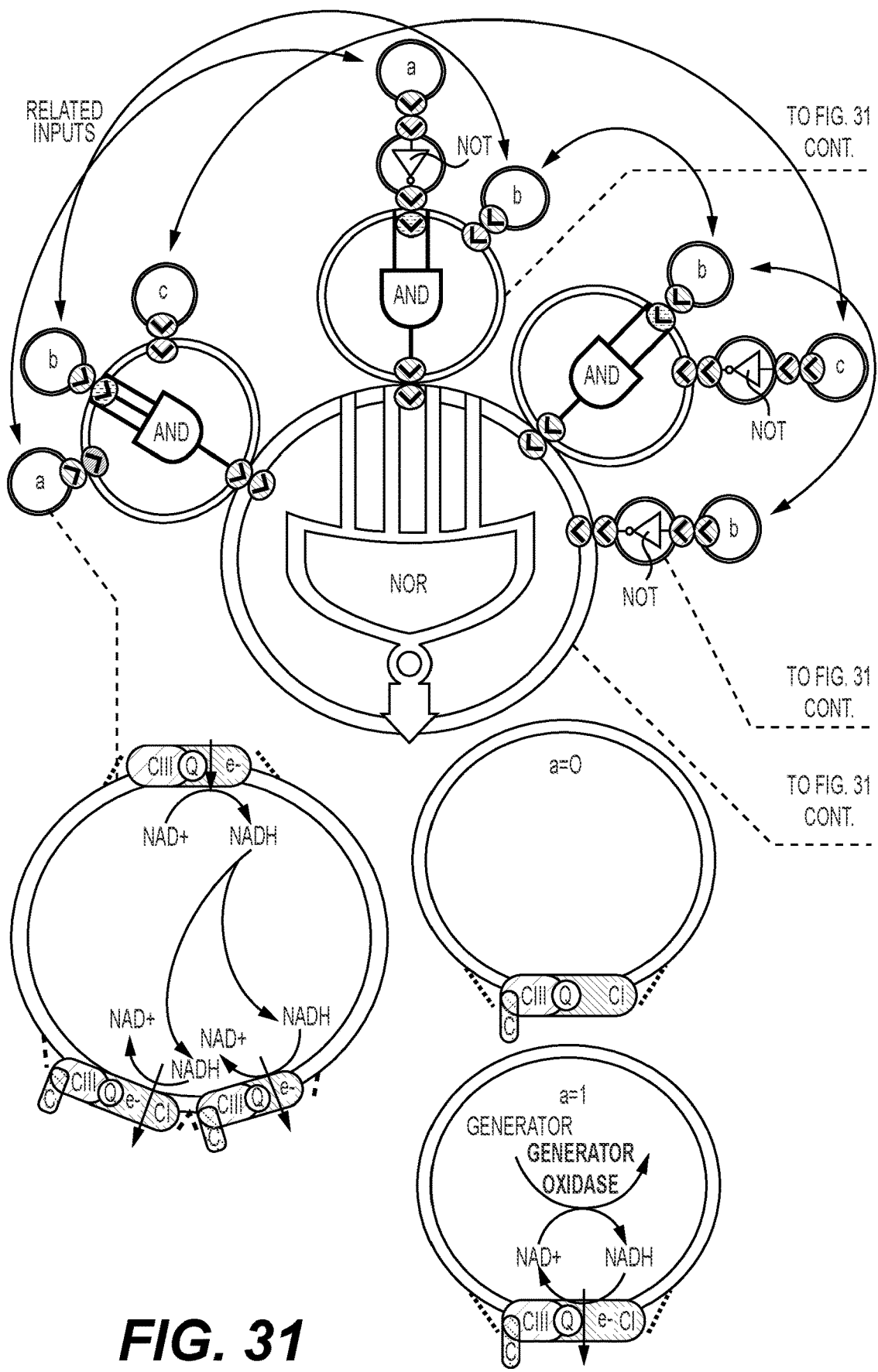
Figure 31:
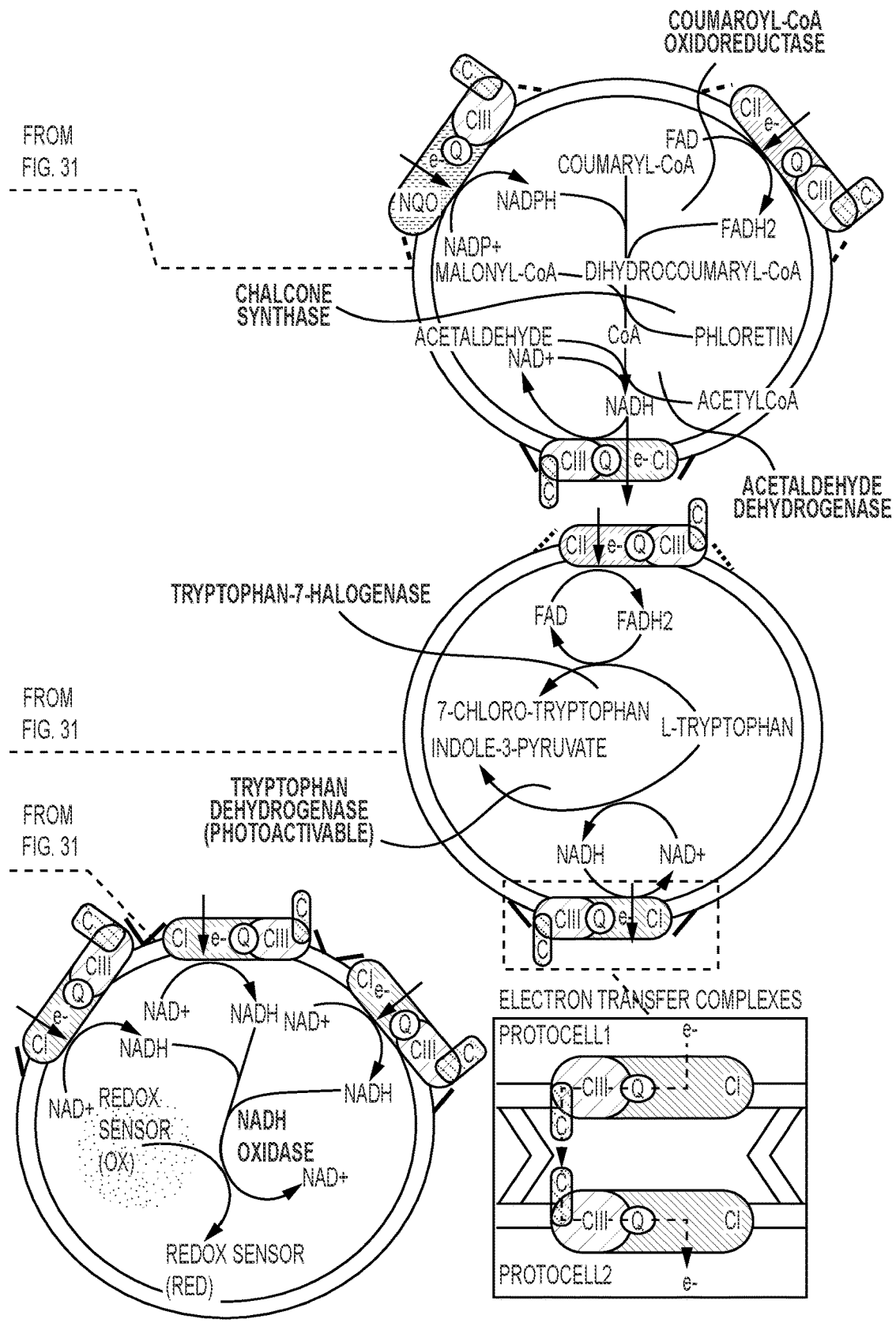

FIG. 31: Detail of a possible implementation of each type of protocell gate. Each type of logic gates has been simulated in silico with HSIM, and some of them are under test in the lab). The detail of the electron transfer mechanism is shown in the bottom right cartoon. For example, the fluorescent NOR gate uses a cascade of two enzymatic reactions (NADH oxidase, Horseradish Peroxidase) to consume the fluorescent oxidised scopoletin when NADH is present in the protocell, that is when at least one input is set to true, so is transferring electrons to make NADH from the initial pool of NAD+.

Figures 32A, 32B:
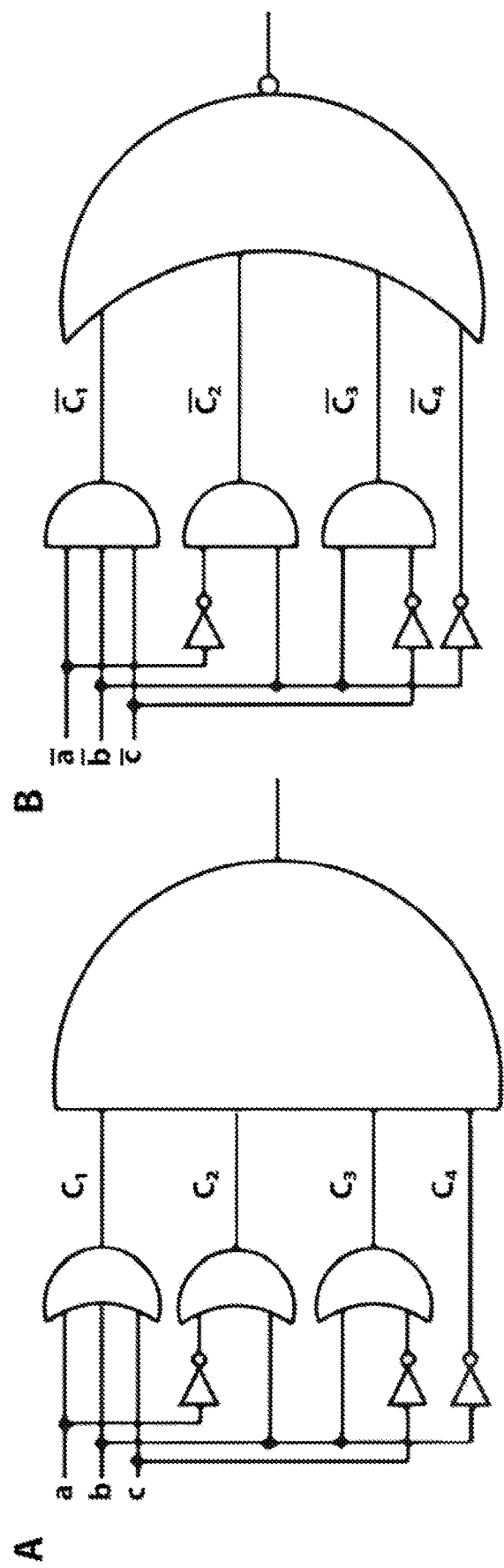

FIGS. 32A-32B: (A) Direct implementation of the G formula in standard Conjunctive Normal Form. (B) Using the De Morgan laws, the same Boolean function is rewritten using a NOR gate instead of the final AND gate, easier to build with a large number of inputs, and multiple 2- and 3-inputs AND gates fed with the complement of the original inputs.

Figure 33:
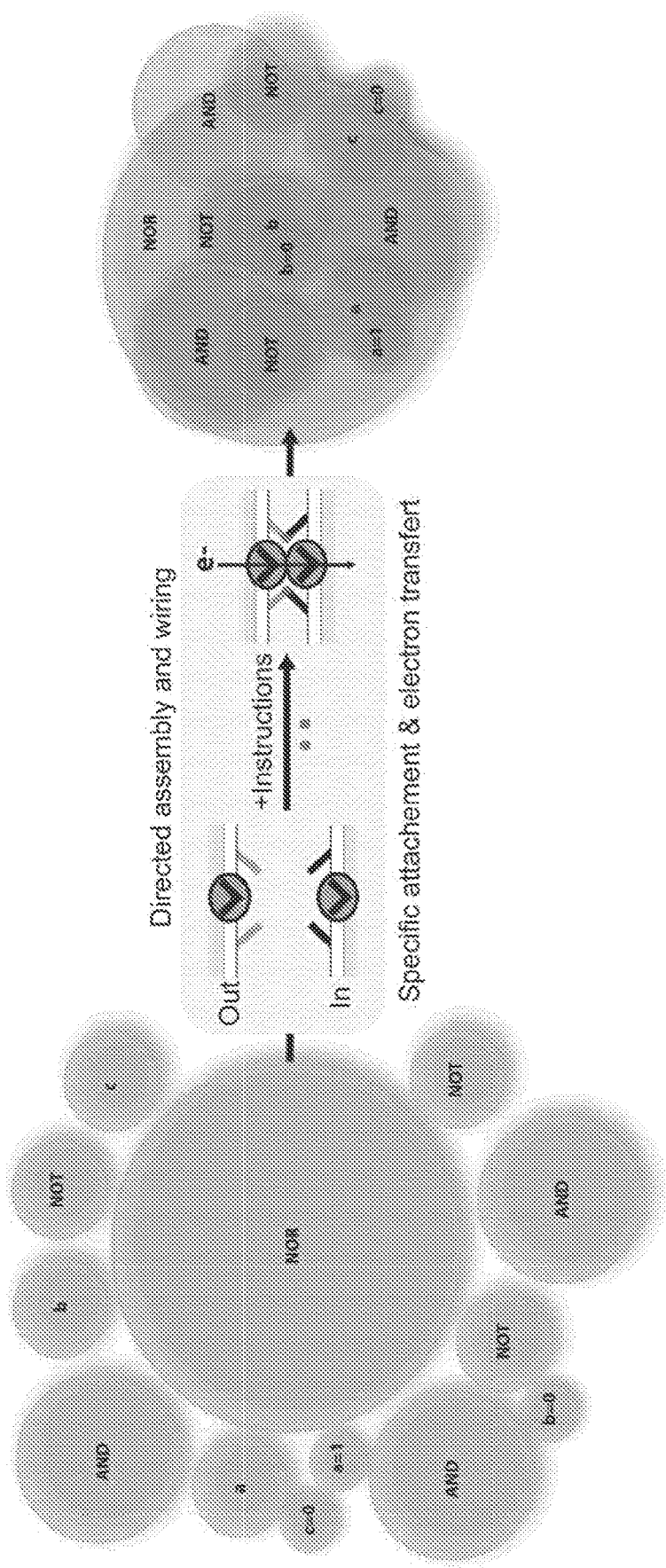

FIG. 33: Directed assembly and wiring via specific attachments of one instance of a protocellular machine for the formula G (a, b, c). The inputs a, b and c are implemented with wiring protocells (one input, one, two or more outputs) that distributes the values of the variables to inverters or to the NAND gates according to the formula (3), see FIG. 32B. The NOR gate is a large protocell underneath the AND gates, where the outputs of the AND gates are bound. The small protocells a; b; c=0; 1 are constant protocells for the input variables a, b and c (left). These input protocells will be randomly bound to constant false or true protocells to cover all the valuations of the variables. On the right side, the protocellular machine assembled tests the valuation a=1; b=0; c=0

Figure 34:
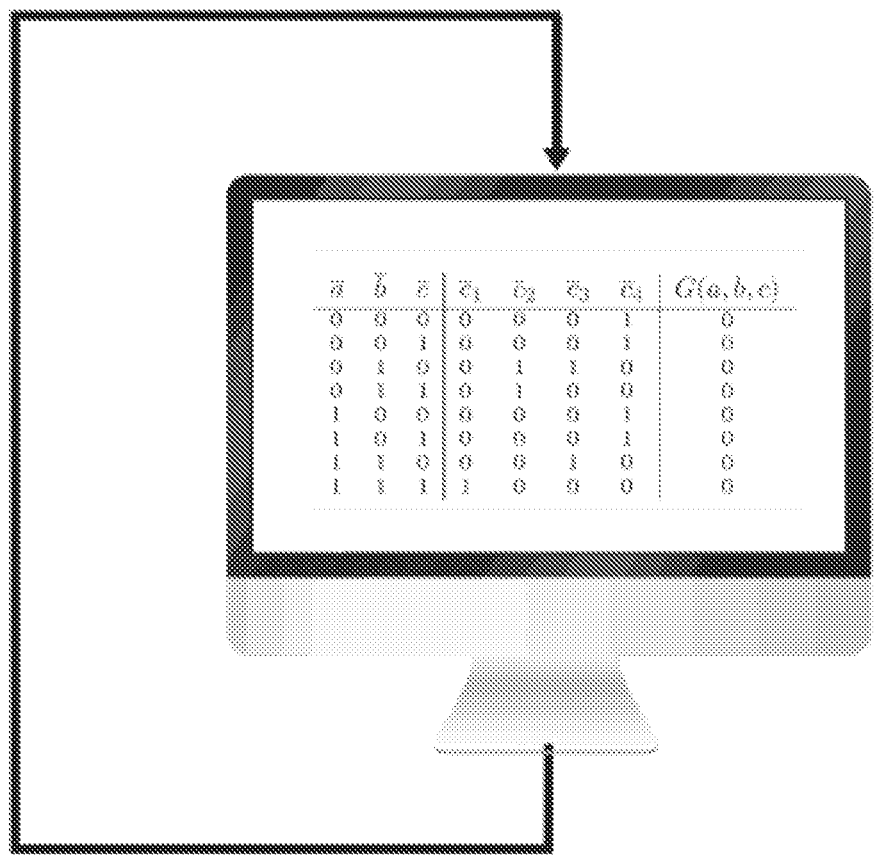
Figure 34:
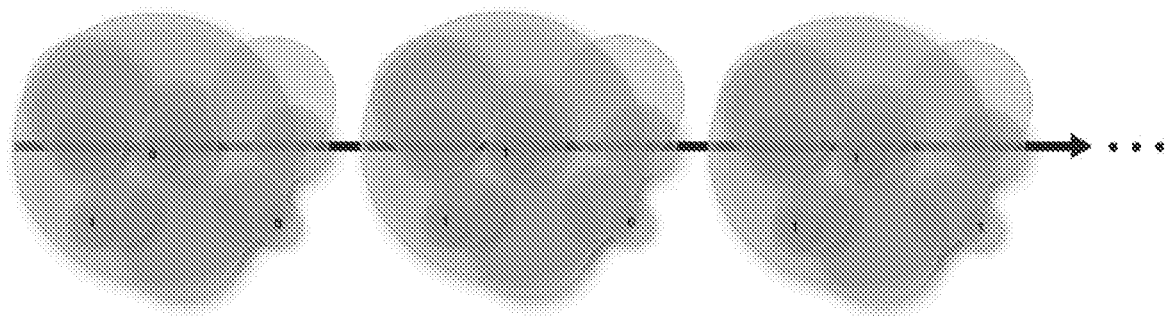

FIG. 34: Comparison between traditional silicon based computers and proposed protocell computing.

Figures 35A, 35B:
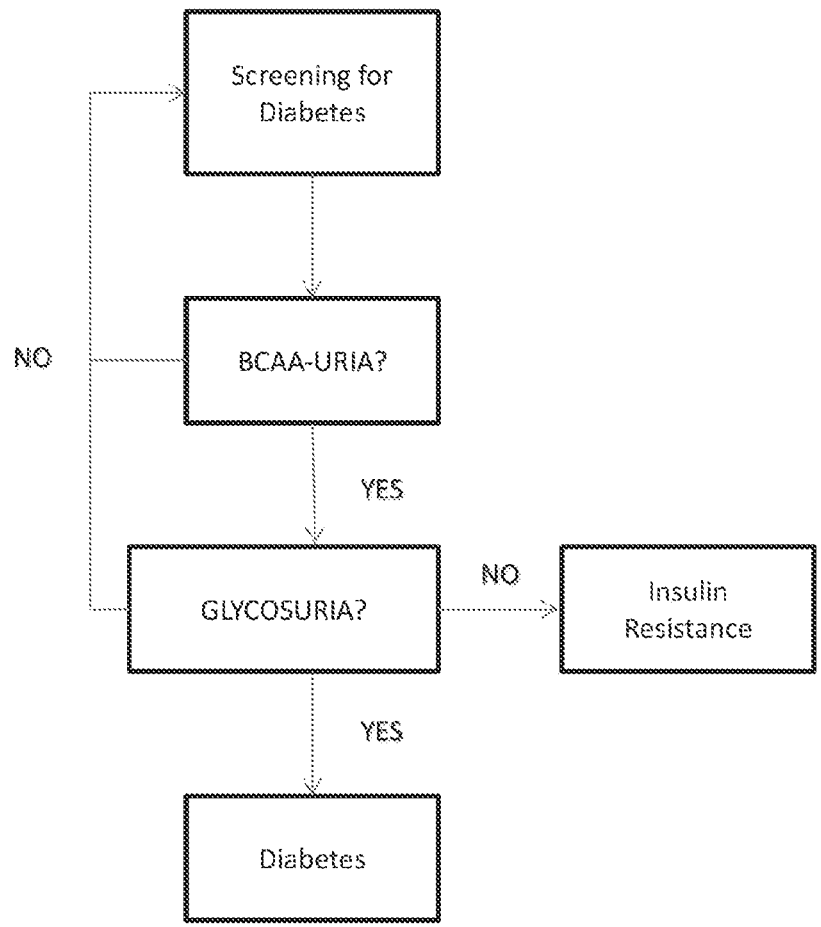
Figure 35C:
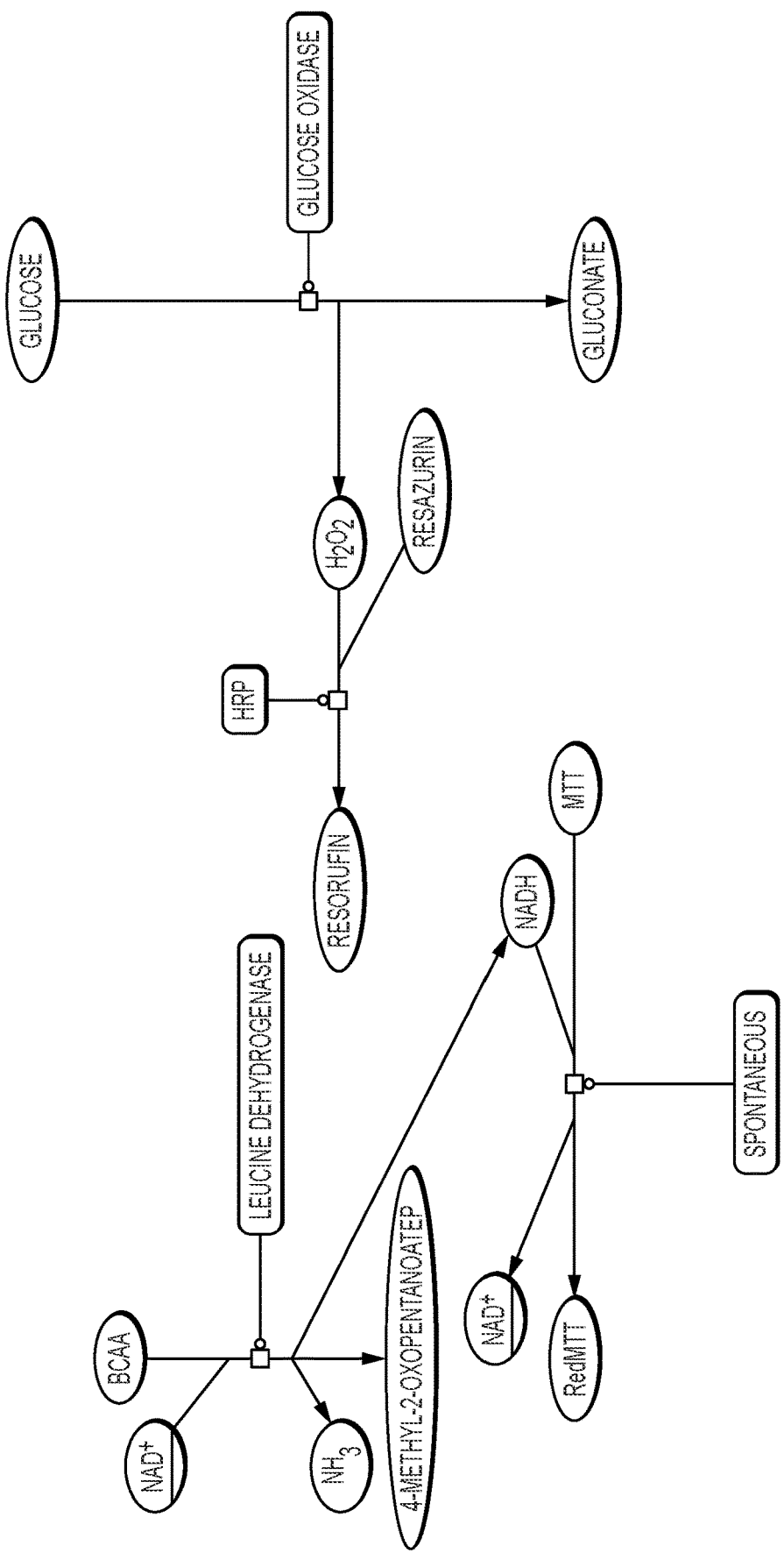

FIG. 35A-35C: In silico design of synthetic biochemical circuits for medical diagnosis. Formal Boolean description depicted using basic logic gates symbols (A). In silico circuits implementation with biochemical parts (C), and theoretical truth tables(B) for the branched-chain amino acids (BCAA) model in early insulin resistance diagnosis.

Figure 36:
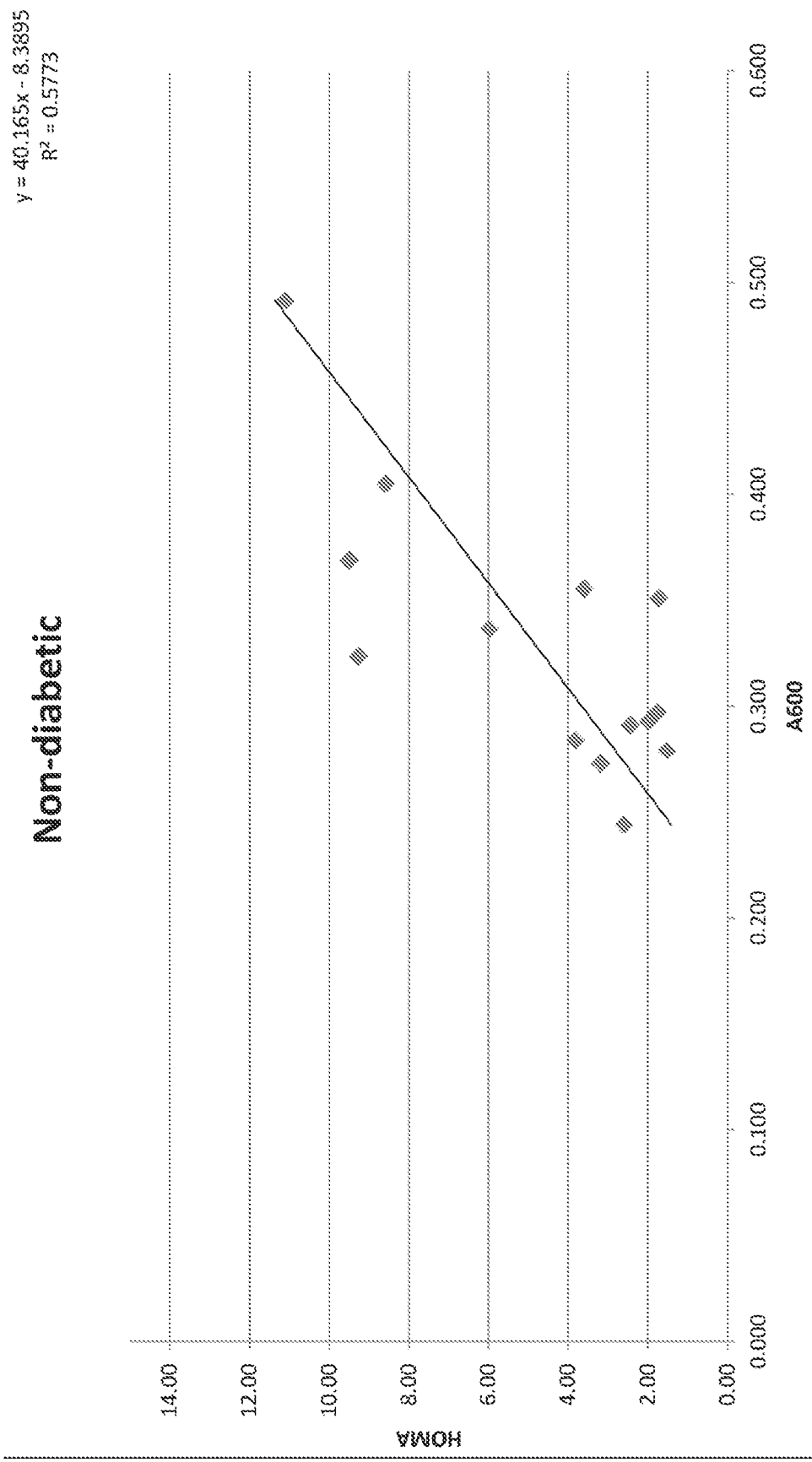

FIG. 36: Figure showing a strong correlation between the measured seric BCAA and the HOMA (Homeostasic model assessment of insulin resistance) parameter measured in a classic test.

Sera from patients from a general population presenting diverse HOMA (Homeostasic model assessment of insulin resistance) and body mass index (BMI) were submitted to the proposed BCAA enzymatic test. The FIG. 36 shows a strong correlation between the measured seric BCAA and the HOMA parameter measured in a classic test.

EXAMPLE 1: MATERIALS AND METHODS

Study Design

To evaluate the robustness of our system and its functionality in clinical samples, we used urine pools from healthy individuals as well as urine samples from healthy individuals and diabetic patients. Regarding collection of clinical samples, non-pathological (control) and glycosuric (diabetic) urine samples were obtained from the Department of Endocrinology of the Lapeyronie Hospital, Montpellier, France. Individual informed consents were obtained from the patients and control individuals. Glycosuric urine samples were collected from 10 newly discovered, non-stabilized diabetic patients. Urine samples were stored at −80° C. before use.

Protocell Microfluidic Construction

PDMS Microfluidic chips were designed and prototyped using AutoCAD software and fabrication was carried out by the Stanford University microfluidic foundry. The microfluidic chip was connected with PTFE tubing to neMESYS V2 syringe pumps (Cetoni GmbH, Germany). Microfluidic processes were imaged using a Leica DMIL microscope mounted with a Canon 750D or a Phantom V7.3 ultrafast camera.

Spectrometric Assays, Flow Cytometry and Microscopy

To test the operability of the different systems, synthetic biochemical networks and protosensors were inoculated in 100 µl total volume of PBS with or without inducer, or urine from patients diluted at a ratio of 1:2 in PBS for a total volume of 100 µl in a 96-well plate. If not differently specified, After 1 hour of incubation, fluorescence and absorbance was read using a synergy H1 plate reader. We concomitantly tested urine clinical samples from non-stabilized diabetic patients using the Siemens Multistix 8 SG reagent strip according to the manufacturer's protocol. Flow cytometry experiments were performed on a Guava EasyCyte bench top flow cytometer (Merck) equipped with a 488 nm laser, and analyzed using FlowJo vX software. Confocal microscopic assays were performed on a Leica SP8-UV equipped with 63× oil lens and 355 nm, 488 nm and 561 nm lasers.

Data Analysis and Statistics

Experimental values are reported as means±SD. All experiments were performed in triplicates. Data, statistics, graphs, and tables were processed and generated using MATLAB (MathWorks) and SigmaPlot (Systat Software Inc.). For receiver operating characteristic analysis, a set of 72 measurements performed in non-pathological urine were compared to 72 measurements performed in urine containing 1% w/v glucose.

In Silico Modeling, Simulation, and Computed Output Signals a) HSIM Modelisation For all simulations, we used a protocell diameter of 10 µm. To generate heat maps, we ran 5 simulations for each input concentration point in order to average for stochasticity. FIG. 4 depicts the enzymatic multisubstrate mechanisms for biochemical reactions, with the associated HSIM model equations we used for simulation.

b) Modeling Protocell Permeability

For the purpose of this study, we implemented in HSIM the diffusion rate dn/dt (in mol/s) of input biomarker metabolites from the medium to the inside of protocells through the membrane. This is driven by passive diffusion, given by a modification of Fick's law, which states that the diffusion rate across the membrane is directly proportional to the permeability coefficient P, to the difference in solution concentrations C1aq-C2aq, and to the area A of the protocell, or $$\frac{dn}{dt} = PA\left(\frac{Cexterior - Cprotocell}{dx}\right)$$

With for any molecule, the value of P, and thus its rate of passive diffusion, is proportional to its partition coefficient K:

$$P = \frac{kD}{x}$$

Where D is the diffusion coefficient of the substance within the membrane and x is the membrane thickness. These experimental parameters can be easily found in the literature for a wide panel of molecules diffusing across phospholipid bilayers. HSIM supports the introduction of permeability coefficient P (m·s−1). For this study, we used a P value for ethanol and acetone diffusing passively across DPPC bilayer of around 0.01 m·s−1. Phospholipid bilayers being naturally impermeable to other organic solutes, we introduced staphyloccus α-hemolysin pore forming protein in the membranes of protocells, in order to allow passive diffusion of input biomarkers metabolites. The diffusion coefficient has been widely measured, and according to a recent measurement by Wanatabe et al. (102) was estimated around 5.1.10-11 m$^2$·s−1, which is interestingly only ~10 time smaller than in free aqueous solution. Considering the DPPC bilayer to be 3.2 nm wide (103), one can calculate the permeability coefficient, which gives us 1.6.10-2 m·s−1. We further hypothesize that only one third of protocells surface would be accessible to hemolysin treatment, which would then correspond to a value of 0.5.10-3 m·s−1.

c) BIOCHAM Modelisation

Validity domains were computed to extract concentration thresholds (N and R) at steady state (T in seconds) satisfying temporal logic specifications. We first performed sensitivity analysis on concentration parameters with a specified logic formula and numerical temporal properties corresponding to requested systems behavior, with 0.5 variations on parameters. This permitted us to identify the two most sensitive initial state concentration parameters of the systems which we then used to visualize the design space through comprehensive map of configurations satisfying specifications. We then conducted an automated concentration parameter search according to the stochastic optimization method CMAES implemented in Biocham (covariance matrix adaptive evolution strategy. For instance, for the model GluONe, this process would require the following commands in Biocham:
% Trace analysis: extraction of output concentration thresholds (N and R) and switch time (T) at steady state (FG):
validity_domain(F(G((Time>T) & (N>[NADH]) & ([resorufin]>R)))).
% SENSITIVITY analysis of concentration parameters c, a, b and f with 0.5 variations:
% Temporal specification with and time horizon of 10 minutes and concentrations N>10000000 & R>1000000
sensitivity([c,a,b,f],[0.5,0.5,0.5,0.5],F(G((N>[NADH]) & ([resorufin]>R))), [N,R], [10000000,1000000], 600).
% VISUALIZATION of satisfaction landscape:
landscape([c,a],[(0,10000000),(0,100000000)],F(G((N>[NADH]) & ([resorufin]>R))), [N,R], [10000000,1000000], 10, 600, landG1DHADH).
% PARAMETER SEARCH:
search_parameters_cmaes([c,a,b,f],[(0,10000000),(0,100000000),(0,1000000 0),(0,2000000000)],F(G((N>[NADH]) & ([resorufin]>R))), [N,R], [10000000,1000000], 600).
All analysis and in silico modeling were performed according to input concentration parameters corresponding to pathological threshold values. The following pathological threshold for input biomarkers were rationally specified according to clinical requirement, and used for calculations and parameter optimization:
Ketones>17 µM (10 mg/dl, pathological if >0)
Glucose>1.39 mM (25 mg/dl, pathological threshold)
Lactate>10 µM (pathological if >0)
EtOH>17.4 mM (80 mg/dl, equivalent to DIU)
NOx>1000 µM d) Translation of Probability from HSIM Stochastic Simulator to Mass Action Rates for Biocham ODE Solver HSIM manages molecules in terms of copy number, and not in concentration terms, as it takes into account compartments volumes. Biocham uses concentrations, where Mass action rate factors intrinsically integrate the volume parameter. For a monomolecular reaction, in Biocham as K is in volume/time and [A] in copy number/volume, K*[A] is the number of reactions that will happen per units of time. Likewise, HSIM integrate a constant time step in its probabilities. Similarly, for a bimolecular reaction, in Biocham K is in volume$^2$/time and [A] and [B] in copy number/volume, which gives us a number of reaction events per units of time. HSIM probabilities have thus to be translated into BIOCHAM mass action rates. Mass action rate (MA) used in the Biocham ODE solver can be related to HSIM stochastic simulator probabilities (P) according to:

$$(MA) = \frac{1}{\tau}\frac{\alpha}{V}(P)$$

For bimolecular reaction of the form $A + B \rightarrow C$ [P] (order 1 reaction)

$$(MA) = \frac{1}{\tau}(P)$$

For monomolecular reaction of the form $A \rightarrow B$ [P] (order 0 reaction)

With τ, V, and α corresponding to HSIM iteration step (100 µs=10−4 sec.), experimental proportionality factor, and protocell volume, respectively.

e) Computed Absorbance and Fluorescence Maps

In order to predict system's fluorescence and absorbance outputs in silico depicted in FIGS. 3B and 6A, we needed to calibrate computed output concentration to experimental values. This could be achieved by generating experimental calibration curves, which could be then analyzed to yield a mathematical relation between concentration and signal (FIGS. 7A-7C)

Complete Characterization and Kinetics Measurements of Synthetic Biochemical Circuits See FIGS. 8-11

Microscopic Size Dispersion Measurements

To assess the size dispersion of protocells, we took random size calibrated microphotograph of protocell preparations using a LEICA DMIL inversed microscope equipped with a 40× lens and a Canon 550D camera mounted on a phototube. Microphotographs were then processed using ImageJ software and a custom script, which allowed for automated size analysis of protocells. Size dispersion figure were plotted and fitted with using the allfitdist.m script in Matlab software.

Microfluidic Chips Used in this Study
See FIGS. 13 and 14

EXAMPLE 2: MICROFLUIDICS FOR SYNTHETIC BIOLOGY: METHODS FOR PROTOCELLS FABRICATION

Microfluidics and Protosensor Preparation and Characterization

PDMS microfluidic chips were designed and prototyped using AutoCAD software and fabrication was carried out by the Stanford University microfluidic foundry. 20 Gauge holes were punched in the PDMS chip, allowing the use of customized made stainless steel adapters (New England Small Tube) for PTFE tubing connections (1/16 OD, 0.8 mm ID). The flow in microfluidic channel was controlled via displacement driven flow using Cetoni neMESYS syringe pumps equipped with high precision glass syringes. We found strong dependence of protosensors yields of production on flow rates, that were kept at 1/0.4/0.4 µl/min (A/B/C) to achieve best encapsulation efficiency. Movies taken with an ultrafast camera (Phantom v7.3) mounted on a LEICA DMIL inverted microscope at ~20 000 FPS allows us to estimate around ~1500 Hz the frequency of protosensor generation at these flow rates.

We introduced in the microfluidic design a device previously described, known as the staggered herringbone mixer (SHM)(66). It enables efficient passive, chaotic mixing between different solutions under Stokes-flow regime. We introduced two times more cycles (i.e. 10), as we calculated that ~5 cycles were sufficient to achieve efficient mixing, according to the equations provided in Williams et al. (66). We integrated this device in the designs to achieve full mixing of the two C channels carrying biochemical species just before encapsulation, in order to ensure homogeneous internal content, precise stoichiometry, and efficient encapsulation, which we reasoned could have been affected by laminar biochemical gradients and spatial anisotropy of concentrations. Synthetic biochemical circuits can then be spontaneously assembled just before encapsulation, by that mean standardizing the encapsulation mechanism and reducing its dependency on the nature of biochemical materials. Moreover, this design allows for fine tuning on stoichiometry via control on the input flow rates, which proved practical to test different parameters for straightforward prototyping of protosensors.

Our strategy relies on a microfluidic flow-focusing droplet generation design that generates water-in-oil-in-water (W-O-W: Biochemical circuit in PBS—Phospholipid in Oleic acid—Storage Buffer A) double emulsions. Double emulsion templates are generated in described flow-focusing channel geometries. DPPC phospholipid membranes then self-assemble during a controlled solvent extraction process (Oleic acid is extracted by methanol present in Storage buffer A). The rational we use for choosing DPPC concentration in oleic acid is adapted from Teh et al. (56). Briefly, oleic acid solution was composed of 1.1 mM DPPC. This concentration was chosen so that there would be a sufficient number of phospholipids to form a lipid bilayer around a 10 μm diameter vesicle. The average area per molecule of DPPC in a bilayer membrane is estimated around a value of 0.64 nm$^2$ (68). Considering that a 10 μm liposome would have a lipid area of 3.14.10-10 m$^2$, at least 8.15.10-16 moles of DPPC would be required to compose the full lipid bilayer of a liposome. Assuming the maximum thickness of oleic acid contained by the primary double emulsion to be 5 μm, we can calculate the volume of oleic acid to be 3.665 pL. A 1.33 mM DPPC concentration would be sufficient, as is it 5 times the amount of phospholipid needed to form a lipid bilayer around the vesicle. In addition, we briefly investigated DOPC, DMPC and DPPC phospholipids for protocell fabrication, and found that DPPC achieved better apparent stability and superior production yields.

In order to achieve selective biomarker input entry and matter/information exchange between protocell content and exterior medium, we capitalized on passive pore forming bacterial protein α-hemolysin. α-hemolysin pores have several properties that identifies it as a robust transmembrane channel suitable for biosensing applications. α-hemolysin pores are self-assembled in the membrane and do not require specific assembly conditions, they are stable over a wide range of pH and temperature and are open in normal conditions. The transmembrane pore of α-hemolysin operates the delivery of ions and small organic compounds such as sugars, metabolites or nucleotides in a selective way through the walls of synthetic lipid vesicles with a passive diffusion rate of $5.5 \pm 1.5 \times 10^{-4}$ s$^{-1}$ as previously measured.

The output channel of the microfluidic chip containing newly formed protosensors was connected with PTFE tubing to a collection vial containing buffer A kept on ice. After 5 hours of fabrication which also allows methanol to evaporate, we obtained ~1 ml of protosensor (by encapsulated volume). The final solution containing protosensors corresponding to a ~1:5 final dilution in buffer A could then be stored at 4° C. for a maximum time of 1 week before further use.

For measurements, Hemolysin treatment of protosensor was performed 15 minutes prior to induction. Hemolysin was added for a final concentration of 1 μM. Protocells solutions were then back diluted at a 1:1 proportion into the sample to test (e.g. Urine). Induction was carried out under slow agitation at 25° C. All fluorescence and absorbance measurements were performed on a synergy H1 plate reader, in 100 μl p96 microwells.

TABLE 1

Stock solutions and concentrations used in this study. All chemicals and enzymes were purchased from Sigma Aldrich.

| Molecule designation | Stock solution | Concentration of use (batch/protocells) | | |
|---|---|---|---|---|
| | | GluONe | LacOH | GluNOx |
| NAD+ | 50 mM PBS | 250 μM/4 mM | 250 μM/5 mM | 100 μM/2 mM |
| NADH | 50 mM PBS | — | — | — |
| Acetone | 100 mM PBS | 1 mM (unless specified) | — | — |
| Ethanol | 100 mM PBS | — | 20 mM (unless specified) | — |
| Glucose | 50 mM PBS | 1 mM (unless specified) | — | 5 mM (unless specified) |
| NO3 | 50 mM PBS | — | — | 5 mM (unless specified) |
| Lactate | 100 mM PBS | — | 0.5 mM (unless specified) | — |
| Isopropyl alcohol | 100 mM PBS | — | — | — |
| G1DH | 3.4 U/μl PBS | 8.5 U/ml = 0.354 μM/7.4 μM | — | 138 U/ml = 5.7546 μM/127 μM |
| ADH | 55.7 U/ml PBS | 0.2785 U/ml = 14.06 μM/221 μM | 0.2785 U/ml = 14.06 μM/317 μM | — |
| AO | 0.1 U/μl PBS | 0.75 U/ml = 0.02725 μM/0.59 μM | — | — |
| NR | 1 U/ml PBS | — | — | 4.2 μM = 0.5 U/ml/92 μM |
| HRP | 10 U/ml PBS | 0.015 U/ml = 0.00104 μM/0.0208 μM | 0.05 U/ml = 0.00347 μM/0.0754 μM | — |
| LO | 6.425 U/μl PBS | — | 0.1 U/ml = 1.12 μM/23.4 μM | — |
| Hemolysin | 250 μM PBS | 1 μM | 1 μM | 1 μM |
| Resazurin | 10 mM water | 50 μM/1 mM | — | — |
| ABTS | 10 mM PBS | — | 100 μM/2 mM | — |
| DAF-2 | 5 mM DMSO | — | — | 10 μM/200 μM |

G1DH: Glucose-1-dehydrogenase,
ADH: Alcohol dehydrogenase,
AO: Alcohol oxidase,
NR: Nitrate/Nitrite reductase,
HRP: Horseradish peroxidase,
LO: Lactate oxidase,
ABTS: 2,2'-azino-bis (3-ethylbenzothiazoline-6-sulphonic acid),
DAF-2: 4,5-Diaminofluorescein.
See Table S2 below for more information about enzymes used in this study.
Stock solutions were kept at −30° C. until use.
Resorufin and ABTS solution were prepared the same day of the assays or kept no longer than a week

TABLE 2

Biochemical parts and associated kinetic parameters used in this study to build biochemical circuits.

| Enzyme/reaction | Organisms | Substrate 1 | Km (mM) | Substrate 2 | Km (mM) | Kcat 1 (/s) | Kcat2 (/s) | Source | Mechanism |
|---|---|---|---|---|---|---|---|---|---|
| Nitrate Reductase (nitrate-> nitrite) EC 1.7.1.1 | *Arabidopsis thaliana* | NADH | 0.004 | NO3— | 0.015 | — | 210 | BRENDA | Random bi-bi |
| Nitrate Reductase (nitrite-> NO) EC 1.7.1.1 | *Arabidopsis thaliana* | NADH | 0.004 | NO2— | 0.0074 | — | 2 | 68, 70 | |
| Glucose 1-Dehydrogenase EC 1.1.1.47 | *Pseudomonas* sp. | NAD+ | 80 | Glucose | 0.86 | 200 | 400 | BRENDA | Ordered bi-bi |
| Alcohol Dehydrogenase EC 1.1.1.1 | *Equus Caballus* | NADH | 0.0025 | Acetone/acetaldehyde | 135/6 | 0.717 | 0.33/31.8 | BRENDA | Ordered bi-bi |
| Alcohol Dehydrogenase EC 1.1.1.1 reverse | *Equus Caballus* | NAD+ | 0.34 | Isopropanol | 268 | 0.41 | 0.75 | | |
| Alcohol Oxydase EC 1.1.3.13 | *Candida* sp. | isopropanol | 10 | — | — | 150 | — | BRENDA | Ping-pong |
| Horseradish peroxidase 1.11.1.7 | *Armoracia rusticana* | Ample × Red | 0.081 | H2O2 | 0.005 | 240 | — | BRENDA | Ping-pong |
| | | ABTS | 0.18 | H2O2 | 0.005 | 760 | — | | |
| | | NADH | 0.012 | H2O2 | 0.005 | 0.009 | — | 71-72 | |
| Lactate Oxidase 1.13.12.4 | *Pediococcus* sp. | (S)-Lactate | 0.2 | — | — | — | 283.3 | 74, BRENDA | Ping-pong |
| Alcohol Dehydrogenase EC 1.1.1.1 | *Equus Caballus* | NAD | 0.0074-0.01 | Ethanol | 2.46 | 308 | — | BRENDA | Ordered bi-bi |
| NO decay | N.A. | NO | — | — | — | 1.9.10-3 | — | 75 | N.A. |
| NO reaction | N.A. | O2 | 0.001 | — | — | 2 | — | 76, 70, 77-80 | N.A. |
| | | NO2 | 0.001 | — | — | 2000 | — | | |
| | | DAF-2 | 0.001 | — | — | 6.28 | — | 69 | |
| N2O3 reaction | N.A. | DAF-2 | 0.001 | — | — | 2000 | — | | |

EXAMPLE 3: COMPUTER ASSISTED DESIGN AND MODELING FOR BOTTOM-UP SYNTHETIC BIOLOGY

Converting design concepts to predicted results is a challenging task when facing the overwhelming complexity of biology. Therefore, the scaling up into increasingly complex biochemical circuits requires automated tools to assist design. It is interesting to point out that electronic design automation for instance, sustained the rapid and geometrical growth in size and capacity of electronic devices (i.e. Moore's law) (30). Following the analogy, the de novo construction of biological circuits and systems according to specifications, could be greatly supported and accelerated by computer assisted modeling, simulation, design, model checking, sensitivity and robustness analysis (31).

During the last decade, systems biology has given major support to explore design principles linking biochemical circuits' topology to biological processes of interest, since it focuses on the development of computer tools for modeling, simulation to understand complex biological systems (30). The main reason that prevented synthetic biologists to identify robust configurations to implement within a configuration/parameter space in a biological system to design, is the number of configurations that grows exponentially with the size of the system that need to be experimentally sampled. In silico simulation and model prediction assist in the design process and decouple the pace at which synthetic biochemical circuits can be constructed to solve specific biosensing and biocomputing tasks.

The engineering of programmable circuits requires manipulable abstract entities. Composability in design is crucial to enable the construction of complex systems from the assembly of standardized biochemical parts. To this end, parts, modules, devices, systems are organized in hierarchies (2), to enable rational concatenation at all levels, as well as the distribution of tasks to carry out in the design process. Computer assisted design tools optimize the efficiency and easiness of iterative steps, especially when supported by graphical user interfaces (FIG. 15A). Crucial to this framework is the identification of standardized basic components that are fully characterized regarding their biophysic, thermodynamic and kinetic parameters. They can further be classified in easy accessible databases to speed up the design process and ease the model calibration. This approach is of major importance in synthetic biology, and proved outstanding capabilities for in vivo synthetic gene networks (see the BioBrick registry of genetic parts (4)). Likewise, the laboratory developed the hierarchical biochemical database CompubioticDB367 that stores robust biochemical parts and devices, which we are constantly refining and augmenting.

The design process properly begins with the formalization of systems specifications in mathematical terms, which is followed by an abstract implementation of the circuit using standardized biochemical parts. This design framework uses mathematical description, or models taking into account knowledge on biochemical parameters (either measured or assumed), that can be then used to compute and analyze qualitatively in silico the trajectory and behavior at the system-level. The process of making biochemical assumptions that will best account for reality (i.e. model fitting) is crucial since it will impact the reliability and precision of the predictions, while overly complex assumption will be deleterious to computation and optimization speed and efficiency. This step happens before in vitro implementation and enables to map the design space, and explore design alternatives.

Design of a synthetic circuit then undergoes quantitative assessment of parameter and compositional space (i.e. initial concentrations, rate constants of enzymes . . . ) to verify performance specifications. Lack of exhaustive characterizations in context for some biological parts often imposes successive phases of refinement and experimental agreement (goodness of fit with data) and theoretical iterations (FIG. 15B). Correct parameters of the model are a crucial to obtain a predictive solution, but iterative optimization can facilitate this process.

A comprehensive mapping of the input-output transfer functions and its sensitivity to the circuits composition is of utmost importance to reduce modes of failure, and for the programming of biochemical circuits ensuring robustness (i.e. defined as the capacity for sustained and precise function even in the presence of structural or environmental disruption (32). Model analysis often comprises sensitivity and robustness analysis. Sensitivity analysis is used to identify parameters source influencing the performance of the model when perturbed. It enables the estimation of the variation of performance under an admissible parameter variation. This analysis is very informative, particularly in cases where circuit model parameters are uncertain or assumptions are made with large variability. The capacity of different designs to undergo and sustain structural or dynamic perturbations without affecting their transfer function can be assessed through robustness analysis. This analysis can provide precious information for the design process.

The design process requires modeling formalisms, which can be defined as the language in which the model is described. It recapitulates the circuit topology and underlaid mechanistic within a graphical description. The formalism's mechanistic comprises the simulation method, which can be Boolean, deterministic, stochastic, agent-based or hybrid methods. This choice will condition the descriptive and predictive power of a specific formalism. Then, a modeling environment implements in silico a chosen formalism to simulate a biochemical system. Numerous software packages have been developed for systems and synthetic biology for this purpose, for instance COPASI (34), CellDesigner (35), or SynbioSS (36), as well as standardized exchange formats for models, such as SBML (37) (Systems Biology Markup Language).

The different steps of the process can be supported by various computational methodologies and type of modeling frameworks, such as most common deterministic and stochastic modeling. Deterministic model can describe biochemical systems using analytical equations (usually ordinary differential equations, ODEs or partial differential equations, PDEs) comprising numerical parameters describing molecular interaction, which values are certain. Therefore, the output is by definition exactly reproducible for a defined set of parameter values and initial conditions. Assuming spatial homogeneity, systems can be accurately predicted using ODEs. ODEs describe biochemical reaction, or mass balances (concentration) of species according to:

$$\frac{dX}{dt} = F(N, t; \theta)$$

where dX/dt is the rate of change of concentration of species X, X and N are vectors of species concentrations, $\theta$ is a vector of parameters, and $F(N, t; \theta)$ is a vector function that relates rates of change to concentrations (38). Solving a set of equation describing the systems through dynamic simulation will provide with the time-dependent trajectories of the species concentrations in the model (FIG. 16).

Stochastic models use equations and parameters describing random molecular interactions between species and as such can account for fluctuations inherent to biological systems. This can prove valuable if one is interested by the exploration of noise propagation and influence on systems dynamics. A probabilistic equation is used to describe the probabilistic rate laws, such as the Chemical master equation or Stochastic simulation algorithm (SSA) with the famous Gillepsie algorithm (39) of each reaction between a population of interacting species. The assumption is that the biochemical system within a given time frame obeys rules of randomly interacting molecules under Poisson processes with the rate parameter $\lambda$ proportional to the reaction rate. Thus, compared with deterministic models, SSA simulations manipulate discrete quantities.

Both approaches may present advantages and inconvenient. However, fundamentally different conclusions about the long-term fate of systems can be reached depending on stochastic or deterministic models, as well as modeling continuous or discrete space (40). ODEs offer an easiness of implementation, optimization and simulation, and are a good choice to perform extensive mathematical analysis on models, while stochastic methods usually require massive computation power. It should be noted however that stochastic models support closer to reality simulation since they take into account discrete molecular entities, compared to ODEs which process continuous values. Moreover, ODEs can show limits in the ability to capture certain dynamics or even violate physical laws such as diffusion. This difference can lead to drastically different results at low concentration of species. Specialized for different agendas, these two approaches are complementary to study a biochemical circuit. However, they often require distinct input formats, which require conversion of the original models for compatibility.

In Example 4 below, we present and discuss the two software that we collaboratively developed, refined and used for the purpose of this study: HSIM (368, 599, 600) (Hyperstructure Simulator, developed by P. Amar) along with its recently developed graphical interface NetDraw, and BIOCHAM (43, 44) (Biochemical Abstract Machine, developed by F. Fages et al.).

EXAMPLE 4: HSIM AND BIOCHAM SOFTWARE

A) HSIM

HSIM was initially developed to simulate the aggregation and dissociation of large molecular assemblies called Hyperstructures. HSIM is a versatile platform that we used in this study for qualitative and quantitative simulation of biochemical circuits encapsulated in protocells. It exploits two efficient simulation approaches: Stochastic simulation of chemical reactions and entity-centered (i.e. multi-agents) simulation. The stochastic simulation algorithm (SSA) is used with the assumption of spatially homogeneous solutions of reactants, while the entity-centered algorithm enables to take into account spatial heterogeneity in the model when the previous approximation is wrong. Regarding the computational resources, the SSA method shows a limit in the number of reactions it can simulate, whereas entity-centered simulations are limited by the amount of species it can manipulate.

In entity centered simulations, each molecule is considered independently in their environment; where they are allowed to diffuse according to random walk defined by Brownian motion. The spatiotemporal trajectory of the system of interacting entities is then computed according to specific rules (i.e. parameters) and interactions within the volume (i.e. compartments) and other entities (i.e. biochemical reactions: formation or the dissociation of a complex, disappearance, or a change of type of molecules).

The simulator is a stochastic automaton driven by reaction rules between molecules (FIG. 17). HSIM manipulates biochemical reactions of two categories: unimolecular and bimolecular, while rare natural reactions of more than two reactants are reduced to a combination of bimolecular reactions. Unimolecular reactions describe molecules which can transition between a numbers of finite states with an associated probability. In the case of bimolecular reactions, two reactive molecules collide according to the mass action law, and a probability resenting the reaction kinetics is applied to yield products.

HSIM can manage compartments and subcompartments of continuous space and is optimized to manage sizes ranging from small liposomes to eukaryotic cells (100 nm-100 µm). It allows for specification of compartment size, geometry, as well as permeability parameters characterizing the diffusion of species across a membrane of interest.

HSIM keeps a real and discrete computer time record of molecules regarding their types, position, size and interactions. At each time step probability rules are applied to every molecule. The time step used (100 µs) was optimized for a distance of 10 nm according to the average Brownian displacement of molecules observed for real cytosolic crowding.

Apart from macromolecules, most metabolite molecules can be easily processed in a global way using the SSA algorithm (Gillespie stochastic method), since one can consider that the size will not impact Brownian diffusivity. The high copy number approximation for metabolites enables to treat them as statistically homogeneously distributed in the volume. HSIM can manage both entities and metabolites at the same time, by computing the average number of collisions and subsequent reactions at each time steps.

Below is an example of a HSIM input describing a model with a compartment and subcompartement and two types of molecules (metabolite and entity):

```
title = "Compartment test";
geometry = 100:40;
metabolite s, p; // s et p are small molecules
molecule s, p; // s et p are small molecules
display (s, p);
diffusion (s) = 5e-4; // Permeability coefficient through the compartment
```

```
membrane of 5.10-4 cm/s
diffusion (p) = 2e-4; // Permeability coefficient through the compartment
membrane of 2.10-4 cm/s
compartment {
 geometry = 60:30+10+0+0; // length:diameter+x+y+z
 compartment {
  geometry = 40:20+0+0+0; // length:diameter+x+y+z
 }
}
init (1 µM, s); // Initial concentration of molecules
init (500000, p); // Number of molecules
metabolite s; // SSA
E + s -> ES [0.2]; // Km = 1 mM
ES -> E + s [0.05]; // p2/p1 = 0.25*Km.
ES -> E + p [0.0325]; // k3 = 325 /s
molecule p; // entity
E + s -> ES * s [0.2]; // Km = 1 mM
ES * s -> E + s [0.5]; // p2/p1 = 2.5*Km.
ES * s -> E * p [0.325]; // k3 = 325 /s.
```

B) BIOCHAM

BIOCHAM is a software environment developed for the modeling of synthetic biochemical systems. It comprises a rule-based language and a temporal logic based language and supports the simulation and analysis of boolean, kinetic and stochastic models and the formalization of qualitative and quantitative experimental knowledge of biological properties in temporal logic (i.e. Computation Tree logic (CTL), or Linear Time Logic (LTL)). It manages systems of biochemical reactions with molecular concentrations and kinetic descriptions, in the form of the SBML standard.

BIOCHAM automates the exploration of a parameter space to optimize and infers unknown model parameters for specific behavior formalized in temporal logic to systematically verify, analyze and optimize models using model-checking methodologies.

It can perform robustness and global sensitivity analysis according to an evaluation function using violation degree of temporal logic formulae. The violation degree represents the distance between the behavior of the perturbed system and a specified behavior formalized by a temporal logic formula. BIOCHAM automatically computes by numerical simulation of deterministic or stochastic models an estimation of the robustness for dynamical properties and a large number of types of perturbations obtained. It introduced the notion of satisfaction degree of temporal logic formulae to measure the performance of a biochemical system. As a globally relevant measure of system performance, it permitted to broaden the scope of these methods, whereas previous models for synthetic and systems biology were focused on specific behaviors.

EXAMPLE 5: OPERATIONAL PRINCIPLES, DESIGN AND ARCHITECTURE OF PROTOSENSORS

A) Architecture and General Functioning

The protocells we describe in this work consist in vesicular synthetic biological systems which composition is programmed to achieve medical biosensing and biocomputing tasks when driven toward thermodynamic equilibrium. Similarly to cells, in our architectures the biochemical work necessary to support functioning (i.e. signal sensing, processing and output generation) originates from redox reactions. This useful potential biochemical energy is either brought during fabrication and stored as encapsulated electrons donors (such as NADH for example) or is extracted from energy rich molecular inputs (e.g. glucose).

Protosensor architecture thus consists of biochemical synthetic circuits encapsulated within a phospholipid bilayer, which enables to digitize space through the definition of an insulated interior containing the synthetic circuit, and an exterior consisting of the medium to test (e.g. a human clinical sample).

In this study, protocells designate specific types of vesicular compartment of biological size (also known as Giant Unilamellar Vesicles, GUVs ~10 µm), encapsulating a complex aqueous medium comprising the synthetic circuit. Although many types of protocells have been described regarding the nature of their membranes, they are generally composed of highly ordered amphiphilic molecules. These amphiphiles, for instance phospholipids or synthetic copolymers, comprise hydrophilic headgroups and hydrophobic chains, which can assemble into a bilayer. Orientation of hydrophilic heads in contact with the aqueous medium and hydrophobic chains with the interior in each layer is thermodynamically favored. The physicochemical properties of protocell membranes bilayers strongly depend on the nature of the amphiphiles, which will impact permeability, thickness, stability, or elasticity.

Not all amphiphiles can sustain assembly into vesicles, and chemical structure has an important impact on membrane thermodynamics. The dimensionless packing parameter P represents the molecular shape of amphiphiles in solution, and rules the morphology of the corresponding assembly. It can be expressed as:

$$P = \frac{v}{al}$$

where v is the volume of the hydrophobic moiety, a the hydrophilic-hydrophobic interfacial area, and l the hydrophobic moiety length, as illustrated. In order to form stable bilayer and protocell vesicular assemblies, P has to be ~1. In our study, we thus investigated the use of common phospholipids with appropriate packing parameter that have been widely used for protocells fabrication, namely Dimyristoylphosphatidylcholine (DMPC), Dioleoylphosphatidylcholine (DOPC), and Dipalmitoylphosphatidylcholine (DPPC).

Importantly, in order to perform biosensing, protosensors require an exchange of matter and information between their interior and with the medium they evolve in. To this end, after encapsulation of synthetic circuits we perform a subsequent membrane modification step. We see an approach in which the phospholipid membrane is rendered selectively permeable to small organic molecules that serve as inputs for our systems, through the self-incorporation of α-Hemolysin transmembrane protein pores, which has a mass cutoff of 3 kDa (28) (See Materials and Methods).

B) Programming In Vitro Algorithms for the Differential Diagnosis of Acute Diabetes Complications Our goal was to engineer medical protosensors capable of implementing in vitro diagnostic processes (i.e. diagnosing specific pathologies through the biodetection of patterns of biomarkers) formalized as Boolean functions, using synthetic biochemical circuits as a substrate (FIG. 20A). For this purpose, we chose to evaluate the feasibility of integrating a clinically useful medical algorithm enabling to classify acute metabolic complications of diabetes, namely diabetic ketoacidosis, hyperglycemia hyperosmolar state, hypoglycemia and lactic acidosis (FIG. 19). These disorders constitute medical emergencies, and are known to be associated with high medical and socio-economic burden and with an important mortality and morbidity. In addition, we also intended to implement a screening solution for the early onset of diabetes. Hence, not only this study addresses novel engineering concepts, it also tackles concrete clinical problems that are seeking solutions.

These diagnostic processes are possible via the monitoring the presence of 5 different urinary biomarkers and the assessment of their specific concentrations and combinations in urine, namely: glucose, ketones, lactate, ethanol and nitric oxides (FIG. 19). Therefore, we focused on implementing synthetic circuits capable of processing these specific inputs using simple Boolean operations. With this concrete proof of concept in mind, we also emphasized on developing a universal framework permitting systematic and versatile programming of protosensors for other agendas and pathologies. In fact, a large number of different protosensors could be programmed to answer multiple but specific clinical questions, in order to multiplex disease diagnosis in situ (FIG. 20B).

EXAMPLE 6: MOLECULAR PROGRAMMING OF PROTOCELLS: IN SILICO DESIGN TO EXPERIMENTAL VALIDATION OF SYNTHETIC BIOCHEMICAL CIRCUITS

A) in Silico Design, Simulation and Model Checking

The capacity to rationally design biological systems to achieve programmed biosensing and user-defined decision making algorithm and bioactuation requires precise tools within the scope of a systematic approach. Therefore, we first developed an in silico framework supporting the design of synthetic biochemical circuits from the bottom-up assembly of biological parts (FIG. 20A-20B). This computer assisted framework involves the following steps:

Design of abstract programs with respect to Boolean logic and molecular input/output specifications according to (medical) algorithm of interest. At this step, one can formalize the temporal logic properties of a synthetic biochemical system regarding expected reference behavior, expressed by a qualitative and/or quantitative temporal logic formula (13). This comprises the specification of parameters relative to the initial state (i.e. pathological biomarker concentration thresholds for instance).

Implementation of previously defined algorithms using molecular biochemical circuitry: identification of suitable enzymes and metabolites within a network topology obtained from databases and literature to implement molecular Boolean logic operations. Composable and kinetically favorable components are chosen at this step to minimize modes of failure. This process can be automated using recently developed computer assisted extraction of biochemical parts, and Boolean logic gates from metabolic networks of living organisms (45). Experimental characterization of biochemical modules can help this process. Netdraw software if used for user friendly design and mapping of interaction network and to assign reaction rules (with or without kinetic expressions), concentration parameters, as well as spatial parameters such as volume, location of species, and permeability coefficients of compartments. Netdraw is then used for automated generation of HSIM and BIOCHAM code for the model (specification of the initial state, definitions of numerical parameters, compartments volume, invariants, events, declarations of molecular species and locations, specification of the system's behavior).

Stochastic simulation (SSA) is first performed within the HSIM software to verify kinetically and functionally favorable circuits, predict the overall behavior, estimate the functioning and manually explore the design space to identify suitable parameter configurations to be refined.

BIOCHAM simulations (ODE solver) are then carried out to compute validity domains of specified behavior for the system, perform sensitivity analysis to identify sensitive parameters that can then be iteratively optimized, and measure robustness relative to the variation of specific parameters. Models are thus evaluated with respect to temporal logic specifications. Computing a landscape of satisfaction relative to sensitive parameters enables to visualize and identify suitable parameter space satisfying specified behavior, which can be used to select robust parameters for experimental in vitro implementation (i.e. concentration of species for instance, kinetic parameters, initial value or control parameters). One can automate the search, using CMAES methodology (Covariance Matrix Adaptation Evolution Strategy) (46) integrated in Biocham for those parameter values that satisfy a given set of quantitative temporal properties.

Once the parameters satisfying user-defined system specifications have been found, HSIM stochastic simulator can be used to validate and finely map the complete transfer functions of the protosensors. The systems can then be experimentally implemented and its functioning assessed in vitro. Iterations in the design process can occur at each step.

The medical algorithm depicted in FIG. 19, was divided and distributed into three simple biochemical systems (whose truth tables are depicted in FIG. 21A) taking two biomarkers as inputs, which we named GluONe (Glucose and Acetone as inputs), LacOH (Lactate and Ethanol as inputs) and GluNOx (Glucose and Nitric oxides as inputs). The biochemical implementation (i.e. comprising network topology) was assisted in silico using the custom computer tools developed for this purpose, which support the systematic mining of natural biochemical network to retrieve enzymatic Boolean logic gates and circuits satisfying user-defined specifications (FIGS. 5A-5B). We identified three distinct and insulated minimal systems that could operate in parallel, which required 6, 5 and 4 different biochemical entities, comprising 4, 3 and 2 different enzymes respectively. Biochemical knowledge on the parts that enabled formal design was extracted from BRENDA database (See Table 1, FIGS. 3A-3B and FIGS. 6A-6C for more detail). Molecular signal processing occurring in these circuits leads to the biochemical synthesis of the following measurable output signals molecules: NADH (Output 1, 340 nm absorbance), Resorufin (Output 2, 571-600 nm fluorescence), ABTS (Output 3, 420 nm absorbance), and DAF (Output 4, 488-515 nm fluorescence). The Boolean formalism and truth tables corresponding to the medical algorithm, as well as the biochemical implementation are depicted in FIG. 21A (Detailed in FIGS. 6A-6C).

We first performed stochastic simulation in HSIM to evaluate the putative behavior of the three circuits (FIG. 21B). To this end, we used non-optimized models of non-encapsulated synthetic circuits, where initial conditions (i.e. species concentrations) were here determined empirically.

We predicted systems state after induction with various concentrations of biomarker inputs, and represented the computed molecular output signals as heat maps. The relation between in silico calculated molecular concentrations and experimental measured signal was calibrated beforehand (See methods for detail). This permitted us to validate the Boolean logic operations, with very satisfying theoretical signal fold change, as well as near digital response. In addition, we found that switching thresholds for these models were in good agreement with useful clinical sensitivity for biomarker inputs (pathological thresholds: Ketones>17 µM (~10 mg/dl); Glucose>1.39 mM (~25 mg/dl); Lactate>10 µM; EtOH>17.4 mM (~80 mg/dl)); NOx>1000 µM).

B) Experimental Validation In Vitro

We then investigated the experimental behavior of the rationally designed synthetic circuits prior to encapsulation inside protocells. We proceeded to in vitro implementation in the test tube of previously simulated models with the same initial conditions (i.e. concentration of circuits components) using recombinant enzymes and synthetic metabolites at room temperature. We performed multiple experiments consisting in varying initial conditions (presence/absence of components of the circuit and presence of pathological concentrations of input biomarkers), and measured the generation of output signals (fluorescence or absorbance). This allowed us to get a fine understanding of the functioning and detailed experimental characterization of logic operations (FIGS. 19C, 9 and 10). Interestingly, we found that kinetic and end point measurement showed very good agreement with HSIM predictions. In addition, the circuits behaved in exact accordance to Boolean logic specifications with temporal requirements of less than 60 minutes. Outputs 2, 3 and 4 delivered a human readable output signal as expected. Considering signal-to-noise ratio (SNR) as a quantitative measure of biocomputing efficacy (47), we found that these synthetic biochemical circuits showed very good performance in processing molecular signals according to specified Boolean Logic, with calculated SNRs for outputs 1,2,3 and 4 of ~20, 34, 14, 26 dB respectively.

While in this study we were interested in exploring in silico the transfer function of the LacOH system for output 1, we did not yet proceed to experimental validation. Indeed output 1 and 3 are in this set up overlapping in absorbance, which could be easily substracted to obtain a dual readout. However this was not the immediate purpose of this work since it did not present direct clinical utility. Likewise, in the following experimental work we measured outputs 3 and 4 for LacOH and GluNOx systems. These systems will be the subject of further in vitro characterization.

EXAMPLE 7: MICROFLUIDICS APPROACH FOR PROTOSENSORS PROTOTYPING AND FABRICATION: ENCAPSULATING SYNTHETIC CIRCUITS IN PROTOCELLS

A) Theoretical Considerations

Developing protocells as robust biosensors for biomedical analysis requires finest control on physicochemical properties. Thus, production methods ensuring fine tuning on parameters was required, to achieve stable protocells with well-defined size, lipid composition, and enzyme content, catalytic performance and stability of encapsulated biochemical species.

Protocell membrane systems exist in states that are kinetically favorable, or trapped within local energy minimums, instead of rather real thermodynamic equilibrium (48). This implies that the efficiency of fabrication will strongly depend on the choice amphiphile biochemistry as well as on the physical assembly process. This also means that obtaining important yields and reliable encapsulation process are not an easy technological journey.

Since the first published method of cell sized vesicle formation in 1969 through gentle hydration and electro-swelling (49), most developed methodologies can be separated into two common fabrication techniques: hydration and electroformation. The most described and commonly used techniques involved hydration of a dried phospholipid film on a glass surface. For the purpose of this study, we first explored these basic techniques. This process showed extremely sensitive to perturbation, demonstrated poor yields, no control on polydispersity and size of vesicles, low reproducibility and most importantly was incapable of accommodating precise stoichiometry in encapsulation of various biochemical entities.

A more recent and clever method was then described, now known as the water-in-oil emulsion transfer method. It was first developed by Pautot et al. (50) and proved of utmost interest in protocell research (14). Briefly, this technique relies on the generation in a first step of water-in-oil droplets, which allows phospholipids to organize at the phase interface. Then in a second step, these droplets are transferred through another phase interface, thereby producing a bilayer. Although proving as an interesting, precise and versatile technique, it remained incapable of satisfying monodispersity and high throughput requirements.

After its first apparitions, microfluidics shortly generated avenues to engineer amphiphile vesicles tailored with high degree of precision (51). Traditional approaches for fabricating vesicles rely on the slow and low efficiency of self-assembly of amphiphiles. Microfluidic devices however allow precise control on directed membrane assemblies, and generated a vast scientific literature. Methodologies such as hydrodynamic flow focusing (52), pulsed jetting (53) or emulsion-templating (54-56) emerged and brought new opportunities to engineer vesicular structures and tailor them for specific applications. Hence, in these Examples we explored the encapsulation of synthetic biochemical circuits through two microfluidic approaches: directed and undirected self assembly (FIG. 22).

The approach we used for undirected self-assembly relied on microfluidic continuous-flow mixers, also known as flow focusing devices, where a solvent containing an amphiphile of interest is injected into a center inlet of a microchannel cross junction and pinched into a smaller flow by solvent streams on side channels (FIG. 22, right). Mixing driven by molecular diffusion appears at the interface between the two hydrodynamically focused flows (57) in a flow rate dependent way. Flow rates control the width of focused flow, and thus mixing with time and space resolution, enabling complex yet precise mixing processes that could not be achieved in a macroscale context. These performances motivated the use of these devices to control the assembly of phospholipids into structured bilayers, such as the engineering of liposome and polymersome with monodisperse sizes. Amphiphile vesicles are allowed to form at the interface of flow-focused fluids by a complex mechanism relying on sustained bilayer growth by for instance phospholipid membrane self-assembly at the interface. As phospholipid concentration at the interface dependents on flow rates, one can tune vesicle size by simply controlling the flow rate (57-59, 52). Although very appealing, when put into application this approach suffered from unreliable encapsulation efficiency, which could show thermodynamically favored encapsulation of small molecules compared to large proteins, a phenomenon which would dramatically affect the programmability of protocell assemblies. Moreover, the largest liposome sizes achievable with this technique were shown to be ~150 nm, which would limit the complexity of the encapsulated material.

In this context, we decided to pursue another microfluidic approach, which this time relied on directed self-assembly and encapsulation. Using microfluidic technologies, it is easy to generate monodisperse single water-in-oil emulsions, which constitutes a whole field commonly known as Droplet Microfluidics. Interestingly, this approach can be extended to double water-oil-water emulsions, and further exploited to generate emulsion-templated vesicles, facilitated by the routine capabilities to generate uniform size calibrated emulsions with near total encapsulation efficiency. Double emulsion templates can be generated to mimic a vesicular membrane, which is in this case composed of an oil phase. One can then tune the emulsion generation to obtain double emulsions with thin oil phases. If an amphiphile is dissolved in the oil phase, these architectures can thus be converted into real amphiphile bilayers vesicles via oil removal (60, 61) (FIGS. 23A-23C).

The main microfluidic designs we explored in this Example exploit droplet generation mechanisms. Similarly to the first designs, they can also be described as flow focusing devices, but this time are used to introduce shearing at the interface of different phases in order to generate droplets. The presence of two phases (i.e. Oil-Water) introduces extra complexity in the system, where inertial, viscous and interfacial forces arising from different fluids will compete (62). However, as previously discussed, microfluidic domain deals with Stoke flows, where the laminar characteristics associated with dominating surface tension creates uniform interfaces.

We adapted the one step double emulsion generation which had been demonstrated a decade ago by Utada et al. (63). Since then, many designs successfully intended to adapt this strategy within microfluidic channel geometries. The underlying mechanism exploits a droplet forming regime of an aqueous droplet into an oil phase, itself dripping in another aqueous phase. This happens when both dispersed phases are in a dripping regime and shear produces break at the same time. The behavior of different phases regarding the wettability to the channel surface is of utmost importance for droplet generation. In fact, the phase to be dispersed into the other one should be non-wetting to the channels, to ensure total efficiency (i.e. reduce phase inversion). Importantly, wetting characteristic in PDMS devices can be increased using a chemical treatment, for example in our case, a polyvinyl alcohol treatment ensures perfect water wettability and forbids oil wettability (64). The oil and water phases having different velocities, a viscous shear is induced at their interface. This phenomenon is stabilized by capillary stress coming from interfacial forces, which tends to minimize the area of the interface, thereby producing droplets. As discussed, this mechanism can be represented by the Capillary number. While interfacial forces are ruled by area, viscous forces are volume based. This is of importance since at low capillary numbers (i.e. microchannel assumption), viscous forces and thus flow rates will be the main influences driving droplet breakage. As the capillary number depends on surface tension, one can facilitate droplet breakage and stabilize droplet spherical shape through the addition of a surfactant (i.e. decreasing surface tension and capillary number). In our designs, we used high flow rates in order to stay within a jet-like configuration ensuring highest fabrication throughput.

Our strategy thus relied on a microfluidic flow-focusing droplet generation design that generates water-in-oil-in-water (W-O-W: Biochemical circuit in Phosphate buffer—Phospholipid in Oleic acid—Buffer) double emulsions. Double emulsion templates are generated in described flow-focusing channel geometries (FIG. 25A). DPPC phospholipid membranes then self-assemble during a controlled solvent extraction process where Oleic acid is extracted by methanol present in buffer (FIGS. 23B and 23C). The rational we use for choosing DPPC concentration in oleic acid consists in calculating the concentration so that there would be a sufficient number of phospholipids to form a lipid bilayer around a 10 µm diameter vesicle (Detailed calculation can be found in Materials and Methods). Oleic acid and methanol present the advantage of being biocompatible and non-toxic to enzymes compared to other inorganic solvents, and was chosen to minimalize deleterious chemical interactions.

In addition, we investigated DOPC, DMPC phospholipids for protocell fabrication, and found that DPPC achieved better apparent stability and superior production yields. We found that DPPC vesicles were the most robust phospholipids for protocell construction, since they were capable of withstanding osmotic stress and showed prolonged stability and robust encapsulation at room temperature (FIG. 25C). This can be explained by the fact that an increase in acyl chain length (and therefore lipid transition temperature) as well as the complete saturation of the acyl chain, is directly proportional to stability. Moreover, DPPC offers greater orthogonality and versatility, since they are less permeable, less susceptible to oxidation and disruption by natural proteins (e.g. serum proteins) (65).

B) Experimental Set-Up and Results

The working microfluidic set-up is depicted in FIG. 24 (extra experimental details can be found in Materials and Methods). Briefly, the flow in microfluidic channels was controlled via displacement driven flow using nanometric syringe pumps equipped with high precision glass syringes, and controlled in real time with a computer interface. We found strong dependence of protosensors yields of production on flow rates, that were kept at 1/0.4/0.4 µl/min (Storage buffer/Oil+Phospholipids/Biochemical circuit, respectively) to achieve best encapsulation efficiency. Real time visual monitoring of the fabrication process enabled precise control on the fabrication process. In addition, measurements from the ultrafast camera at 20 000 FPS allows us to estimate around ~1500 Hz the frequency of protosensor generation at these flow rates (FIG. 2).

The microfluidic flow-focusing droplet generation design is depicted in FIG. 25A. We introduced in our microfluidic design a device previously described, known as the staggered herringbone mixer (SHM) (66). It enables efficient passive, chaotic mixing between different solutions under Stokes-flow regime. We integrated this device in our designs to achieve full mixing just before encapsulation of the multiple upstream channels carrying biochemical parts, in order to ensure homogeneous internal content, precise stoichiometry, and efficient encapsulation, which we reasoned could have been affected by laminar biochemical gradients and spatial anisotropy of concentrations. Synthetic biochemical circuits can then be spontaneously assembled just before encapsulation, by that mean standardizing the encapsulation mechanism and reducing its dependency on the nature of biochemical materials. Moreover, this design allows for fine tuning on stoichiometry via control on the input flow rates, which proved practical to test different parameters for straightforward prototyping of protosensors.

We analyzed size dispersion of protocells in order to characterize the fabrication process using light transmission microscopy (FIG. 25B). At these flow rates we obtained fairly monodispersed protocell with average size of ~10 µm, and an apparent inverse Gaussian distribution of the size parameter. Interestingly, circuit encapsulation showed no influence on size distribution of protocells, which demonstrate that the encapsulation process can be decoupled from the complexity of the biochemical content. Moreover, no evolution of the size parameter was recorded for 3 months, which demonstrated the absence of fusion events between protocells and a very satisfying stability in the conditions of our storage method (i.e. 4° C. in storage buffer). We then assayed encapsulation stability using confocal microscopy. To this end, we encapsulated an irrelevant protein bearing a fluorescent label within protocells, and measured the evolution of internal fluorescence over the course of three months. We found that internal fluorescence remained stable, which demonstrates no measurable protein leakage through the protocell membrane after three months in our storage conditions.

Figure 27A:
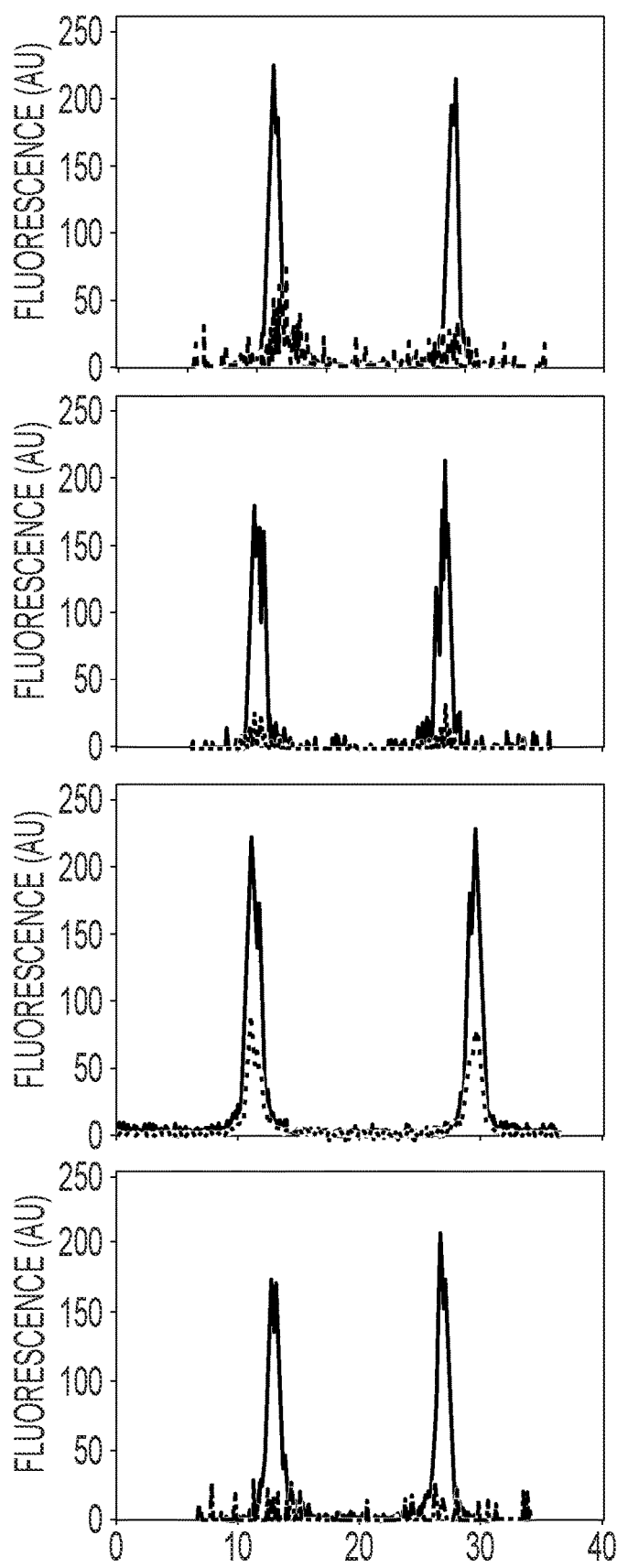
Figure 27A:
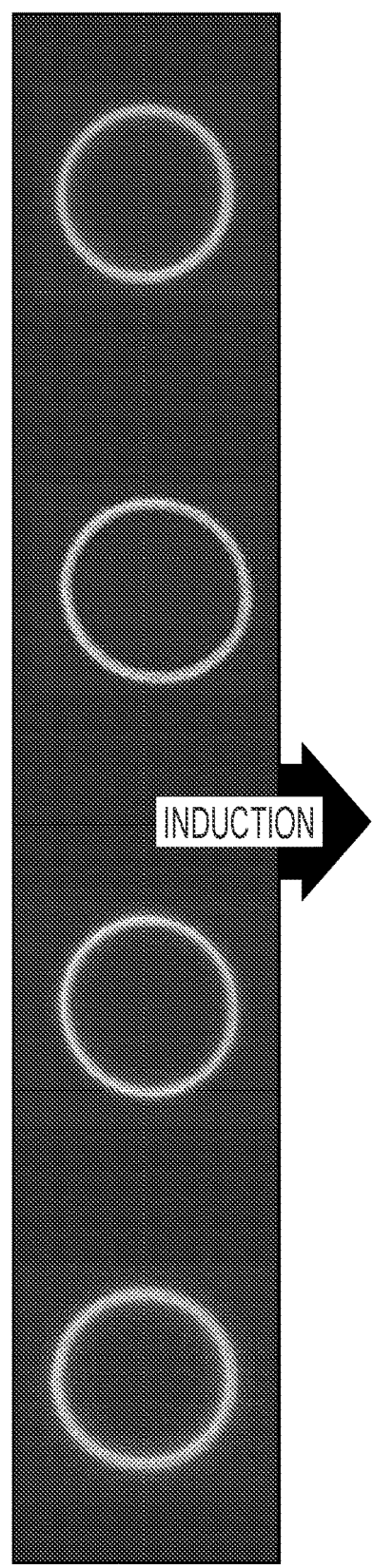
Figure 27A:
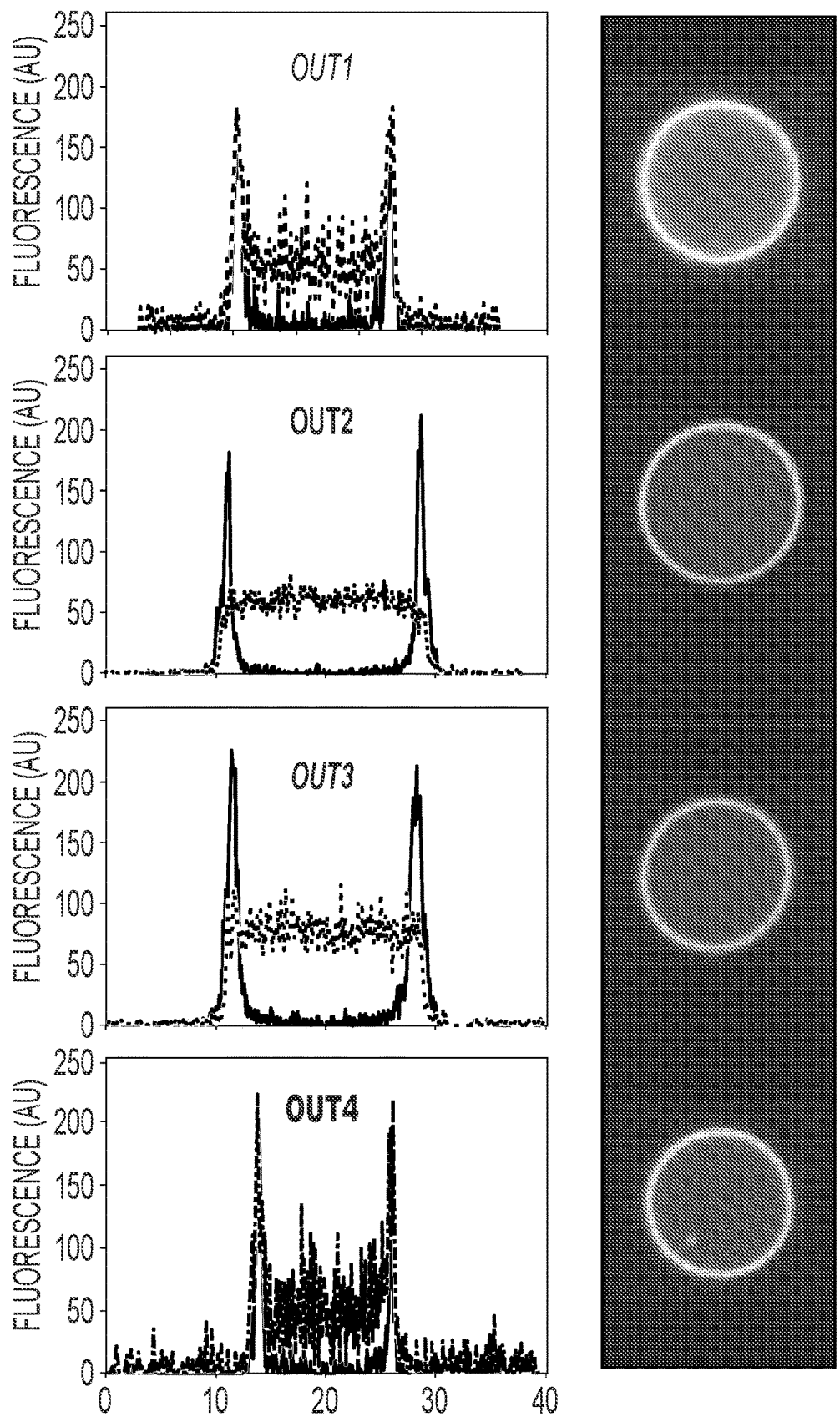

Confocal microscopy also gave precious information on protocell's membrane characteristics. To visualize the membrane, we used a phospholipid bilayer specific dye (i.e. DiIC18) which undergoes drastic increase in fluorescence quantum yield when specifically incorporated into bilayers (67). We obtained well defined images denoting the complete extraction of oleic acid from the double emulsion and a well-structured arrangement of the bilayer (FIGS. 25C and 27A).

Next, in order to validate the encapsulation of biological enzymatic parts inside protocells, we carried out UPLC-Mass spectrometry experiments. We encapsulated two relevant enzymes within protocells: Alcohol Oxidase and Glucose-1-Dehydrogenase. We then performed chromatographic and ESI mass spectrometry analysis on the protocells, and found that we could retrieve the molecular signatures of the enzymes in the interior of protocells, as compared with positive controls (FIGS. 3A-3C).

In addition to confocal and transmission light microscopy, we performed environmental electron scanning microscopy. This technique validated the structure, size and shape of the protocells and yielded esthetic images, but also gave an interesting way to probe and interact with the phospholipid bilayer (FIG. 1).

Therefore, we successfully validated our microfluidic platform for the fabrication of protocells. This set-up proved capable of generating highly stable protocells with high efficiency and user-defined programmable content.

EXAMPLE 8: CONSTRUCTION AND ANALYTICAL EVALUATION OF MEDICAL PROTOSENSORS

A) in Silico Optimization of Protosensor Circuitry

In order to minimize modes of failure and obtain the most robust behavior, we first performed in silico optimization of protosensors before in vitro implementation. More specifically, the initial state concentration parameters of the species constituting the encapsulated synthetic circuit need to be optimized to take into account membrane selective permeability and give fastest results in accordance with the medical algorithm of interest. We thus incorporated membrane parameters in the models describing molecular inputs passively diffusing in and out through hemolysin pores (see Materials and Methods for details). We then defined temporal logic specifications that would best satisfy clinical requirements, that is, obtaining biosensing sensitivities at pathological thresholds, achieve specified signal processing operations, and obtain a measurable output signal in less than 10 minutes for the three systems (FIGS. 7A-7C, See Materials and Methods for details).

Using BIOCHAM, we first performed sensitivity analysis on the models to determine which concentration parameters had the most important influence on the systems' behavior. For each protosensor models, we could identify the two key biochemical species that would constitute the most sensitive components. We then computed 2D sensitivity landscape maps relative to these two dependencies in order to visualize the available biochemical design space for each system (FIGS. 6A-6C). We found that we could define concentration spaces within boundaries of which to implement desired temporal logic. GluONe protosensors function appeared mostly sensitive to G1DH and ADH enzymes concentration. Interestingly, we found that for LacOH and GluNOx, their behavior was more sensitive to the initial concentrations of the metabolite NAD+ than other enzymes. In fact, for all three systems, the NAD+/NADH redox ratio can be seen as a biochemical current connecting the two molecular inputs signals, and thus has to be finely tuned to match input thresholds and enzyme levels.

Last but not least, within this computed design space, initial state concentrations were rationally chosen using BIOCHAM automated parameter search (CMAES Method). This approach enables to achieve optimized robustness of operation while satisfying temporal logic specifications according to each model (FIGS. 7A-7C). The concentrations we obtained were then used to experimentally build the three synthetic circuits embedded in protosensors.

B) Digital Signal Processing and Multiplexing Logic

In order to verify Protocells behavior, we started by mapping in silico their complete transfer function using stochastic HSIM simulations (FIG. 26A). As previously, we plotted heat maps of computed outputs signal after induction with various concentrations of biomarker inputs, using calibrated mathematical relations between molecular concentration and measured signal (FIGS. 8A-8B). We found that Boolean logic was respected with very satisfying theoretical response fold change, as well as near-digital, sharp response profiles. We also found that theoretical switching thresholds for these models matched useful clinical sensitivity for biomarker inputs (pathological thresholds: Ketones>17 µM (~10 mg/dl); Glucose>1.39 mM (~25 mg/dl); Lactate>10 µM; EtOH>17.4 mM (~80 mg/dl)); NOx>1000 µM).

The next goal was then to investigate the behavior of protosensors in vitro. Therefore, we proceeded to microfluidic fabrication of GluONe, LacOH and GluNOx protocells using optimized concentration parameters as previously defined. In a first experiment, we reasoned that a preliminary exploration of models validity would be to achieve the same transfer functions in vitro as previously predicted by simulations. We thus exposed and incubated the three protosensors systems to increasing concentrations of respective input biomarkers, and measured their individual output signal response using flow cytometry. we hypothesized that this technique would give most precise measurements by cancelling sample noise effects in order to get finer verification of protosensors behavior at the single (proto)cell level (FIG. 26B). Interestingly, when comparing these data to HSIM model simulations, we found that the experimentally measured switching thresholds using this technique showed very good agreement with predictions, along with near-digital responses. Although this approach alone is not sufficient to map the complete Logic behavior in response to the combinations of different inputs, which would require extensive experimental sampling, it is a preliminary unidimensional validation of useful analytical properties of these systems. In addition, we have yet to measure the in vitro responses for output 1, which is the focus of ongoing experimental work.

We then sought to further visualize the spatial and analytical digitization of output signals. we used confocal microscopy to quantitatively measure and precisely visualize output signals generation in induced protocells (FIG. 27A). We obtained bright images with high SNRs and important response fold changes. Molecular output signals appeared well localized to the interior of protosensors, although we did not quantify possible leakage. These experimental data strongly corroborate previously flow cytometry acquired data.

Figure 27B:
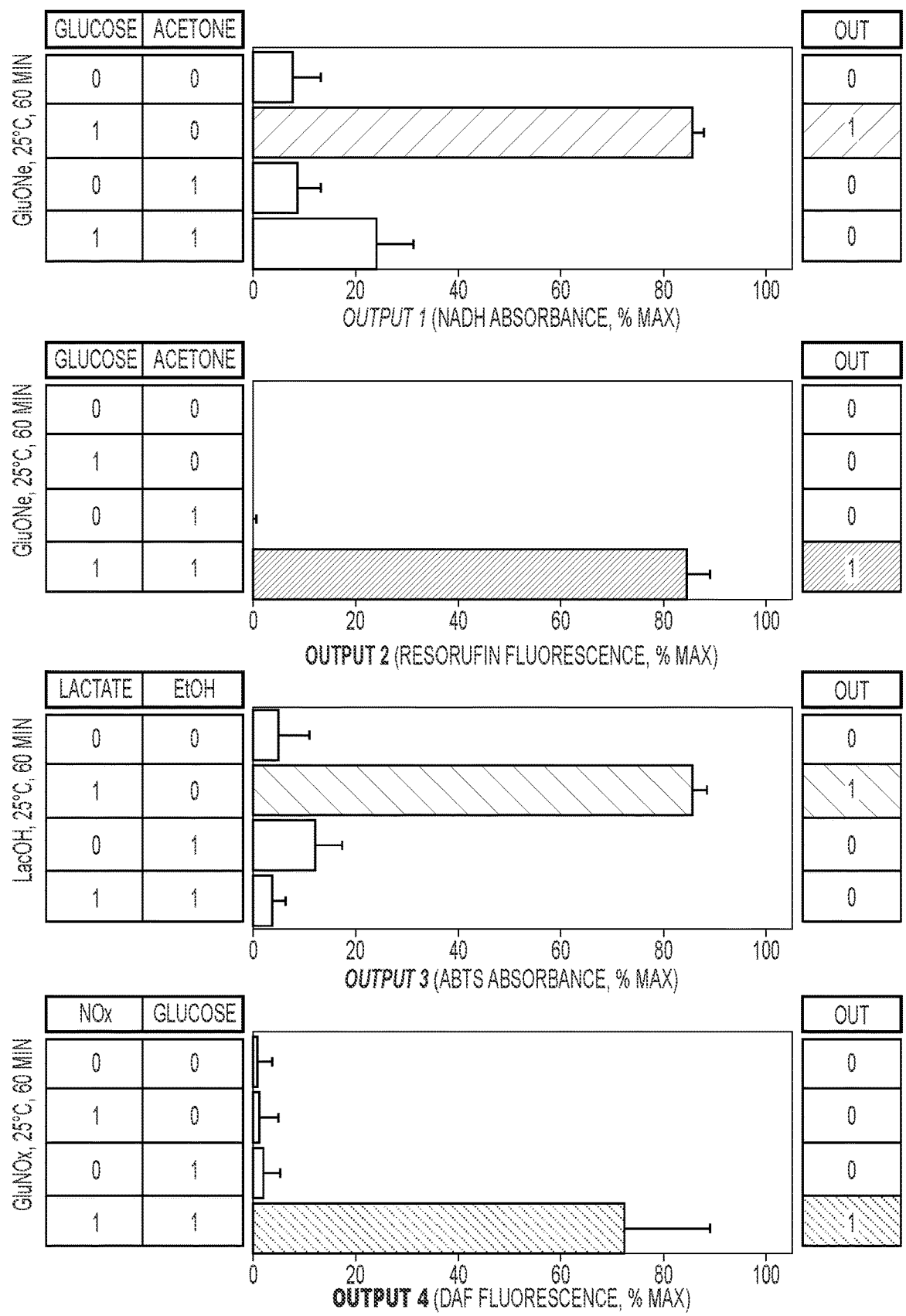

We then performed multiple experiments consisting in mapping the experimental truth tables of the three protosensor systems. We measured output responses at the population level, while varying input conditions (i.e. presence/absence of pathological concentrations of input biomarkers). This allowed us to get a fine understanding of the functioning and detailed experimental characterization of logic operations (FIGS. 27A, 27B and 11). We obtained clear digital-like behaviors with important fold changes and exact accordance to Boolean logic specifications with temporal requirements of less than 60 minutes (FIG. 11). We calculated signal to noise ratio, which showed very good performance SNRs for outputs 1, 2, 3 and 4 of ~8, 35, 5, and 11 dB respectively.

Even though very satisfying for analytical applications, we found greater background noise compared to non-encapsulated synthetic biochemical circuits. We hypothesized that it was due to the introduction of auto-fluorescent species such as surfactant and phospholipids, as well as probable scattering and absorbance phenomenon emerging for spherical protocellular structures in solution.

In fact, the rationale behind encapsulation was to achieve greater analytical robustness and obtain insulation from context, while achieving true composable and multiplexed Boolean logic. In other words, multiple types of protosensors in solution should be able to operate independently in a standardized way without interacting with each other, this way achieving multiplexed analysis of the molecular environment. To verify this assertion experimentally, we first addressed multiplexing logic capabilities. For this purpose, we set up different experiments where we measured output signals in media spiked with multiple biomarkers, using all three synthetic biochemical circuits in either batch mode analysis (i.e. non-encapsulated synthetic circuits) or protosensors analysis (i.e. protocell encapsulated synthetic circuits). We compared the measured output signals obtained to the expected theoretical true outputs. We found that simply mixed synthetic biochemical circuits were incapable of achieving correct signal processing tasks, probably due to molecular interactions between circuits' components. For this experiment, we rationally chose example combinations of biomarkers that would be most likely wrong, although different combination could have given true behavior. On the other hand, mixing the three types of protosensors did not affect biosensing and signal processing capabilities, which were capable of coordinating true Boolean logic and output signal generation (FIG. 27C). Although we did not yet test all the 32 possible input combination that would require extensive experimental work, the data shown here suffices to demonstrate the interest of insulating signal processing biochemical circuits within protocells, thereby increasing the scale in parallelization of biocomputation tasks operating simultaneously.

We then sought to address the potential effects of clinical urine media on protocell structure and operability using flow cytometry (FIG. 27D). We reasoned that measuring protocell fluorescence signal along with forward scattered light (FSC) would give insights on protosensor stability, as FSC is correlated with vesicular size, and internal fluorescence with membrane integrity. We found that induction and prolonged incubation in urine does not impact stability, structure or inducibility of the system. In addition, we found no difference between operation in standard PBS buffer and urine media (FIG. 27B and FIG. 12).

Taken together, these data demonstrate that protosensors enable the implementation of programmed biosensing and biomolecular logic gated operations displaying robust and predictable behavior in situ.

C) Assaying Pathological Clinical Samples: Protosensors Mediated Diagnosis of Diabetes After successful characterization of protosensors analytical capabilities in spiked samples, we then proposed to perform real world diagnostic evaluations. To assess the relevance of protsensors for disease detection in a clinical assay, we sought to evaluate a proof-of-concept that could detect endogenous levels of a pathological biomarker in clinical samples from patients. Although we did not benefit from a large sample library of diabetes related metabolic complication to test the complete implemented diagnostic algorithm in detail, we disposed from previously collected urine samples from naive diabetic patients. These patients presented simple glycosuria with negative ketonuria as confirmed with a urinary dipstick. Therefore, we reasoned that assaying pathological glycosuria in these urine samples would be a good simple testbed evaluation for GluONe protosensors and would provide with a interesting diagnostic evaluation (i.e this satisfies the GluONe algorithm Output 1=Glucose AND NOT Acetone).

We proceeded to incubation of GluONe protosensors with either diabetic urine samples or non-diabetic control urines, and as previously described measured output signal responses (FIG. 28). We also concomitantly performed glycosuria analysis using the clinical gold standard urinary dipsticks. We found very good correlation between output signals from protosensors and visual examination of dipstick. Moreover, we performed Receiver Operating Characteristic (ROC) analysis on these data and found that the assay reliably detected glycosuria in samples from diabetic patients, with a near ~100% sensitivity and specificity, and an Area Under Curve of ~0.9981, which defined GluONe protosensors as an excellent diagnostic test. Together, our data demonstrated that protosensors can discriminate between normal and diabetic patients with excellent diagnostic accuracy. Therefore, We concluded that rational biomolecular programming of protosensors can be used to generate clinical grade assays to detect endogenous biomarkers of disease in patient samples.

Conclusion and Discussion

This study demonstrated that protosensors according to the present invention are highly promising tools to perform multiplexed in vitro diagnostics integrating medically relevant algorithmic processes. As a prototype for the clinics, we showed that this technology could be successfully applied to solve real clinical problems and demonstrated that protocells could overcome several hurdles faced by classical in vitro diagnostics. Although portable, it also offers multiplexed detection and complex analytic capabilities with sharp near-digital response profiles at tunable thresholds, coupled to expert decision making.

We brought rational programming of synthetic biological circuit closer to real world application by addressing some of the previous technological limitations, namely design and scalability. We proposed a systematic computational approach that combined a directed exploration of the design space according to time dependent quantitative and qualitative specifications, to automated robustness optimization of initial parameters for experimental implementation. This ensures that robustness in operation and functionality are maximized and led to successful automated design and construction of synthetic biochemical circuits from vast and comprehensive enzyme databases. Last, we provided a quantitative in silico framework to evaluate the function and analytical properties of protosensors.

We showed that by confining biological complexity within membrane boundaries, one can achieve more complex circuitry by preventing deleterious molecular short-circuits. Moreover, protocell membrane confinement provided a robust architecture to insulate and decouple the biochemical software from crosscoupling with the complex medium it operates in. Complex and susceptive enzymatic activities can thus be confined within protosensors as standardized and insulated sensing and computing units.

Along with computer simulation and assisted design, we demonstrated that these devices could be synthesized using a straightforward, versatile and scalable methodology relying on microfluidics. We envision that the capabilities brought by microfluidics to bottom-up design of protosensors will help bridge the gap towards effective translation to the clinic.

This study paved the way for the development of integrated biochemical circuits capable of sensing their molecular environment, achieving biomolecular signal processing and decision making at the molecular and cell scale. The approach to biosensing described in this study, which relies on autonomous and programmable entities, will be of great interest for novel kinds of local measurements and bioactuation in situ since protosensors can be addressed to specific biological structures or cells through external receptors. In addition, these systems could be engineered into sense-act micromachines where the systems would conditionally generate cell actuation signals or therapeutic responses in situ, as well as integrated or interfacing living systems. They could also be used for high-throughput screening of complex phenotypes or biological functionalities.

A vast landscape of open problems in biology and medicine has remained unsolved due to our inability to grasp biological networks dynamics and process information at the molecular scale. Gaining insights on this phenomenon through a bottom-up and systematic approach to control and design molecular programs acting within biological substrate and interfacing organisms, could be of outstanding interest and bring progress for both basic and applied science

EXAMPLE 9: ENGINEERING UNIVERSAL PROTOCELL BIOCOMPUTERS

In this Example, we present a new kind of computing device that uses spatially constrained biochemical reactions circuits as building blocks to implement logic gates. The architecture of a computing machine relies on these standardized and composable building blocks, computation units, which can be used in multiple instances to perform complex Boolean functions. Standard logical operations are implemented by synthetic biochemical circuits, encapsulated and insulated within synthetic vesicles called protocells. These protocells are capable of exchanging energy and information with each other through transmembrane electron transfer. In the novel paradigm of computation we propose, protoputing, a machine can solve only one problem and therefore has to be built specifically. Thus, the programming phase in the standard computing paradigm is represented in our approach by the set of assembly instructions (specific attachments) that directs the wiring of the protocells that constitute the machine itself. To demonstrate the computing power of protocellular machines in a practical example, we apply it to solve a NP-complete problem, known to be very demanding in computing power, the 3-SAT problem. We show how to program the assembly of a machine that can verify the satisfiability of a given Boolean formula. Then we show how to use the massive parallelism of these machines to verify in less than 20 min all the valuations of the input variables and output a fluorescent signal when the formula is satisfiable or no signal at all otherwise.

A) Introduction

What is Computation? One definition could be the goal-oriented process that transforms a representation of input information into a representation of output information. The process itself can be iterative (or in another form recursive), in this case it is called an algorithm, but other forms of processing can be used, such as neural networks or first order logic.

A computation process, whatever it is, has to be run by a computer, which can be a human using pen and paper, or a machine specifically built for that purpose. The most popular form of computer is an electronic device that uses a digital representation of data, and manipulates this representation according to a set of instructions that implements the algorithm transforming them into results. The set of instructions is then called a computer programme. Electronic computers use numbers, integer and floating points, to represent data. These numbers are commonly coded in base 2, which can also be directly used to encode Boolean values and therefore easily implement conditional calculations. Electronic computers are mainly built from basic blocks, logic gates, which are interconnected to make the arithmetic and logic units, memory registers and microcontrollers that form the Central Processing Unit which in turn, along with the Main Storage Unit, and the I/O Controllers constitute the computer itself.

Therefore, one can build a digital computer using any technology that can mimic logic gates and their interconnections. We intend to demonstrate in this article how to implement single Boolean logic gates using synthetic minimal biological systems embedded in a vesicle, or protocell, and how to connect them together to fabricate a device, or protocellular machine, that computes a complex logical function. The computing model that underlies our biochemical implementation of a computer is similar to the one of an electronic computer, giving their computing capabilities are the same.

The fundamental characteristic of electronic computers is their ability to run a potentially infinite number of algorithms doing a wide variety of computations on data, because they are programmable: the same computer can run sequentially (or pseudo-concurrently) as many different programmes as those that can reside in its main memory storage, along with the associated data.

Here, we propose a methodology where programming the computer is analogous to its physical assembly. The program thus resides in the set of instructions given for the assembly process. Furthermore, we show how to build (i.e. program) a kind of computer that can solve one problem belonging to a class known to be hard to solve: a NP complete problem.

The computational complexity theory explores the feasibility of computational problems, in terms of computing time (or memory space) needed to solve a problem of a given size. In the Von Neumann based architectures (standard electronic computers) the number of computing elementary steps (instructions) is often used to approximate the computing time, since each instruction takes approximately the same amount of time to be performed.

There are two main classes of computational problems, those that can be solved by a deterministic machine in a number of steps which can be expressed as a polynomial of the problem size (class P), and those that can be solved in polynomial time, but on a non-deterministic machine (class NP). Typically decision problems where (i) a solution can be verified in polynomial time and (ii) there is no other known algorithm except generate and verify all the potential solutions, are NP problems. Solving these problems on a Von Neumann computer requires an exponential number of steps with respect to the problem size. A NP problem is said to be NP-complete if any other NP problem can be transformed into this problem in polynomial time (104). In consequence NP complete problems are more difficult to solve than any other NP problems because if one NP-complete problem is quickly solved (in polynomial time) then all the NP problems will be quickly solved. Of course all these complexity classes collapse if P=NP (which is one of the great open conjectures in computer science).

We have chosen the 3-SAT problem, a variant of the boolean satisfiability problem (SAT), as an example of NP-complete problem 660 a protocellular computer can solve elegantly. This is mainly because the very small size of protocells and their 3D packing allow us to build a machine made of billions of logic gates specifically connected to solve a given 3-SAT problem. Another characteristic of our protocellular machines is that they are disposable in the sense that once the computation is done for a given set of input values, the machine is no more usable. But the counterpart is that the energy needed for the computation is very low (19). Finally, the biochemical nature of the protocellular machines makes them very easy to interface with living organisms. For example, they can be used for medical diagnosis to implement biosensing coupled with medical decision algorithm

B) Methods

1. Protocells as Computation Units: Definitions

The bottom-up design of biological systems is made possible by the synthetic biology approach that applies engineering principles to biology in order to design standardised biological parts, devices, systems in a systematic and rational manner. Hierarchical abstraction of biological functions enables the assembly at the system level of new biological systems with user-defined functionalities (1,2,3). The behavior of synthetic systems is predictable and design can be automatised in silico before attempting to implement them with biological components (33). In addition, the remarkable capacity of biological building blocks to compute in highly sophisticated ways has led scientists to design and engineer biomolecular computers (5). Thus far, most biocomputing has been investigated from the top down perspective, that is, by modifying existing organisms (20). The strategy we propose here, protoputing, is interested in implementing protocols from the bottom-up perspective to perform computation, where very little attention has been given (27, 26,15).

Starting from an abstract operation that is to be computed, one can rationally and systematically choose biochemical species for the implementation (metabolites, enzymes, nucleic acids . . . ) (FIG. 29A). Standardised and robust biomolecular components and reactions can be engineered, tested and optimised to implement different types of biological functions or computations (31): simple Boolean operations, memory devices, amplifiers, analog to digital converter, oscillators etc. (FIG. 29B). This process can be automatised using CAD tools. For example, an AND biochemical logic gate taking reduced metabolites as inputs (NADPH and FADH2) can be implemented using a network of 3 different enzymes and 4 different metabolites connected by 3 biocatalytic reactions, and transferring electrons to NADH as an output. In the same way, we can implement a set of standardised computation units that recapitulate all Boolean logic gates (see FIG. 31 for examples of implementations of AND, NOT and NOR gates). Electron transfer can also be coupled to various output biological functions to produce human readable signals (FIG. 30) or enable the selection of machines with specific behavior for further analysis. We propose to exploit specific reduction of species to trigger readable outputs, either luminescence or fluorescence (i.e. reduction of rezasurin into fluorescent resorufin) or the transport of a ligand (or its receptor).

Our approach improves the modularity of biomolecular computing systems by the fact that biochemical networks implementing Boolean logic are encapsulated within synthetic vesicles, or protocells, distinguished by their high degree of organization and control over biological processes provided by the membrane boundary (16). Such architecture of insulated computing units allows us to use many instances of the same type of protocell anywhere in the circuit when the same logic gate is needed. Moreover, this enables the concatenation of multiple layers of protocells to achieve complex information processing capabilities. In such architectures, input information arrives from upstream connections with previous protocells, to output connections to following computation units. As each logic gate is encapsulated within an impermeable vesicle, the reactions that compute the output value will go from the non-equilibrium initial state to an equilibrium state. Therefore, once a logic gate has finished to compute the output, it is no more able to do another computation. So this first model of protocellular machine is in essence a kind of disposable computer.

Encapsulation of biochemical networks can be achieved using natural bilayer membranes (e.g. phospholipid bilayers, liposomes) (14), or engineered membranes (e.g. copolymers, polymersomes) (17), with respect to stoichiometry of internal species and incorporation of membrane proteins for connections (81, 29,18). This process is also known to stabilise enzymes, prevent cross-talk, denaturation or proteolysis and improve enzymatic properties (82, 83). In addition, streamlined workflows, for example relying on microfluidics as we discussed previously, are already available for the high-throughput generation of protocells that encapsulate various substrates (53, 84, 85). This strategy, extensively used in our lab, allowed us to test the implementation of various protocellular logic gates. Such vesicle have proven to be sufficiently stable (i.e. not prone to fuse together or physical disruption) to enable the construction of such multi vesicular assemblies (86, 56). Tunable sizes ranging from 50 nm to 50 μm can be obtained, although in our approach, size should be kept as small as possible to obtain the highest density of computing operators.

2. Circuit Wiring

To obtain a full circuit implementing a given Boolean function, we then need to concatenate and wire basic logic gates. The design of a function-specific protocellular machine exploits the composability of computation units. Amongst a specific set of protocells, multiple instances of the same logic gates can be wired together to implement a user-defined function. One way to achieve successive reactions in each layer of a protocellular machine, from input to output protocells, is to drive them using electrochemical potential (e.g. oxido-reduction reactions). By analogy with electronic computers, electrons are energy carriers and the redox potential is the current of the system, which could be measured with an electronic device. The major difference is that inside a protocell, wires are replaced by free molecules (e.g. NADH, NADPH, FADH2), and effective wiring is achieved using chemical selectivity of enzymes. Molecules are either electron donors or acceptors, obeying biological enzymatic rules resulting in current and energy for computation. In such systems, the in ->out direction is driven by the thermodynamics of the redox reaction. In our example, a protocell giving the true value would have a reductive state with high concentration of NADH, which can then transfer its electron to reduce the input of the next protocell. Conversely, a protocell giving the falsevalue does not output any electron. In addition, electron transfer occurs only between physically connected protocells, through tight junctions putting into close contact electron transfer complexes, which carry out the connections between protocells and therefore between logic gates (FIG. 31).

Here, we propose build a protocellular machine from a set of protocell logic gates assembled in a tree-like layout (see the following section). When set to true, the inputs of the machine initiate electron transfer through the chain of protocells that constitutes each branch of the tree, down to the root protocell.

In these input protocells, electron production is started by the specific oxidation of molecular species by oxidase enzymes. Electrons are then transferred down the protocell chain via transmembrane electron transport complexes that enable electron coupling (reduction) of specific molecular species. In that sense, input protocells can be seen as the generators that power the machine. Moreover, fuel protocells with a switch like behavior, could be used to amplify and reshape the signal and therefore counteract its decay.

In order to implement specific electron transfer modules, we propose to exploit the modularity and thermodynamic reversibility of natural oxidative phosphorylation and photosynthesis complexes, which catalyse the electron transfer across natural membranes with specificity to NADH (Complex I), FADH2 (complex II), and NADPH (NADPH quinine oxido reductase) (87). This includes quinone (or chemically related) and cytochrome c shuttle, which are delocalised mobile electron carriers that could be used as inter-protocell transfer molecules. In our design, we propose that a first quinone carrier (or related), could transfer electrons from a specific output signal (substrate specificity given by the first complex: I, II . . . ) to a close complex III, which would then via a mobile cytochrome c transfer these electrons forward to the complex III belonging to the next protocell. This mechanism constitutes efficient reversible energy coupling, which has been shown to work via electron-tunneling across the proteins (87). Furthermore, recent studies have highlighted the possibility to engineer natural prokaryotic complexes for efficient and substrate specific synthetic electron transporters (88-90).

The architecture of a machine is controlled by the functional wiring of input and output of specific protocells. This can be achieved by using programmable junction modules, which can be selected to implement any protocellular machine in a plug- and play way (FIG. 31). Biological function for these programmable attachments could be supported by couples of ligand/receptors with high binding affinity, such as aptameric nucleic acids (91, 92) or peptidic binders (93), that could be straightforwardly produced in large combinatorial synthetic libraries using SELEX (94), or ribosome display respectively (95, 96). Starting from a pre-built stock of computation units, the user can define a set of attachment instructions that corresponds to the Boolean function to implement. Irreversible constructs can be achieved using cross-linking chemicals, so that no unbinding would occur (97,98). We assume that the kinetics associated with such an assembly process would be of the order of minutes. Some attachments can also be set as random, to enable stochastic wiring of different types of protocells to specific positions. This could be used for example to solve problems involving the navigation through a large parameter space where protocellular machines could be used to compute a fitness function. Additionally selection methods could be implemented to isolate protocellular machines that exhibit specific behaviors. Positive selection can be done for example using FACS, conversely negative selection via a self-destruction mechanism.

C) The Case Study

1. The Boolean Satisfiability Problem

The NP-complete problem we aim to solve is the 3-SAT problem. This problem can be simply defined as:

Given any boolean formula in Conjonctive Normal Form (CNF), with at most 3 litterals per clause, is there a valuation of the variables that satisfy the formula?

In other words, it asks whether the variables of a given Boolean formula can be consistently replaced by the values true or false in such a way that the formula evaluates to true. If it is the case, the formula is called satisfiable. The litterals are either a variable (v) or the negation of a variable ($\neg$Iv); They are connected with the or operator ($\lor$) to form a clause; The clauses are connected with the and operator ($\land$) to obtain the formula in CNF. For example:

$$F(a,b,c)=(a\lor\neg b\lor c)\land(b\lor\neg c)\land(a\lor b) \quad (1)$$

is true when a=true, b=true, c=false, so the formula F(a, b, c) is satisfiable. Conversely, the formula:

$$G(a,b,=(a\lor b\lor c)\land(\neg a\lor b)\land(b\lor\neg c)\land\neg b) \quad (2)$$

is not satisfiable because all the eight possible valuations for a; b; c lead to G=false.

To find if a formula is satisfiable, we will build as many protocellular machines as there are combinations of valuations of the input variables. To do this, we will exploit the combinatorial power of ligand-receptor binding to link constant protocells (with false or true values) to the inputs of the protocellular machine to cover all the value space. A protocellular machine is dedicated to a specific formula, and therefore is not programmable in the sense an electronic computer is. The protocellular machines are self-assembled according to the formula they have to check, so in our approach, the program is the process that directs the assembly of the machines. We will ascertain that there is at least one instance of a protocellular machine per possible valuation of the variables.

An instance of the machine can be made using 2- and 3-inputs OR gates connected to a big AND gate with as much inputs as there are clauses in the formula. Each input of a clause is connected to a protocell representing a variable v sending true or false when a specific start signal is given, or to an inverter protocell sending the negation of v when the start signal is given. The output of the AND gate is connected to a protocell that fluoresces when the input value is true. For example, the protocellular machine corresponding to the G formula would be made of a 4-input AND gate, two 2-input OR gates, one 3-input OR gate and three inverters connected as in the equation above (FIG. 32A).

As we have at least one (and probably more) instance of the machine for each possible valuation of the variables, if at least one of the protocellular machines fluoresces, the formula is satisfiable. Conversely, if there is no fluorescence at all then the formula is not satisfiable.

We can simplify the construction of the machines using the De Morgan laws to replace the big AND gate by a NOR gate, which is easier to build and also more efficient than an AND gate when there is a lot of inputs. Since the output of this NOR gate is the output of the whole machine, the final inverter can be made using an inhibitor of the fluorophores stored inside the protocell implementing the gate. We also need to feed the inputs of the AND gates with the complement of the variables, which could lead us to use a lot of inverters; But they can be avoided because these inputs are the inputs of the whole machine, and since we need to test all the valuations of the variables, these inputs will be fed with constant values. Therefore we can program the assembly of a machine with the constants already inverted (FIG. 32B) and we will need no more inverters than negated variables specified in the original formula.

2. The Assembly of the Machines

To obtain one instance of a computing protocellular machine, we need to direct the self-assembly of as many copies of AND gate protocells as there are clauses in the formula (except when a clause has only one litteral), the output of each AND gate being connected to an input of a fluorescent NOR protocell. The inputs of each AND gate are also to be connected to the output of an inverter or to the output of a wiring protocell (representing the input variables of the formula). Then, to test a valuation of the variables of the formula, the input of each wiring protocell will be connected to special inputless protocells that output the constant value true or false. Once the machine and its inputs are assembled, when a start signal is given, after a few minutes, the NOR gate of this machine will fluoresce if the formula is true for this valuation of the variables, and therefore the formula is satisfiable.

We must ensure that correlated inputs of two (ore more) AND gates are fed with correlated values. In the previous formula (rewritten using a NOR of ANDs, with the complemented variables as shown in FIG. 32B)

$$G(a,b,c) = \overline{(a \wedge \bar{b} \wedge \bar{c}) \vee (\neg a \wedge \bar{b}) \vee (\bar{b} \wedge \neg c) \vee \neg b} \quad (3)$$

The first input of the first clause, a, is always the opposite of the first input of the second clause (¬a), and the second input of the two first clauses, $\bar{b}$ have always the same value, etc. To achieve that we will use inverter protocells, and wire protocells that can transfer their input to two or more outputs.

In this example, since there are 3 variables, we must assemble 8 protocellular machines to test each of the 8 possible valuations. Each line of the table in Table 3 shows the input values (0 for false, 1 for true) of one of the 8 different protocellular machines, the complemented value of each clause, and the value of the formula (3), which is always false (this formula is not satisfiable).

In order to have an efficient assembly mechanism, we split the process in two steps. The first one does not depend on a specific formula, but on the maximal numbers of variables (Vmax) and of clauses (Cmax) a formula can have. To be able to test any given formula within the limits of size we stated, we build a reservoir containing at most for one protocellular machine instance:

one Cmax-input NOR gate
Cmax 2- and 3-inputs AND gates.
Vmax inverter protocells
2.Vmax types of inputless constant protocells, outputting the constant false or true to represent the two possible values of each variable.
a formula dependent number of wiring protocells that duplicate their input to two (or more) outputs in order to cast each constant protocell output to the appropriate AND input or inverter.

TABLE 3

Complemented value of each clause for the eight possible valuations of the variables, and the corresponding value of the formula.

| $\bar{a}$ | $\bar{b}$ | $\bar{c}$ | $\bar{c}_1$ | $\bar{c}_2$ | $\bar{c}_3$ | $\bar{c}_4$ | G (a, b, c) |
|---|---|---|---|---|---|---|---|
| 0 | 0 | 0 | 0 | 0 | 0 | 1 | 0 |
| 0 | 0 | 1 | 0 | 0 | 0 | 1 | 0 |
| 0 | 1 | 0 | 0 | 1 | 1 | 0 | 0 |
| 0 | 1 | 1 | 0 | 1 | 0 | 0 | 0 |
| 1 | 0 | 0 | 0 | 0 | 0 | 1 | 0 |
| 1 | 0 | 1 | 0 | 0 | 0 | 1 | 0 |
| 1 | 1 | 0 | 0 | 0 | 1 | 0 | 0 |
| 1 | 1 | 1 | 1 | 0 | 0 | 0 | 0 |

Of course we can have a larger number of copies of these building blocks if we want to test more than one instance of the formula. We can remark that depending on the formula we want to test, all the Cmax inputs of the NOR gate are not used and will stay not connected to any output, which is equivalent to a false value and so these inputs will not interfere with the computation since we are certain that nothing can be bound to them.

To verify the satisfiability of a formula made of N/Vmax variables and C/Cmax clauses, we need to build 2N protocellular machine instances, (at least) one per possible valuation of the input variables. The building of these protocellular machines constitutes the second step. Although this step is specific to a given formula, its principle is generic enough to be applied to any formula. This resemble to the compilation phase of a programme written in a high level programming language on a standard computer.

To assemble a machine we will program the binding of each input of one NOR gate to the output of a 2-inputs or a 3-inputs AND gate, or to one output of a wiring protocell, or to the output of an inverter. We will also need to program the binding of one wiring protocell per variable to some inverter, AND or NOR input, according to the formula. Then, to test a given valuation of the variables, we will need to bind the constant protocells corresponding to each variable of the formula to the inputs of this machine.

These programmed bindings are made possible because all the protocells in the reservoir have been built with specific tags on their inputs and outputs. These tags can be peptides/nucleic acids with a unique sequence to address them. The process of binding itself will be done by putting in the environment specific molecular attachment instructions that recognise and bind the tag on the output and the tag on the corresponding input. This will enable the binding of specific protocells together (FIG. 33).

Each input of the NOR gate is labeled with a tag implementing the number of the corresponding clause (0 to Cmax−1). Similarly the output of each of the AND gate is labeled with the same number. Therefore, to connect an AND gate to the corresponding input of the NOR gate for one protocellular machine, we have to synthetize a molecular attachment that match at one end the tag labelling the output of the AND gate and at the other end, the tag labelling the input of the NOR gate.

The same mechanism is used for the input variables of the formula. The input of a wiring protocell that corresponds to a variable of the formula is labeled with a tag representing the variable number (0 to Vmax−1). The constant protocells used for each variable, whether their output is false or true, are labeled with a tag matching the corresponding wiring protocell of the machine. Since there is a high number of constant protocells in the medium, the false and trueversion for each variable will be randomly bound to the corresponding input of the machines, and after some time, all the possible valuations will be covered.

It is important to notice that we must use constant protocells that output the Boolean value false, even if a non connected input is equivalent, because when we want to test a valuation where some variable is false, we must be certain that no true constant protocells can be bound to this input.

3. The Computation Process

The computation process may begin when we are certain that at least one copy of a protocellular machine is bound to each possible combination of input values. This process is started by remotely triggering the whole population of true constant protocells and inverter protocells using, for example, light switchable enzymes (e.g. a tryptophan dehydrogenase engineered to bear a photoswitch moiety) (99, 100, 101).

Since all the machines run concurrently to compute the value of the formula, the total computing time is the time needed either by the first one that output true (that become fluorescent) or when we can be certain that the slowest machine that outputs false has finished (in this case they all do). If there is a small number of protocellular machines that fluoresce, we could enhance the signal/noise ratio by scattering the solution into several parts such that the concentration of the fluorescent machines would appear higher, and so helps its detection. Another way to easily detect the first (and possibly only) protocellular machine that outputs true would be that this machine triggers the fluorescence of those in its neighbourhood, and so increase the global fluorescence. Independently of the formula we want to test, the maximal number of reactions needed from one input to the output is very small: one inverter, a small number of wiring protocells, one AND, and one NOR.

Considering the kinetics of enzymatic processes for these simple reactions, we could assume that the calculation time of a single protocell (i.e. the time required for effective electron transfers though the protocell) would be in the order of a few minutes. The computation time for one protocellular machine would then be proportional to the number of layers of this machine. The total computing time would not exceed 20 min, whatever the number of protocellular machines is needed to solve the problem. This is of course mainly because the computing process is massively parallel and to a lesser extent because each processor is dedicated to the specific problem we want to solve.

Since the size of a complete protocellular machine is of the order of magnitude of a micron-cube, even less, we can have more than $10^{12}$ machines in a few ml of solution. As $10^3$ is approximately equal to $2^{10}$, we could theoretically have about $2^{10(12/3)}=2^{40}$ machines in a few ml. Therefore using this technique, we could potentially solve any 3-SAT problem involving up to 40 variables in a few minutes. If we suppose that an electronic computer needs 1 µs to generate and test one valuation of the variables, the average computing time would be of the order of $10^{12} \cdot 10^{-6}$ s, which is more than 11 days and a half. Moreover, if we suppose we use a low power electronic computer, for example 20 watts, the energy consumed at the end of the 11.5 days would be $10^6 \cdot 20 = 2.10^7$ J (~5.5 kWh), compared to a few joules for the protocellular machines.

4 Conclusion

The case studied here is an example of the kind of problem we could address with protocellular biocomputing machines. Here we proposed a machine assembly mechanism (i.e. computation units wiring or program instructions) that relies on highly derivable and easily synthesizable biochemical substrate, such as nucleic acids or peptides bonds. However, thermodynamic, binding and kinetic validity of this approach needs to be investigated before reaching practical experimentation. In addition, for this reason making the very large number of instances of protocellular machines required to verify the satisfiability of a large formula is a bit speculative at the present day. Although highly theoretical, as we demonstrated in the previous chapter the governing mechanisms used to engineer protocell computation units are already under test in the lab. Many implementations of logic gates (much more than those shown in FIG. 33 have been tested in silico using the HSIM (12) simulation system and proven to be functioning in vitro.

Here, we propose to circonvent the classic silicon based approaches of serial computing (FIG. 34), to massively parallel computing strategies taking advantage of the extremely small scale of protocellular computing devices. The computing time we claim, approximately one thousand times faster than a traditional electronic computer for a specific class and size of problem, is also a bit provocative, but the fact remains that this is an example of how to use the really massive parallelism of protocellular machines in order to solve dedicated problems (e.g. for N variables and a problem of size p the time required to evaluate all valuations: t~pN and t~k·p, for a serial computer and a consortia of protocellular machines respectively).

Moreover, to our knowledge, this is the first described case where a synthetic biochemical computer could realistically compete with the speed of electronic computers, while being far less demanding in terms of energy. Nevertheless, in our opinion, the most exciting perspective of protocellular machines is that they are electronically and biologically interfaceable. Our approach allows us to design any given boolean function that can be connected and triggered by any biological and/or electronical input, and generate chosen outputs in a similar way. Thus they could be incorporated in living organisms, or into hybrid electronic/biological systems.

Another interesting application field involves cryptography (e.g. protocellular ciphers). This could be extended to new approaches to disease diagnosis, since a pathological state is in fact an unknown function of molecular patterns (i.e. physiologically encrypted), and elucidation of the specific cryptographic algorithm is analogous to finding a diagnostic algorithm.

EXAMPLE 10: BCAAS AND DIABETES

Recently, much evidence has been found implicating branched-chain amino acids (BCAA) in early insulin resistance. High-throughput profiling of patients could predict patients at risk as early as twelve years before the development of diabetes. Among all the metabolites, the BCAAs appear to be those presenting the highest significant association with future insulin resistance. The system we designed allows quick and rapid assessment of insulin resistance vs diabetes. It cans easily be use on biological fluids such as blood, urine, saliva, etc. The systems performed a simple decision algorithm implemented by our biological networks in a vesicle (see FIGS. 35A-35).

BCAAs are essential amino acids that are catabolized and stored mainly in adipose and muscular tissues. The impairment of their catabolic pathway, resulting in high plasma levels of BCAA, might result in lipogenesis via stimulation of insulin secretion and TCA anaplerosis with consequent accumulation of lipid species like triacylglycerols (TAG) and diacylglycerols (DAG) contributing for lipotoxicity and inflammation. Moreover, the branched-chain amino acid metabolite 3-Hydroxyisobutyrate was shown to be involved in the stimulation of endothelial free-fat acids transport which would be related to intracellular accumulation of TAG and DAG. In this scenario, glucose utilization might be considered as superfluous and, under these conditions, the chronic over-activation of mTOR, S6K-1, JNK and IRS1 (insulin receptor substrate 1) could result in insulin resistance (105-107).

TABLE 4

The table presents diverse HOMA (Homeostasic model assessment of insulin resistance) and body mass index (BMI) submitted to the proposed BCAA enzymatic test according to the invention

|       | a600nm | HOMA | sexe | BMI   |
|-------|--------|------|------|-------|
| 01BAA | 0.291  | 2.44 | F    | 35.89 |
| 04WIL | 0.337  | 5.97 | F    | 35.40 |
| 08GIA | 0.405  | 8.58 | F    | 37.42 |
| 10BOL | 0.356  | 3.60 | F    | 47.52 |
| 13THM | 0.284  | 3.82 | F    | 27.47 |
| 14MAT | 0.244  | 2.60 | F    | 39.45 |
| 18MOP | 0.273  | 3.18 | F    | 40.70 |
| 24RUH | 0.279  | 1.52 | F    | 21.40 |

TABLE 4-continued

The table presents diverse HOMA (Homeostasic model assessment of insulin resistance) and body mass index (BMI) submitted to the proposed BCAA enzymatic test according to the invention

|  | a600nm | HOMA | sexe | BMI |
|---|---|---|---|---|
| 03TIG | 0.369 | 9.50 | M | 39.68 |
| 05EVA | 0.324 | 9.26 | M | 59.54 |
| 06DEM | 0.297 | 1.77 | M | 28.90 |
| 09LLG | 0.492 | 11.09 | M | 35.92 |
| 21MLG | 0.293 | 1.97 | M | 44.00 |
| 23GAA | 0.351 | 1.73 | M | 37.30 |

Sera from patients from a general population presenting diverse HOMA (Homeostasic model assessment of insulin resistance) and body mass index (BMI) were submitted to the proposed BCAA enzymatic test. The FIG. 36 shows a strong correlation between the measured seric BCAA and the HOMA parameter measured in a classic test.

BIBLIOGRAPHY

1. Purnick, P. E. M. & Weiss, R. The second wave of synthetic biology: from modules to systems. Nat. Rev. Mol. Cell Biol. 10, 410-422 (2009).
2. Canton, B., Labno, A. & Endy, D. Refinement and standardization of synthetic biological parts and devices. Nat. Biotechnol. 26, 787-793 (2008).
3. Endy, D. Foundations for engineering biology. Nature 438, 449-453 (2005).
4. Smolke, C. D. Building outside of the box: iGEM and the BioBricks Foundation. Nat. Biotechnol. 27, 1099-1102 (2009).
5. Benenson, Y. Biomolecular computing systems: principles, progress and potential. Nat. Rev. Genet. 13, 455-468 (2012).
6. Courbet, A., Endy, D., Renard, E., Molina, F. & Bonnet, J. Detection of pathological biomarkers in human clinical samples via amplifying genetic switches and logic gates. Sci. Transl. Med. 7, 289ra83-289ra83 (2015).
7. Salis, H., Tamsir, A. & Voigt, C. Engineering bacterial signals and sensors. Contrib. Microbiol. 16, 194-225 (2009).
8. Raut, N., O'Connor, G., Pasini, P. & Daunert, S. Engineered cells as biosensing systems in biomedical analysis. Anal. Bioanal. Chem. 402, 3147-3159 (2012).
9. Wang, B., Barahona, M. & Buck, M. A modular cell-based biosensor using engineered genetic logic circuits to detect and integrate multiple environmental signals. Biosens. Bioelectron. 40, 368-376 (2013).
10. Su, L., Jia, W., Hou, C. & Lei, Y. Microbial biosensors: A review. Biosens. Bioelectron. 26, 1788-1799 (2011).
11. Rialle, S. et al. BioNetCAD: design, simulation and experimental validation of synthetic biochemical networks. Bioinformatics 26, 2298-2304 (2010).
12. Amar, P. et al. A stochastic automaton shows how enzyme assemblies may contribute to metabolic efficiency. BMC Syst. Biol. 2, 27 (2008).
13. Rizk, A., Batt, G., Fages, F. & Soliman, S. A general computational method for robustness analysis with applications to synthetic gene networks. Bioinformatics 25, i169-i178 (2009).
14. Noireaux, V. & Libchaber, A. A vesicle bioreactor as a step toward an artificial cell assembly. Proc. Natl. Acad. Sci. U.S.A 101, 17669-17674 (2004).
15. Smaldon, J. et al. A computational study of liposome logic: towards cellular computing from the bottom up. Syst. Synth. Biol. 4, 157-179 (2010).
16. Elani, Y., Law, R. V. & Ces, O. Vesicle-based artificial cells as chemical microreactors with spatially segregated reaction pathways. Nat. Commun. 5, 5305 (2014).
17. Kamat, N. P., Katz, J. S. & Hammer, D. A. Engineering Polymersome Protocells. J. Phys. Chem. Lett. 2, 1612-1623 (2011).
18. Peters, R. J. R. W. et al. Cascade Reactions in Multi-compartmentalized Polymersomes. Angew. Chem. Int. Ed. 53, 146-150 (2014).
19. Sarpeshkar, R. Ultra low power bioelectronics: fundamentals, biomedical applications, and bio-inspired systems. (Cambridge University Press, 2010).
20. Khalil, A. S. & Collins, J. J. Synthetic biology: applications come of age. Nat. Rev. Genet. 11, 367-379 (2010).
21. Archana Chugh, P. B. Synthetic Biology Based Biosensors and the Emerging Governance Issues. Curr. Synth. Syst. Biol. 01, (2013).
22. Shetty, R. P., Endy, D. & Knight, T. F. Engineering BioBrick vectors from BioBrick parts. J. Biol. Eng. 2, 5 (2008).
23. Breitling, R. & Takano, E. Synthetic biology advances for pharmaceutical production. Curr. Opin. Biotechnol. 35, 46-51 (2015).
24. Ye, H. & Fussenegger, M. Synthetic therapeutic gene circuits in mammalian cells. FEBS Lett. 588, 2537-2544 (2014).
25. Semenov, S. N. et al. Rational design of functional and tunable oscillating enzymatic networks. Nat. Chem. 7, 160-165 (2015).
26. Luisi, P. L. & Stano, P. The minimal cell the biophysics of cell compartment and the origin of cell functionality. (Springer, 2011). at <http://site.ebrary.com/id/10427796>
27. Protocells: bridging nonliving and living matter. (MIT Press, 2009).
28. Noireaux, V., Maeda, Y. T. & Libchaber, A. Development of an artificial cell, from self-organization to computation and self-reproduction. Proc. Natl. Acad. Sci. 108, 3473-3480 (2011).
29. Huang, X., Patil, A. J., Li, M. & Mann, S. Design and Construction of Higher-Order Structure and Function in Proteinosome-Based Protocells. J. Am. Chem. Soc. 136, 9225-9234 (2014).
30. Chandran, D., Bergmann, F. T., Sauro, H. M. & Densmore, D. in Design and Analysis of Biomolecular Circuits (eds. Koeppl, H., Setti, G., di Bernardo, M. & Densmore, D.) 203-224 (Springer New York, 2011). at <http://link.springer.com/10.1007/978-1-4419-6766-4_10>
31. Koeppl, H. Design and analysis of bio-molecular circuits. (Springer, 2011).
32. Shinar, G. & Feinberg, M. Structural Sources of Robustness in Biochemical Reaction Networks. Science 327, 1389-1391 (2010).
33. Marchisio, M. A. & Stelling, J. Computational design tools for synthetic biology. Curr. Opin. Biotechnol. 20, 479-485 (2009).
34. Mendes, P. et al. in Systems Biology (ed. Maly, I. V.) 500, 17-59 (Humana Press, 2009).
35. Matsuoka, Y., Funahashi, A., Ghosh, S. & Kitano, H. in Transcription Factor Regulatory Networks (eds.

35. Miyamoto-Sato, E., Ohashi, H., Sasaki, H., Nishikawa, J. & Yanagawa, H.) 1164, 121-145 (Springer New York, 2014).
36. Kaznessis, Y. N. in Methods in Enzymology 498, 137-152 (Elsevier, 2011).
36. Chaouiya, C. et al. SBML qualitative models: a model representation format and infrastructure to foster interactions between qualitative modelling formalisms and tools. BMC Syst. Biol. 7, 135 (2013).
38. Zheng, Y. & Sriram, G. Mathematical Modeling: Bridging the Gap between Concept and Realization in Synthetic Biology. J. Biomed. Biotechnol. 2010, 1-16 (2010).
39. Kaznessis, Y. N. Models for synthetic biology. BMC Syst. Biol. 1, 47 (2007).
40. Lewis, D. D., Villarreal, F. D., Wu, F. & Tan, C. Synthetic Biology Outside the Cell: Linking Computational Tools to Cell-Free Systems. Front. Bioeng. Biotechnol. 2, (2014).
41. Amar, P. HSIM: a simulation programme to study large assemblies of proteins. J. Biol. Phys. Chem. 4, 79-84 (2002).
42. Amar, P. & Paulevé, L. HSIM: A Hybrid Stochastic Simulation System for Systems Biology. Electron. Notes Theor. Comput. Sci. 313, 3-21 (2015).
43. Calzone, L., Fages, F. & Soliman, S. BIOCHAM: an environment for modeling biological systems and formalizing experimental knowledge. Bioinforma. Oxf. Engl. 22, 1805-1807 (2006).
44. Gay, S., Soliman, S. & Fages, F. A graphical method for reducing and relating models in systems biology. Bioinformatics 26, i575-i581 (2010).
45. Bouffar, M., Molina, F. & Amar, P. Extracting logic gates from a metabolic network. in pp. 13 (2015).
46. Hansen, N. & Ostermeier, A. Completely derandomized self-adaptation in evolution strategies. Evol. Comput. 9, 159-195 (2001).
47. Beal, J. Signal-to-Noise Ratio Measures Efficacy of Biological Computing Devices and Circuits. Front. Bioeng. Biotechnol. 3, (2015).
48. Walde, P., Cosentino, K., Engel, H. & Stano, P. Giant Vesicles: Preparations and Applications. ChemBioChem 11, 848-865 (2010).
49. Reeves, J. P. & Dowben, R. M. Formation and properties of thin-walled phospholipid vesicles. J. Cell. Physiol. 73, 49-60 (1969).
50. Pautot, S., Frisken, B. J. & Weitz, D. A. Engineering asymmetric vesicles. Proc. Natl. Acad. Sci. 100, 10718-10721 (2003).
51. van Swaay, D. & deMello, A. Microfluidic methods for forming liposomes. Lab. Chip 13, 752 (2013).
52. Jahn, A., Vreeland, W. N., Gaitan, M. & Locascio, L. E. Controlled vesicle self-assembly in microfluidic channels with hydrodynamic focusing. J. Am. Chem. Soc. 126, 2674-2675 (2004).
53. Richmond, D. L. et al. Forming giant vesicles with controlled membrane composition, asymmetry, and contents. Proc. Natl. Acad. Sci. 108, 9431-9436 (2011).
54. Tan, Y.-C., Hettiarachchi, K., Siu, M., Pan, Y.-R. & Lee, A. P. Controlled microfluidic encapsulation of cells, proteins, and microbeads in lipid vesicles. J. Am. Chem. Soc. 128, 5656-5658 (2006).
55. Matosevic, S. & Paegel, B. M. Stepwise Synthesis of Giant Unilamellar Vesicles on a Microfluidic Assembly Line. J. Am. Chem. Soc. 133, 2798-2800 (2011).
56. Teh, S.-Y., Khnouf, R., Fan, H. & Lee, A. P. Stable, biocompatible lipid vesicle generation by solvent extraction-based droplet microfluidics. Biomicrofluidics 5, 044113 (2011).
57. Jahn, A. et al. Microfluidic Mixing and the Formation of Nanoscale Lipid Vesicles. ACS Nano 4, 2077-2087 (2010).
58. Mijajlovic, M., Wright, D., Zivkovic, V., Bi, J. X. & Biggs, M. J. Microfluidic hydrodynamic focusing based synthesis of POPC liposomes for model biological systems. Colloids Surf. B Biointerfaces 104, 276-281 (2013).
59. Jahn, A., Vreeland, W. N., DeVoe, D. L., Locascio, L. E. & Gaitan, M. Microfluidic directed formation of liposomes of controlled size. Langmuir ACS J. Surf. Colloids 23, 6289-6293 (2007).
60. Shum, H. C., Lee, D., Yoon, I., Kodger, T. & Weitz, D. A. Double Emulsion Templated Monodisperse Phospholipid Vesicles. Langmuir 24, 7651-7653 (2008).
61. Shum, H. C., Kim, J.-W. & Weitz, D. A. Microfluidic Fabrication of Monodisperse Biocompatible and Biodegradable Polymersomes with Controlled Permeability. J. Am. Chem. Soc. 130, 9543-9549 (2008).
62. Gunther, A. & Jensen, K. F. Multiphase microfluidics: from flow characteristics to chemical and materials synthesis. Lab. Chip 6, 1487-1503 (2006).
63. Utada, A. S. Monodisperse Double Emulsions Generated from a Microcapillary Device. Science 308, 537-541 (2005).
64. Kozlov, M., Quarmyne, M., Chen, W. & McCarthy, T. J. Adsorption of Poly(vinyl alcohol) onto Hydrophobic Substrates. A General Approach for Hydrophilizing and Chemically Activating Surfaces. Macromolecules 36, 6054-6059 (2003).
65. Liposomes as tools in basic research and industry. (CRC Press, 1995).
66. Williams, M. S., Longmuir, K. J. & Yager, P. A practical guide to the staggered herringbone mixer. Lab. Chip 8, 1121 (2008).
67. Gullapalli, R. R., Demirel, M. C. & Butler, P. J. Molecular dynamics simulations of DiI-C18(3) in a DPPC lipid bilayer. Phys. Chem. Chem. Phys. 10, 3548 (2008).
68. Nagle J F & Tristram-Nagle S. Structure of lipid bilayers. Biochim Biophys Acta. 159-95. (2000).
69. Planchet, E. & Kaiser, W. M. Nitric oxide (NO) detection by DAF fluorescence and chemiluminescence: a comparison using abiotic and biotic NO sources. J. Exp. Bot. 57, 3043-3055 (2006).
70. Dean, J. V. & Harper, J. E. The Conversion of Nitrite to Nitrogen Oxide(s) by the Constitutive NAD(P)H-Nitrate Reductase Enzyme from Soybean. Plant Physiol. 88, 389-395 (1988).
71. Yokota, K. & Yamazaki, I. Analysis and computer simulation of aerobic oxidation of reduced nicotinamide adenine dinucleotide catalyzed by horseradish peroxidase. Biochemistry (Mosc.) 16, 1913-1920 (1977).
72. Singh, R. et al. Catalase-peroxidases (KatG) exhibit NADH oxidase activity. J. Biol. Chem. 279, 43098-43106 (2004).
73. Afanasyeva, M. S., Taraban, M. B., Purtov, P. A., Leshina, T. V. & Grissom, C. B. Magnetic spin effects in enzymatic reactions: radical oxidation of NADH by horseradish peroxidase. J. Am. Chem. Soc. 128, 8651-8658 (2006).

74. Yorita, K. et al. Conversion of L-lactate oxidase to a long chain alpha-hydroxyacid oxidase by site-directed mutagenesis of alanine 95 to glycine. J. Biol. Chem. 271, 28300-28305 (1996).

75. Liu, X. et al. Application of carbon fiber composite minielectrodes for measurement of kinetic constants of nitric oxide decay in solution. Nitric Oxide 23, 311-318 (2010).

76. Li, H., Kundu, T. K. & Zweier, J. L. Characterization of the Magnitude and Mechanism of Aldehyde Oxidase-mediated Nitric Oxide Production from Nitrite. J. Biol. Chem. 284, 33850-33858 (2009).

77. Kojima, H. et al. Detection and imaging of nitric oxide with novel fluorescent indicators: diaminofluoresceins. Anal. Chem. 70, 2446-2453 (1998).

78. Espey, M. G., Miranda, K. M., Thomas, D. D. & Wink, D. A. Distinction between nitrosating mechanisms within human cells and aqueous solution. J. Biol. Chem. 276, 30085-30091 (2001).

79. Arita, N. O., Cohen, M. F., Tokuda, G. & Yamasaki, H. in Nitric Oxide in Plant Growth, Development and Stress Physiology (eds. Lamattina, L. & Polacco, J. C.) 5, 269-280 (Springer Berlin Heidelberg, 2007).

80. E. F. Olasehinde & et al. Reaction Kinetics for Nitrosation of DAF-2 in Air Saturated Nitric Oxide Solution. Nature & Science p129 (2012).

81. Chaize, B., Colletier, J.-P., Winterhalter, M. & Fournier, D. Encapsulation of enzymes in liposomes: high encapsulation efficiency and control of substrate permeability. Artif. Cells. Blood Substit. Immobil. Biotechnol. 32, 67-75 (2004).

82. Yoshimoto, M. in Enzyme Stabilization and Immobilization (ed. Minteer, S. D.) 679, 9-18 (Humana Press, 2011).

83. Sunami, T., Hosoda, K., Suzuki, H., Matsuura, T. & Yomo, T. Cellular Compartment Model for Exploring the Effect of the Lipidic Membrane on the Kinetics of Encapsulated Biochemical Reactions. Langmuir 26, 8544-8551 (2010).

84. Thiele, J. et al. Fabrication of Polymersomes using Double-Emulsion Templates in Glass-Coated Stamped Microfluidic Devices. Small 6, 1723-1727 (2010).

85. Duncanson, W. J. et al. Microfluidic synthesis of advanced microparticles for encapsulation and controlled release. Lab. Chip 12, 2135 (2012).

86. Stanish, I. & Singh, A. Highly stable vesicles composed of a new chain-terminus acetylenic photopolymeric phospholipid. Chem. Phys. Lipids 112, 99-108 (2001).

87. Osyczka, A., Moser, C. C., Daldal, F. & Dutton, P. L. Reversible redox energy coupling in electron transfer chains. Nature 427, 607-612 (2004).

88. Katzen, F., Deshmukh, M., Daldal, F. & Beckwith, J. Evolutionary domain fusion expanded the substrate specificity of the transmembrane electron transporter DsbD. EMBO J. 21, 3960-3969 (2002).

89. Page, C. C., Moser, C. C., Chen, X. & Dutton, P. L. Natural engineering principles of electron tunnelling in biological oxidation-reduction. Nature 402, 47-52 (1999).

90. Wakeham, M. C. & Jones, M. R. Rewiring photosynthesis: engineering wrong-way electron transfer in the purple bacterial reaction centre. Biochem. Soc. Trans. 33, 851-857 (2005).

91. Hermann, T. & Patel, D. J. Adaptive recognition by nucleic acid aptamers. Science 287, 820-825 (2000).

92. Šmuc, T., Ahn, I.-Y. & Ulrich, H. Nucleic acid aptamers as high affinity ligands in biotechnology and biosensorics. J. Pharm. Biomed. Anal. 81-82, 210-217 (2013).

93. Falciani, C., Lozzi, L., Pini, A. & Bracci, L. Bioactive peptides from libraries. Chem. Biol. 12, 417-426 (2005).

94. Stoltenburg, R., Reinemann, C. & Strehlitz, B. SELEX—a (r)evolutionary method to generate high-affinity nucleic acid ligands. Biomol. Eng. 24, 381-403 (2007).

95. Hanes, J., Schaffitzel, C., Knappik, A. & Plückthun, A. Picomolar affinity antibodies from a fully synthetic naive library selected and evolved by ribosome display. Nat. Biotechnol. 18, 1287-1292 (2000).

96. Binz, H. K., Amstutz, P. & Plückthun, A. Engineering novel binding proteins from nonimmunoglobulin domains. Nat. Biotechnol. 23, 1257-1268 (2005).

97. Song, S., Kole, S. & Bernier, M. A chemical cross-linking method for the analysis of binding partners of heat shock protein-90 in intact cells. BioTechniques (2012). doi:10.2144/000113856

98. Xiang, Z. et al. Proximity-Enabled Protein Crosslinking through Genetically Encoding Haloalkane Unnatural Amino Acids. Angew. Chem. Int. Ed. 53, 2190-2193 (2014).

99. Strickland, D. et al. TULIPs: tunable, light-controlled interacting protein tags for cell biology. Nat. Methods 9, 379-384 (2012).

100. Rakhit, R., Navarro, R. & Wandless, T. J. Chemical biology strategies for posttranslational control of protein function. Chem. Biol. 21, 1238-1252 (2014).

101. Riggsbee, C. W. & Deiters, A. Recent advances in the photochemical control of protein function. Trends Biotechnol. 28, 468-475 (2010).

102. Watanabe, R. et al. Arrayed lipid bilayer chambers allow single-molecule analysis of membrane transporter activity. Nat. Commun. 5, (2014).

103. Stillwell, W. An introduction to biological membranes: from bilayers to rafts. (Elsevier/Academic Press, 2013).

104. Karp, R. M. in Complexity of Computer Computations (eds. Miller, R. E., Thatcher, J. W. & Bohlinger, J. D.) 85-103 (Springer US, 1972). at http://link.springer.com/10.1007/978-1-4684-2001-2_9

105. Wang, T. J. et al. Metabolite profiles and the risk of developing diabetes. Nature Medicine 17 (4) 448-454 (2011)

106. Jang, C. et al. A branched-chain amino acid metabolite drives vascular fatty acid transport and causes insulin-resistance. Nature Medicine 22 (4) 421-426 (2016)

107. Newgard, C. B. Interplay between Lipids and Branched-Chain Amino Acids in Development of Insulin Resistance. Cell Metabolism 15 606-614 (2012)

The invention claimed is:

1. A method for the diagnosis of, or prediction of the risk of, an insulin-resistance pathology in a patient, said method comprising:
a) obtaining a composition comprising at least one of:
(i) non-living vesicles comprising encapsulated leucine dehydrogenase enzyme and non-living vesicles comprising encapsulated glucose-1-dehydrogenase enzyme;
(ii) non-living vesicles comprising encapsulated leucine dehydrogenase enzyme and non-living vesicles comprising glucose oxydase enzyme;

(iii) non-living vesicles comprising encapsulated leucine dehydrogenase enzyme, non-living vesicles comprising encapsulted glucose-1-dehydrogenase enzyme, and non-living vesicles comprising encapsulated glucose oxydase enzyme;

(iv) non-living vesicles comprising both encapsulated leucine dehydrogenase enzyme and glucose-1-dehydrogenase enzyme;

(v) non-living vesicles comprising both encapsulated leucine dehydrogenase enzyme and glucose oxydase enzyme; and (vi) non-living vesicles comprising encapsulated leucine dehydrogenase enzyme, glucose-1-dehydrogenase enzyme, and glucose oxydase enzyme;

b) brining into contact said composition comprising vesicles with a sample of the patient's blood, plasma, serum, and/or urine to generate two different output signals resulting from enzymatic reactions of the enzymes in the composition with components of the sample inside said vesicles, wherein the components comprise glucose and branched chain amino acids (BCAAs);

c) detecting or measuring the output signals generated at step b), said output signals being indicative of the levels of glucose and BCAAs and the diagnosis of, or prediction of the risk of, an insulin-resistnace pathology in said patient, wherein when the output signals indicate elevated levels of BCAA and glucose in the sample, the patient has, or is at risk of having, diabetes and when the output signals indicated elevated levels of BCAA but not elevated levels of glucose in the sample, the patient has, or is at risk of having, insulin resistance, wherein the BCAA and glucose levels are compared relative to standardized scales.

2. The method of claim 1, wherein said patient suffers from diabetes.

3. The method according to claim 1, wherein the vesicles further comprise resazurin, nicotinamide adenine dinucleotide (NAD), 2,2'-azino-bis (3-ethylbenzothiazoline-6-sulphonic acid (ABTS) and/or 3-(4,5-dimethylthiazol-2-yl)-2, 5-diphenyltetrazolium bromide (MTT) metabolites.

4. The method according to one of claim 1, wherein said sample is contacted with two different populations of vesicles comprising:
   a) a first population of vesicles comprising encapsulated:
      enzyme: leucine dehydrogenase; and
      metabolites: MTT, NAD; and
   b) a second population of vesicles comprising encapsulated:
      enzyme: Glucose-1-dehydrogenase or Glucose oxydase and Horse radish-peroxidase (HRP); and
      metabolites: resazurin.

5. The method according to one of claim 1, wherein the output signal is a chemical, biological, electronic or photonic signal, or a physicochemical output signal.

6. The method of claim 1, wherein the patient is a human.

7. The method of claim 1, wherein the sample is urine.

\* \* \* \* \*